United States Patent
Huttenlocher et al.

(10) Patent No.: US 11,980,654 B2
(45) Date of Patent: May 14, 2024

(54) METHOD TO INHIBIT NEUTROPHIL RECRUITMENT TO DAMAGED TISSUE USING MYELOID-DERIVED GROWTH FACTOR

(71) Applicant: Wisconsin Alumni Research Foundation, Madison, WI (US)

(72) Inventors: Anna Huttenlocher, Madison, WI (US); Deane Mosher, Madison, WI (US); Valeriu Bortnov, Madison, WI (US); David Bennin, Madison, WI (US); Ruth Anne Houseright, Madison, WI (US); Frances M Smith, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/481,490

(22) Filed: Sep. 22, 2021

(65) Prior Publication Data
US 2022/0168390 A1    Jun. 2, 2022

Related U.S. Application Data

(60) Provisional application No. 63/081,664, filed on Sep. 22, 2020.

(51) Int. Cl.
*A61K 38/18* (2006.01)
*A61P 17/02* (2006.01)

(52) U.S. Cl.
CPC .............. *A61K 38/18* (2013.01); *A61P 17/02* (2018.01)

(58) Field of Classification Search
None
See application file for complete search history.

(56) References Cited

FOREIGN PATENT DOCUMENTS

WO    WO 2021/148411 A1    7/2021

OTHER PUBLICATIONS

Wang et al. Mydgf promotes Cardiomyocyte proliferation and Neonatal Heart regeneration. Theranostics.2020, 10:9100-9112.*
Korf-Klingebiel. Myeloid derived growth factor (C19 or F10) mediates cardiac repair following myocardial infarction. Nat. Med., 2015,21:140-149.*
Zhao et al. Production of bioactive recombinant human myeloid-derived growth factor in *Escherichia coli* and its mechanism on vascular endothelial cell proliferation, J.CellMol. Med.,2020,24,1189-1199.*
Bortnov et al., "Solution structure of human myeloid-derived growth factor suggests a conserved functioni n the endoplasmic reticulum," Nature Communications 2019, 10:5612.*
Altschul et al., Gapped BLAST and PSI-BLAST: a new generation of protein database search programs, *Nucleic Acids Res.* 1997, 25:3389-3402.
Apweiler et al., UniProt: the universal protein knowledgebase. *Nucleic Acids Res.* 2017, vol. 32, Database issue D115-D119.
Barros-Becker, F., J.M. Squirrell, R. Burke, J. Chini, J. Rindy, A. Karim, K.W. Eliceiri, A. Gibson, and A. Huttenlocher, Distinct Tissue Damage and Microbial Cues Drive Neutrophil and Macrophage Recruitment to Thermal Injury. *iScience.* 2020, 23:101699.
Bortnov, V., D.S. Annis, F.J. Fogerty, K.T. Barretto, K.B. Turton, and D.F. Mosher, Myeloid-derived growth factor is a resident endoplasmic reticulum protein. *J. Biol. Chem.*, 2018, 293:13166-13175.
Bortnov, V., Myeloid-Derived Growth Factor (MYDGF): Investigations of Structure and Function. The University of Wisconsin—Madison, Ann Arbor, 2020, 1-173.
Brubaker, A.L., J.L. Rendon, L. Ramirez, M.A. Choudhry, and E.J. Kovacs, Reduced neutrophil chemotaxis and infiltration contributes to delayed resolution of cutaneous wound infection with advanced age. *J. Immunol*, 2013. 190:1746-1757.
De Oliveira, S., E.E. Rosowski, and A. Huttenlocher, Neutrophil migration in infection and wound repair: going forward in reverse. *Nat. Rev. Immunol.*, 2016, 16:378-391.
Deng, Q., S.K. Yoo, P.J. Cavnar, J.M. Green, and A. Huttenlocher, Dual roles for Rac2 in neutrophil motility and active retention in zebrafish hematopoietic tissue. *Dev. Cell*, 2011, 21:735-745.
Deng, Q, Harvie, EA and Huttenlocher A., Distinct signaling mechanisms mediate neutrophil attraction to bacterial infection and tissue injury, *Cell Microbiology*, 2012, 14: 517-28.
Devereux et al., A comprehensive set of sequence analysis programs for the VAX, *Nucl. Acid Res.*, 1984, 12:387-395.
Ebaid, H, Neutrophil depletion in the early inflammatory phase delayed cutaneous wound healing in older rats: improvements due to the use of un- denatured camel whey protein. *Diagn. Pathol*, 2014, 9:46.
Ebenhoch, R., A. Akhdar, M.R. Reboll, M. Korf-Klingebiel, P. Gupta, J. Armstrong, Y. Huang, L. Frego, I. Rybina, J. Miglietta, et al., Crystal structure and receptor-interacting residues of MYDGF—a protein mediating ischemic tissue repair. *Nat. Commun.*, 2019, 10:5379.
Edgar, Robert C., Muscle: a multiple sequence alignment method with reduced time and space complexity, *BMC Bioinformatics*, 2004, 5:113.
Elks, P.M., F.J. Van Eeden, G. Dixon, X. Wang, C.C. Reyes-Aldasoro, P.W. Ingham, M.K.B. Whyte, S.R. Walmsley, and S.A. Renshaw, Activation of hypoxia-inducible factor-1α (Hif-1α) delays inflammation resolution by reducing neutrophil apoptosis and reverse migration in a zebrafish inflammation model. *Blood*, 2011, 118:712-722.

(Continued)

*Primary Examiner* — Maury A Audet
(74) *Attorney, Agent, or Firm* — Joseph T. Leone; DeWitt LLP

(57) ABSTRACT

A method to inhibit neutrophil recruitment to damaged tissue, thereby inhibiting inflammation in a subject. The method includes administering to an anti-inflammatory amount of a myeloid-derived growth factor ("MYDGF"). Also disclosed are corresponding pharmaceutical compositions of matter containing the MYDGF.

12 Claims, 28 Drawing Sheets
(24 of 28 Drawing Sheet(s) Filed in Color)

Specification includes a Sequence Listing.

(56) References Cited

OTHER PUBLICATIONS

Ellett, F., L. Pase, J.W. Hayman, A. Andrianopoulos, and G.J. Lieschke, mpeg 1 promoter transgenes direct macrophage-lineage expression in zebrafish. *Blood*, 2011, 117:e49-e56.

Ferrari et al., Genetics, in Harwood et al., (eds.), Bacillus, Plenum Publishing Corp., pp. 57-72, 1989.

Freisinger, C.M. and Huttenlocher, A., Live Imaging and Gene Expression Analysis in Zebrafish Identifies a Link between Neutrophils and Epithelial to Mesenchymal Transition. PLos On 9(11): 112183, 2014.

Gagnon, J.A., E. Valen, S.B. Thyme, P. Huang, L. Akhmetova, A. Pauli, T.G. Montague, S. Zimmerman, C. Richter, and A.F. Schier, Efficient mutagenesis by Cas9 protein-mediated oligonucleotide insertion and large-scale assessment of single-guide RNAs. *PLoS One*. 9:e98186, 2014.

Golenberg N, Squirrell J, Bennin DA, Rindy J, Pistono PE, Eliceiri K, Shelef MA and Huttenlocher A., Citrullination regulates wound responses and tissue regeneration in zebrafish, *J. Cell Biol.*, 2020, vol. 219, No. 4, e291908164; https://foi.org/10.1083/jcb.201908164.

Guerot-Fleury et al., Antibiotic-resistance cassettes for *Bacillus subtilis*, Gene, 1995, 167:335-337.

"Handbook of Pharmaceutical Salts, Properties, Selection, and Use," P.H. Stahl and C.G. Wermuch, Eds., © 2008, Wiley-VCH (Zurich, Switzerland), ISBN: 978-3-90639-058-1. (Book—Copy Not Provided).

Harvie, E.A., and A. Huttenlocher, Non-invasive Imaging of the Innate Immune Response in a Zebrafish Larval Model of *Streptococcus iniae* Infection. *J. Vis. Exp.*, 2015, 98:52788.

He, M., Y. Li, L. Wang, B. Guo, W. Mei, B. Zhu, J. Zhang, Y. Ding, B. Meng, L. Zhang, et al., MYDGF attenuates podocyte injury and proteinuria by activating Akt/BAD signal pathway in mice with diabetic kidney disease. *Diabetologia.*, 2020, 63:1916-1931.

Heilmann S. et al. "A quantitative system for studying metastasis using transparent zebrafish," *Cancer Res*. Oct. 15, 2015; 75(20):4272-4282. doi: 10.1158/0008-5472.CAN-14-3319. Epub Aug. 17, 2015.

Hind L and Huttenlocher A., Neutrophil reverse migration and a chemokinetic resolution. *Developmental Cell*, 2018, 47: 404-56.

Houseright, R.A., E.E. Rosowski, P.Y. Lam, S.J.M. Tauzin, O. Mulvaney, C.N. Dewey, and A. Huttenlocher., Cell type specific gene expression profiling reveals a role for complement component C3 in neutrophil responses to tissue damage. *Sci. Rep*, 2020, 10:15716.

Huang, C., and P. Niethammer, Tissue Damage Signaling Is a Prerequisite for Protective Neutrophil Recruitment to Microbial Infection in Zebrafish. *Immunity.* 2018, 48: 1006-1013.e6.

Huemer, K., J.M. Squirrell, R. Swader, D.C. Lebert, A. Huttenlocher, and K.W. Eliceiri, zWEDGI: Wounding and Entrapment Device for Imaging Live Zebrafish Larvae. *Zebrafish.*, 2017, 14:42-50.

Korf-Klingebiel, M., M.R. Reboll, S. Klede, T. Brod, A. Pich, F. Polten, L.C. Napp, J. Bauersachs, A. Ganser, E. Brinkmann, et al., Myeloid derived growth factor (C19orf10) mediates cardiac repair following myocardial infarction. *Nat. Med.*, 2015, 21:140-149.

Lafave, M.C., G.K. Varshney, M. Vemulapalli, J.C. Mullikin, and S.M. Burgess, A defined zebrafish line for high-throughput genetics and genomics: NHGRI-1. *Genetics*, 2014, 198:167-170.

Lam P, Fischer RS, Shin WD, Waterman CM and Huttenlocher A., Spinning disk confocal imaging of neutrophil migration in zebrafish. *Methods in Molecular Biology*, 2014, 1124:219-33.

Lam PY, Harvie EA, Huttenlocher A., Heat shock modulates neutrophil motility in zebrafish. *PLoS One*, Dec. 19, 2013;8(12):e84436.

Larkin M. A., et al., (2007) CLUSTALW2, ClustalW and ClustalX version 2, *Bioinformatics*, 2007, 23(21):2947-2948.

Lebert Dc and Huttenlocher A., Inflammation and wound repair, *Semin Immunol*, 2014, 26:315-20.

Lebert D, Squirrell JM, Freisinger C, Rindy J, Golenberg N, Frecentese G, Gibson A, Eliceiri KW, Huttenlocher A., Damage induced reactive oxygen species regulate vimentin and dynamic collagen-based projections to mediate wound repair, 2018, *eLife* e30703.

Livak, K.J., and T.D. Schmittgen, Analysis of relative gene expression data using real-time quantitative PCR and the 2(-Delta Delta C(T)) Method. *Methods.*, 2001, 25:402-408.

Mathias, J.R., B.J. Perrin, T.X. Liu, J. Kanki, A.T. Look, and A. Huttenlocher, Resolution of inflammation by retrograde chemotaxis of neutrophils in transgenic zebrafish. *J. Leukoc. Biol..* 2006, 80:1281-1288.

Maurer, L.M., B.R. Tomasini-Johansson, W. MA, D.S. Annis, N.L. Eickstaedt, M.G. Ensenberger, K.A. Satyshur, and D.F. Mosher. 2010. Extended binding site on fibronectin for the functional upstream domain of protein F1 of *Streptococcus pyogenes*. *J. Biol. Chem*. 285:41087-41099.

Miskolci, V., J. Squirrell, J. Rindy, W. Vincent, J.D. Sauer, A. Gibson, K.W. Eliceiri, and A. Huttenlocher, Distinct inflammatory and wound healing responses to complex caudal fin injuries of larval zebrafish, 2019, *eLife*. 8:e45976.

Montague, T.G., J.M. Cruz, J.A. Gagnon, G.M. Church, and E. Valen, Chopchop: a CRISPR/Cas9 and TALEN web tool for genome editing. *Nucleic Acids Res.*, 2014, 42(W1):W401-7.

Needleman and Wunsch, A General Method Applicable to the Search for Similarities in the Amino Acid Sequence of Two Proteins, *J. Mol. Biol.*, 1970, 48:443.

H. Neurath and R. L. Hill, in "The Proteins," Academic Press, New York, 1979 (Book—Copy Not Provided).

Notredame et al., T-coffee: A Novel Method for Fast and Accurate Multiple Sequence Alignment, 2000, *J. Mol. Biol.*, 302:205-217.

Palmeros et al., A family of removable cassettes designed to obtain antibiotic-resistance-free genomic modifications of *Escherichia coli* bacteria, Gene, 247:255-264, 2000.

PCT International Search Report and Written Opinion, dated Feb. 7, 2022, PCT/US2021/051499.

Pearson and Lipman, Improved tools for biological sequence comparison, *Proc. Natl. Acad. Sci. USA*, 1988, 85:2444.

Powell D, Tauzin S, Hind LE, Deng Q, Beebe DJ and Huttenlocher A. (2017) Chemokine signaling and the regulation of bidirectional leukocyte migration in interstitial tissues. *Cell Reports*, 2017, 9(8):1572-1585.

Prasch, A.L., R.L. Tanguay, V. Mehta, W. Heideman, and R.E. Peterson, Identification of zebrafish ARNT1 homologs: 2,3,7,8-tetrachlorodibenzo-p-dioxin toxicity in the developing zebrafish requires ARNT1. *Mol. Pharmacol.*, 2006, 69:776-787.

Roh-Johnson M, et al. "Macrophage-dependent cytoplasmic transfer during melanoma invasion in vivo," *Dev Cell*. Dec. 4, 2017;43(5):549-562.e6.

Rosowski, E.E., Q. Deng, N.P. Keller, and A. Huttenlocher, Rac2 Functions in Both Neutrophils and Macrophages To Mediate Motility and Host Defense in Larval Zebrafish. *J. Immunol*, 2016, 197:4780-4790.

Rosowski EE, Raffa N, Knox BP, Golenberg N, Keller NP and Huttenlocher A., Macrophages inhibit Aspergillus fumigatus germination and neutrophil-mediated fungal killing, *PLoS Pathogens*, 2018, 4(8):e1007229.

Rueden, C.T., J. Schindelin, M.C. Hiner, B.E. Dezonia, A.E. Walter, E.T. Arena, and K.W. Eliceiri, ImageJ2: ImageJ for the next generation of scientific image data. *BMC Bioinformatics*, 2017. 18:529.

Schoen TJ, Rosowski EE, Knox BP, Bennin D, Keller NP and Huttenlocher A., Neutrophil phagocyte oxidase activity controls invasive fungal growth and inflammation in zebrafish, *Journal of Cell Science*, 2020, 133, jcs236539. doi: 10.1242/jcs.236539.

Smith and Waterman, Comparison of Biosequences, *Adv. Appl. Math.*, 1981, 2:482.

Sunagozaka, H., M. Honda, T. Yamashita, R. Nishino, H. Takatori, K. Arai, T. Yamashita, Y. Sakai, and S. Kaneko, Identification of a secretory protein c19orf10 activated in hepatocellular carcinoma. *Int. J. Cancer.*, 2011, 129:1576-1585.

Tauzin, S., T.W. Starnes, F.B. Becker, P.Y. Lam, and A. Huttenlocher, Redox and Src family kinase signaling control leukocyte wound attraction and neutrophil reverse migration. *J. Cell Biol*. 2014, 207:589-598.

(56) References Cited

OTHER PUBLICATIONS

Thompson J. D., Higgins D. G., Gibson T. J., Clustal W., Improving the sensitivity of progressive multiple sequence alignment through sequence weighting, position-specific gap penalties and weight matrix choice, *Nucleic Acids Research*, 1994, 22:4673-4680.

Trieu-Cuot P. and Courvalin, P., Nucleotide sequence of the *Streptococcus faecalis* plasmid gene encoding the 3'5"-aminoglycoside phosphotransferase type III, Gene, 1983, 23:331-341.

Trychta, K.A., E.J. Heathward, A. Sulima, S. Bäck, M. Farokhnia, C.T. Richie, L. Leggio, K.C. Rice, and B.K. Harvey, Extracellular esterase activity as an indicator of endoplasmic reticulum calcium depletion. *Biomarkers.*, 2018, 23:756-765.

Uderhardt S, Martins AJ, Tsang JS, Lämmermann T, Germain RN, Resident Macrophages Cloak Tissue Microlesions to Prevent Neutrophil-Driven Inflammatory Damage, *Cell*, 2019, 177, 541-555.

Walmsley, S.R., E.R. Chilvers, A.A. Thompson, K. Vaughan, H.M. Marriott, L.C. Parker, G. Shaw, S. Parmar, M. Schneider, I. Sabroe, et al., Prolyl hydroxylase 3 (PHD3) is essential for hypoxic regulation of neutrophilic inflammation in humans and mice. *J. Clin. Invest.*, 2011, 121:1053-1063.

Walters KB, Green JM, Surfus JC, Yoo SK, Huttenlocher A., Live imaging of neutrophil motility in a zebrafish model of WHIM syndrome. *Blood*, 2010, 116(15):2803-11.

Wang, J., M. Hossain, A. Thanabalasuriar, M. Gunzer, C. Meininger, and P. Kubes, Visualizing the function and fate of neutrophils in sterile injury and repair. *Science*. 2017, 358:111-116.

Wang, Y., Y. Li, J. Feng, W. Liu, Y. Li, J. Liu, Q. Yin, H. Lian, L. Liu, and Y. Nie, Mydgf promotes Cardiomyocyte proliferation and Neonatal Heart regeneration. Theranostics. 2020, 10:9100-9112.

Weiler, T., Q. Du, O. Krokhin, W. Ens, K. Standing, H. El-Gabalawy, and J.A. Wilkins, The identification and characterization of a novel protein, c19orf10, in the synovium. *Arthritis Res. Ther.*, 2007, 9:R30.

Yoo, S.K., Q. Deng, P.J. Cavnar, Y.I. Wu, K.M. Hahn, and A. Huttenlocher, Differential regulation of protrusion and polarity by PI3K during neutrophil motility in live zebrafish. *Dev. Cell.*, 2010, 18:226-236.

Yoo, S.K., and A. Huttenlocher. 2011. Spatiotemporal photolabeling of neutrophil trafficking during inflammation in live zebrafish. *J. Leukoc. Biol.* 89:661-667.

Yoo, SK, Starnes, T, Deng Q and Huttenlocher, A., Lyn is a redox sensor that mediates leukocyte wound attraction in vivo, *Nature*, 2011, 480(7375):109-12.

Zhao, L. et al., Production of bioactive recombinant human myeloid-derived growth factor in *Escherichia coli* and its mechanism on vascular endothelial cell proliferation, *J. Cell Mol. Med.*, 2020, 24, 1189-1199.

\* cited by examiner

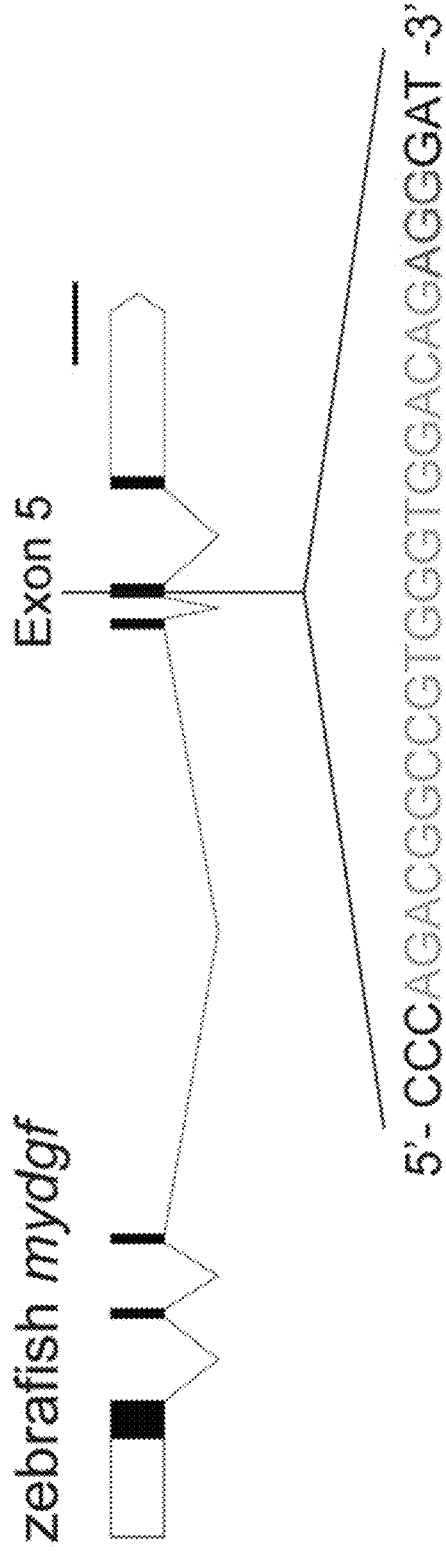

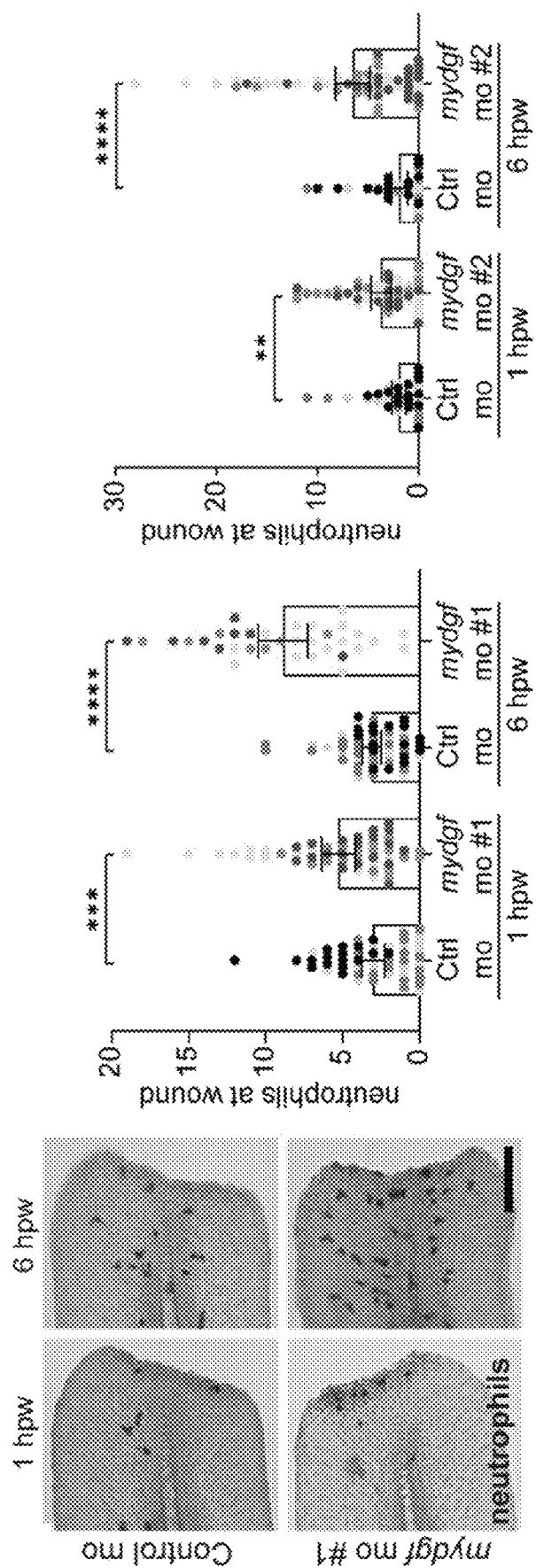

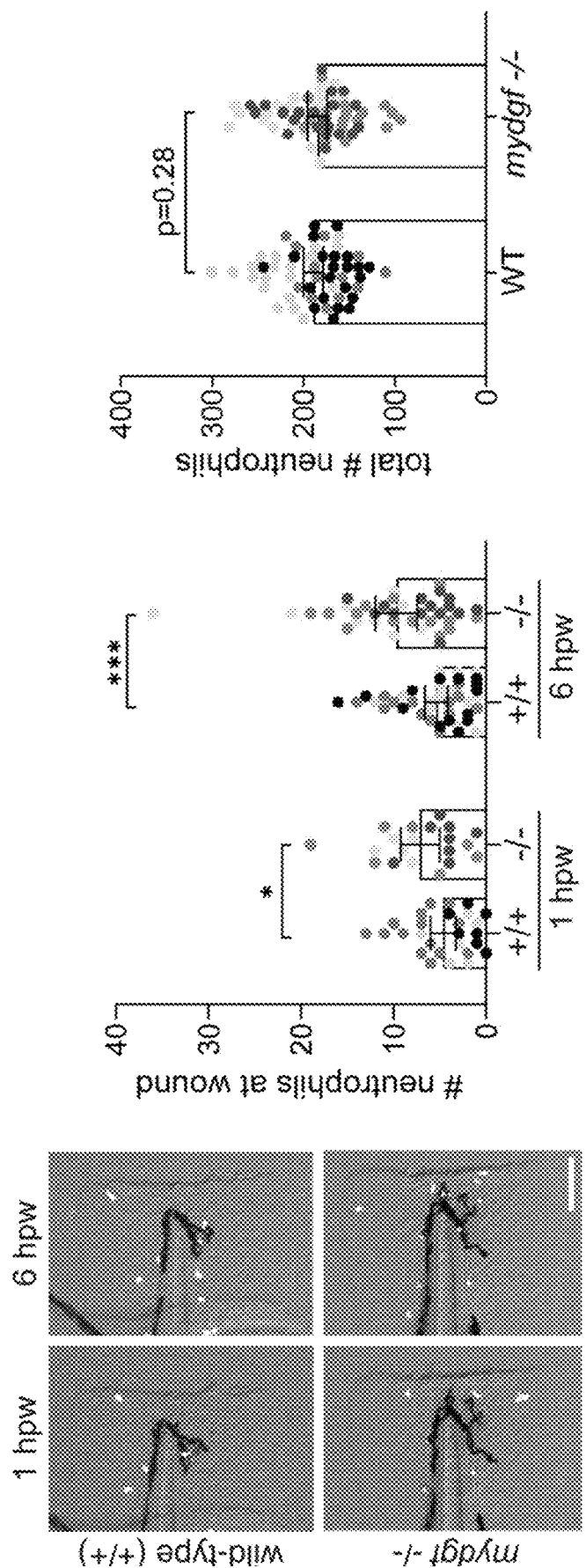

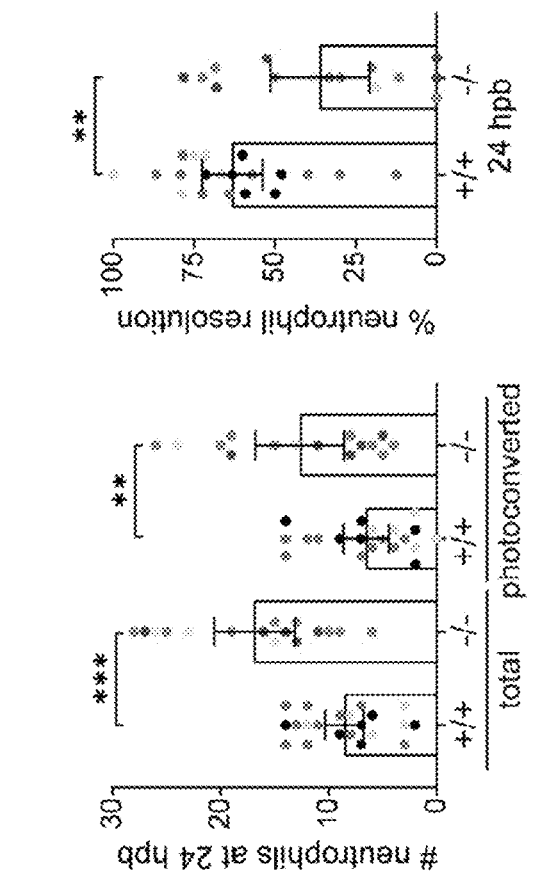
Fig. 6F
Fig. 6E
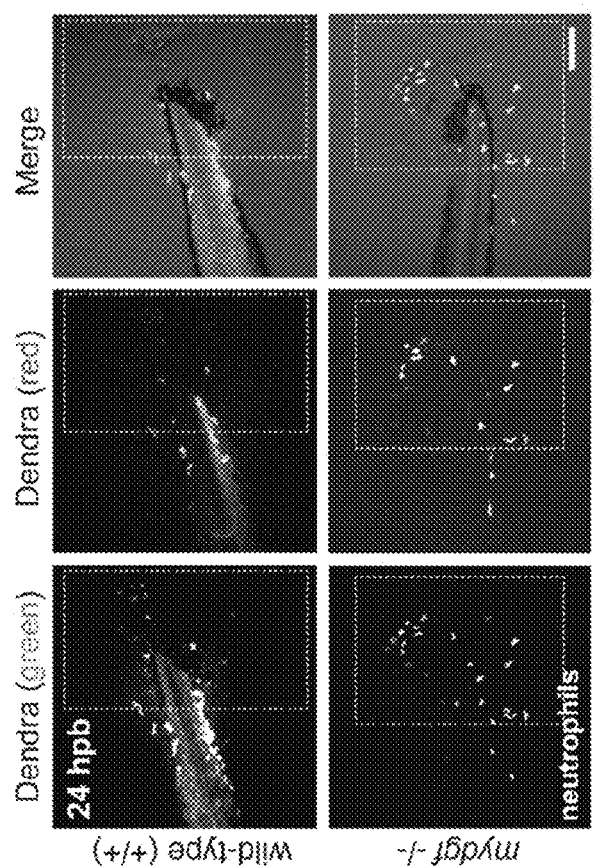
Fig. 6D

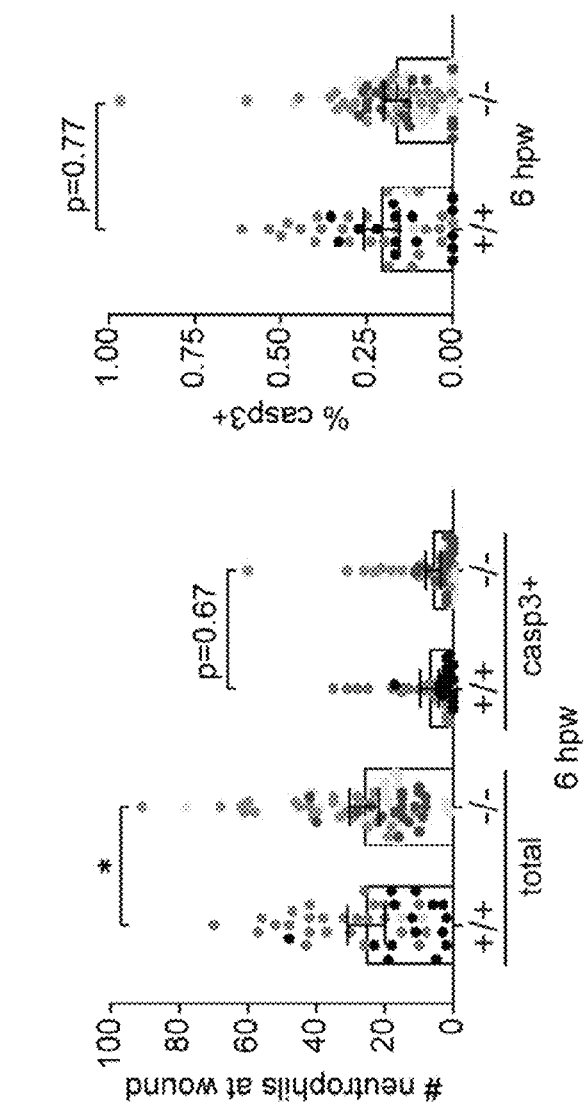
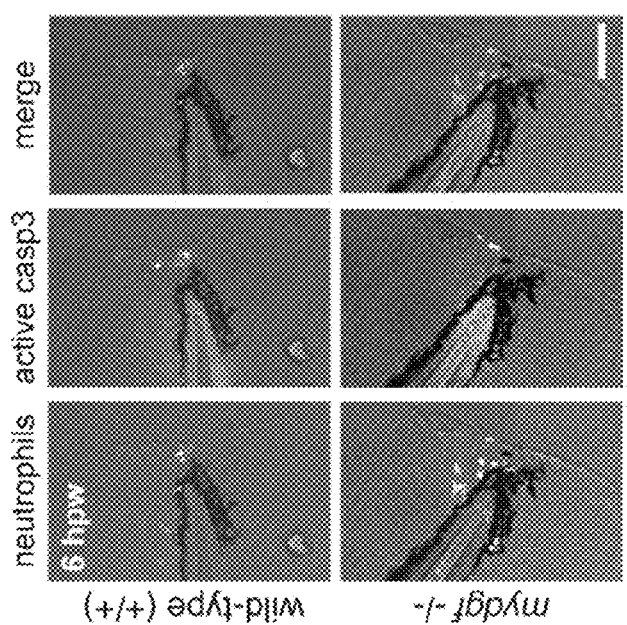
Fig. 6G  Fig. 6H  Fig. 6I

SEQUENCE LISTING

```
<160> NUMBER OF SEQ ID NOS: 24

<210> SEQ ID NO 1
<211> LENGTH: 173
<212> TYPE: PRT
<213> ORGANISM: Homo sapiens
<220> FEATURE:
<221> NAME/KEY: misc_feature
<223> OTHER INFORMATION: MYDGF Amino Acid Sequence, Human (UniProtKB -
      Q969H8):
<220> FEATURE:
<221> NAME/KEY: SIGNAL
<222> LOCATION: (1)..(31)
<220> FEATURE:
<221> NAME/KEY: mat_peptide
<222> LOCATION: (32)..(173)

<400> SEQUENCE: 1
```

```
Met Ala Ala Pro Ser Gly Gly Trp Asn Gly Val Gly Ala Ser Leu Trp
    -30             -25                 -20

Ala Ala Leu Leu Leu Gly Ala Val Ala Leu Arg Pro Ala Glu Ala Val
-15             -10                  -5                  -1   1

Ser Glu Pro Thr Thr Val Ala Phe Asp Val Arg Pro Gly Gly Val Val
             5                  10                  15

His Ser Phe Ser His Asn Val Gly Pro Gly Asp Lys Tyr Thr Cys Met
             20                  25                  30

Phe Thr Tyr Ala Ser Gln Gly Gly Thr Asn Glu Gln Trp Gln Met Ser
             35                  40                  45

Leu Gly Thr Ser Glu Asp His Gln His Phe Thr Cys Thr Ile Trp Arg
50               55                  60                      65

Pro Gln Gly Lys Ser Tyr Leu Tyr Phe Thr Gln Phe Lys Ala Glu Val
                 70                  75                  80

Arg Gly Ala Glu Ile Glu Tyr Ala Met Ala Tyr Ser Lys Ala Ala Phe
             85                  90                  95

Glu Arg Glu Ser Asp Val Pro Leu Lys Thr Glu Glu Phe Glu Val Thr
             100                 105                 110

Lys Thr Ala Val Ala His Arg Pro Gly Ala Phe Lys Ala Glu Leu Ser
             115                 120                 125

Lys Leu Val Ile Val Ala Lys Ala Ser Arg Thr Glu Leu
130                 135                 140

<210> SEQ ID NO 2
<211> LENGTH: 990
<212> TYPE: DNA
<213> ORGANISM: Homo sapiens
<220> FEATURE:
<221> NAME/KEY: misc_feature
<223> OTHER INFORMATION: NCBI Reference Sequence: NM_019107.4

<400> SEQUENCE: 2
agtccaacat ggcggcgccc agcggagggt ggaacggcgt cggcgcgagc ttgtgggccg      60
cgctgctcct aggggccgtg gcgctgaggc cggcggaggc ggtgtccgag cccacgacgg     120
tggcgtttga cgtgcggccc ggcggcgtcg tgcattcctt ctcccataac gtgggcccgg     180
gggacaaata tacgtgtatg ttcacttacg cctctcaagg agggaccaat gagcaatggc     240
agatgagtct ggggaccagc gaagaccacc agcacttcac ctgcaccatc tggaggcccc     300
aggggaagtc ctatctgtac ttcacacagt tcaaggcaga ggtgcgggc gctgagattg      360 agtacgccat ggcctactct aaagccgcat ttgaaaggga aagtgatgtc cctctgaaaa     420
ctgaggaatt tgaagtgacc aaaacagcag tggctcacag gcccggggca ttcaaagctg     480
agctgtccaa gctggtgatt gtggccaagg catcgcgcac tgagctgtga ccagcagccc     540
tgttgcgggt ggcaccttct catctccggt gaagctgaag gggcctgtgt ccctgaaagg     600
gccagcacat cactggtttt ctaggaggga ctcttaagtt ttctacctgg gctgacgttg     660
ccttgtccgg aggggcttgc agggtggctg aagccctggg gcagagaaca gagggtccag     720
ggccctcctg gctcccaaca gcttctcagt tcccacttcc tgctgagctc ttctggactc     780
aggatcgcag atccggggca caagagggt ggggaacatg ggggctatgc tggggaaagc      840
agccatgctc cccccgacct ccagccgagc atccttcatg agcctgcaga actgctttcc     900
tatgtttacc caggggacct cctttcagat gaactgggaa gagatgaaat gttttttcat     960
atttaaataa ataagaacat taaaaagcaa                                      990
```

<210> SEQ ID NO 3
<211> LENGTH: 166
<212> TYPE: PRT
<213> ORGANISM: Mus musculus
<220> FEATURE:
<221> NAME/KEY: misc_feature
<223> OTHER INFORMATION: MYDGF Amino Acid Sequence, Mouse (UniProtKB - Q9CPT4)

<400> SEQUENCE: 3

Met Ala Ala Pro Ser Gly Gly Phe Trp Thr Ala Val Val Leu Ala Ala
1               5                   10                  15

Ala Ala Leu Lys Leu Ala Ala Ala Val Ser Glu Pro Thr Thr Val Pro
            20                  25                  30

Phe Asp Val Arg Pro Gly Gly Val Val His Ser Phe Ser Gln Asp Val
        35                  40                  45

Gly Pro Gly Asn Lys Phe Thr Cys Thr Phe Thr Tyr Ala Ser Gln Gly
    50                  55                  60

Gly Thr Asn Glu Gln Trp Gln Met Ser Leu Gly Thr Ser Glu Asp Ser
65                  70                  75                  80

Gln His Phe Thr Cys Thr Ile Trp Arg Pro Gln Gly Lys Ser Tyr Leu
                85                  90                  95

Tyr Phe Thr Gln Phe Lys Ala Glu Leu Arg Gly Ala Glu Ile Glu Tyr
            100                 105                 110

Ala Met Ala Tyr Ser Lys Ala Ala Phe Glu Arg Glu Ser Asp Val Pro
        115                 120                 125

Leu Lys Ser Glu Glu Phe Glu Val Thr Lys Thr Ala Val Ser His Arg
    130                 135                 140

Pro Gly Ala Phe Lys Ala Glu Leu Ser Lys Leu Val Ile Val Ala Lys
145                 150                 155                 160

Ala Ala Arg Ser Glu Leu
                165

<210> SEQ ID NO 4
<211> LENGTH: 160
<212> TYPE: PRT
<213> ORGANISM: Mus musculus
<220> FEATURE:
<221> NAME/KEY: misc_feature
<223> OTHER INFORMATION: NCBI Reference Sequence: NM_080837.2 (Mouse MYDGF)

<400> SEQUENCE: 4

Met Ala Ala Pro Ser Gly Gly Phe Trp Thr Ala Val Val Leu Ala Ala
1               5                   10                  15

Ala Ala Leu Lys Leu Ala Ala Ala Val Ser Glu Pro Thr Thr Val Pro
            20                  25                  30

Phe Asp Val Arg Pro Gly Gly Val Val His Ser Phe Ser Gln Asp Val
        35                  40                  45

Gly Pro Gly Asn Lys Phe Thr Cys Thr Phe Thr Tyr Ala Ser Gln Gly
    50                  55                  60

Gly Thr Asn Glu Gln Trp Gln Met Ser Leu Gly Thr Ser Glu Asp Ser
65                  70                  75                  80

Gln His Phe Thr Cys Thr Ile Trp Arg Pro Gln Gly Lys Ser Tyr Leu
                85                  90                  95

Tyr Phe Thr Gln Phe Lys Ala Glu Leu Arg Gly Ala Glu Ile Glu Tyr
            100                 105                 110

Ala Met Ala Tyr Ser Lys Ala Ala Phe Glu Arg Glu Ser Asp Val Pro

```
                115                 120                 125
Leu Lys Ser Glu Glu Phe Glu Val Thr Lys Thr Ala Val Ser His Arg
            130                 135                 140

Pro Gly Ala Phe Lys Ala Glu Leu Ser Lys Leu Val Ile Val Ala Lys
145                 150                 155                 160

<210> SEQ ID NO 5
<211> LENGTH: 6
<212> TYPE: PRT
<213> ORGANISM: Mus musculus
<220> FEATURE:
<221> NAME/KEY: misc_feature
<223> OTHER INFORMATION: Signal peptide for mouse MYDGF gene

<400> SEQUENCE: 5

Ala Ala Arg Ser Glu Leu
1               5

<210> SEQ ID NO 6
<211> LENGTH: 913
<212> TYPE: DNA
<213> ORGANISM: Mus musculus

<400> SEQUENCE: 6
gagcgcctgc gcattgcccc ggaagcaaga tggcagcccc cagcggaggc ttctggactg     60
cggtggtcct ggcggccgca gcgctgaaat tggccgccgc tgtgtccgag cccaccaccg    120
tgccatttga cgtgaggccc ggaggggtcg tgcattcgtt ctcccaggac gtaggacccg    180
ggaacaagtt tacatgtaca ttcacctacg cttcccaagg agggaccaac gagcaatggc    240
agatgagcct ggggacaagt gaagacagcc agcactttac ctgtaccatc tggaggcccc    300
aggggaaatc ctacctctac ttcacacagt tcaaggctga gttgcgaggt gctgagatcg    360
agtatgccat ggcctactcc aaagccgcat tgagagagag gagtgatgtc cccctgaaaa    420
gtgaggagtt tgaagtgacc aagacagcag tgtctcacag gcctgggccc ttcaaagctg    480
agctctccaa gctggtgatc gtagccaagg cggcacgctc ggagctgtga ccctcgcctg    540
tcaagggcct tcatgtccac gttcctcagg cacactgacc gggactactt gtctagggca    600
ctggttccca taggagctgc cctgccctgc acaggtcaca ctgtgtcact ccgcagaact    660
ctctgagccc ggtcacctgt tttgccaggg aagatgcagg gcatgtgcgg gggtgggatg    720
gaaggacttc ctggctttcc tgaagtcaag atgtggtgtg gtttcccctc tgagccacag    780
atgagtgtcc ccatcccagg accactttct aaccccatcc agggcagctc cactcagaag    840
gatgggaaag gatagaaaaa ataaataaat aagtagccac cttagtggtg gctctgtggg    900
gtcaggactc aga                                                      913

<210> SEQ ID NO 7
<211> LENGTH: 164
<212> TYPE: PRT
<213> ORGANISM: Danio rerio
<220> FEATURE:
<221> NAME/KEY: misc_feature
<223> OTHER INFORMATION: MYDGF Amino Acid Sequence, Zebrafish
      (UniProtKB - A7MCH1)

<400> SEQUENCE: 7

Met Ala Phe Ile Val His Met Lys Trp Phe Val Asn Leu Leu Leu Leu
1               5                   10                  15

Phe Val Val Leu Cys Glu Leu Cys Ser Ala Glu Arg Thr Lys Thr Leu
            20                  25                  30
```

Asp Phe Asp Val Lys Pro Gly Gly Val Val Gln Thr Phe Ser Ala Lys
    35                  40                  45

Leu Lys Lys Tyr Lys Cys Thr Phe Thr Tyr Ala Cys Gln Gly Gly Thr
 50                  55                  60

Asn Glu Gln Trp Gln Met Ser Val Gly Leu Ser Asp Asp Glu Gln Met
 65                  70                  75                  80

Phe Ser Cys Ser Val Trp Arg Pro Gln Gly Lys Ser Tyr Leu Phe Phe
                 85                  90                  95

Thr Gln Phe Lys Ala Glu Ile Lys Gly Ala Lys Ile Glu Tyr Ala Thr
                100                 105                 110

Ala Tyr Ser Gln Thr Ala Val Gly Gly Gln Arg Asp Val Ala Leu Lys
            115                 120                 125

Glu Glu Glu Tyr Ile Val Ser Glu Ser Ala Val Thr Gln Arg Asp Gly
        130                 135                 140

Lys Phe His Ser Glu Leu Ser Lys Leu Thr Val Ile Gly Arg Ile Arg
145                 150                 155                 160

His Asp Glu Leu

<210> SEQ ID NO 8
<211> LENGTH: 1473
<212> TYPE: DNA
<213> ORGANISM: Danio rerio

<400> SEQUENCE: 8

```
atcctatgaa gaacatacag gaacagtaca ggcacctttt tcattcacaa cataaacgca      60
gatctcctgt ctgtaaagca tcatggcatt tattgtgcac atgaaatggt ttgtgaatct     120
tctgctgctg tttgttgtgc tttgtgaact gtgttctgct gaaaggacca aaacactgga     180
cttcgatgtc aaacctggag gagttgtgca gactttctct gcaaaactta agaagtataa     240
atgcaccttc acatatgcat gccaaggagg aaccaatgag caatggcaaa tgagtgtcgg     300
actaagtgac gatgagcaaa tgttttcctg ttcagtatgg aggccccaag ggaagtccta     360
cttgtttttt acgcagttca aagccgagat aaaaggagcc aagatcgagt acgccaccgc     420
atattcccag acggccgtgg gtggacagag ggatgttgct ttgaaagaag aagagtacat     480
agtgtcagag tctgcagtga cacaaagaga tggaaaattc cattcggagc tttctaagct     540
cactgtcatt ggtcgaatac ggcatgatga actctgattg gccgattcga aggacgttgg     600
ttatttaaca gctttggaca caattttctg ctcacggtca taagtcaagc gaaggaaatc     660
acagcactgg acattctgaa aaatgaattt accgtgatag aaaagatttc ctatagatgc     720
cagtggccaa aggttggagt gatcatcaga ggtagacgaa agtctatta ttggatatta      780
taaggggtaa aacaaattgt acatgcgcat tttttcata tttgtaaggt gttataaagt      840
cttctttata ttcagtgcag aacagcagat tgatttctgt tcttgtcaga atttatgggt     900
tttctagggt tacagtctga ctttgattca tacctgcaaa gctgattatc aagagtgctc     960
atacttactt tcctaggctg gtgtaaaggc acgcttgtag acaattccca ctaaatcttt    1020
ggggtgtgtt agaatccttt gagtatttct gtggtggagg aaaaaacatc aagttggtta    1080
ctacagttcc ttttgtctcc cagtcatgct ttattctgat aaccgatgta tcggaatttg    1140
aataaatctg ttatcagaac aatttgactt ctggccttac tatttgctga cttgtatac     1200
ctaatatttt tgcgtaaagt aagtgaattg tgtctgttta aaagcaacaa cctctgaggg    1260
ctgttttttt tgcactctta agggtgaaaa atgtgtgtaa ttctgctgca taaaattaaa    1320
```

```
ataagctaca aatttgctga ttctgttcaa gatttgtcca gtcagctctt taaaaggctt    1380
gtcggtaccc caactgtgaa taaaagagcc tgcaatgcaa ttcacaagct attaaagaaa    1440
ttaatgtctt gagaaccaaa aaaaaaaaaa aaa                                 1473

<210> SEQ ID NO 9
<211> LENGTH: 20
<212> TYPE: DNA
<213> ORGANISM: Artificial Sequence
<220> FEATURE:
<223> OTHER INFORMATION: Amplification Primer

<400> SEQUENCE: 9
cccaagggaa gtcctacttg                                                  20

<210> SEQ ID NO 10
<211> LENGTH: 20
<212> TYPE: DNA
<213> ORGANISM: Artificial Sequence
<220> FEATURE:
<223> OTHER INFORMATION: Amplification Primer

<400> SEQUENCE: 10
agcaacatcc ctctgtccac                                                  20

<210> SEQ ID NO 11
<211> LENGTH: 18
<212> TYPE: DNA
<213> ORGANISM: Artificial Sequence
<220> FEATURE:
<223> OTHER INFORMATION: Amplification Primer

<400> SEQUENCE: 11
cgctgcgtca cctgtatt                                                    18

<210> SEQ ID NO 12
<211> LENGTH: 20
<212> TYPE: DNA
<213> ORGANISM: Artificial Sequence
<220> FEATURE:
<223> OTHER INFORMATION: Amplification Primer

<400> SEQUENCE: 12
tagcatacga cggctgaact                                                  20

<210> SEQ ID NO 13
<211> LENGTH: 20
<212> TYPE: DNA
<213> ORGANISM: Artificial Sequence
<220> FEATURE:
<223> OTHER INFORMATION: Amplification Primer

<400> SEQUENCE: 13
tgccttcgtc ccaatttcag                                                  20

<210> SEQ ID NO 14
<211> LENGTH: 20
<212> TYPE: DNA
<213> ORGANISM: Artificial Sequence
<220> FEATURE:
<223> OTHER INFORMATION: Amplification Primer

<400> SEQUENCE: 14
taccctcctt gcgctcaatc                                                  20
```

```
<210> SEQ ID NO 15
<211> LENGTH: 25
<212> TYPE: DNA
<213> ORGANISM: Artificial Sequence
<220> FEATURE:
<223> OTHER INFORMATION: Amplification Primer

<400> SEQUENCE: 15
gagtgtataa gttacctcca tactg                                        25

<210> SEQ ID NO 16
<211> LENGTH: 25
<212> TYPE: DNA
<213> ORGANISM: Artificial Sequence
<220> FEATURE:
<223> OTHER INFORMATION: Amplification Primer

<400> SEQUENCE: 16
ggaatagcat atacgcatgc tcacc                                        25

<210> SEQ ID NO 17
<211> LENGTH: 25
<212> TYPE: DNA
<213> ORGANISM: Artificial Sequence
<220> FEATURE:
<223> OTHER INFORMATION: Amplification Primer

<400> SEQUENCE: 17
cctcttacct cagttacaat ttata                                        25

<210> SEQ ID NO 18
<211> LENGTH: 25
<212> TYPE: DNA
<213> ORGANISM: Artificial Sequence
<220> FEATURE:
<223> OTHER INFORMATION: Amplification Primer

<400> SEQUENCE: 18
ggattagctg atgtcatgtc cgaca                                        25

<210> SEQ ID NO 19
<211> LENGTH: 17
<212> TYPE: DNA
<213> ORGANISM: Artificial Sequence
<220> FEATURE:
<223> OTHER INFORMATION: Amplification Primer

<400> SEQUENCE: 19
ggccgtgggt ggacagg                                                 17

<210> SEQ ID NO 20
<211> LENGTH: 38
<212> TYPE: DNA
<213> ORGANISM: Artificial Sequence
<220> FEATURE:
<223> OTHER INFORMATION: Amplification Primer

<400> SEQUENCE: 20
gtaaaacgac ggccagtgtg acattgacat ttgccgca                          38

<210> SEQ ID NO 21
<211> LENGTH: 22
<212> TYPE: DNA
<213> ORGANISM: Artificial Sequence
<220> FEATURE:
<223> OTHER INFORMATION: Amplification Primer
```

```
<400> SEQUENCE: 21
agactctgac actatgtact ct                                            22

<210> SEQ ID NO 22
<211> LENGTH: 37
<212> TYPE: DNA
<213> ORGANISM: Artificial Sequence
<220> FEATURE:
<223> OTHER INFORMATION: Amplification Primer

<400> SEQUENCE: 22
ctgtgtggta ccgaaaggac caaaacactg gacttcg                            37

<210> SEQ ID NO 23
<211> LENGTH: 38
<212> TYPE: DNA
<213> ORGANISM: Artificial Sequence
<220> FEATURE:
<223> OTHER INFORMATION: Amplification Primer

<400> SEQUENCE: 23
tagagggcta gctcagagtt catcatgccg tattcgac                           38

<210> SEQ ID NO 24
<211> LENGTH: 21
<212> TYPE: PRT
<213> ORGANISM: Artificial Sequence
<220> FEATURE:
<223> OTHER INFORMATION: N-terminal polyhistidine tag and thrombin
      cleavage site

<400> SEQUENCE: 24

Met Gly Gly Ser His His His His His His Gly Ser Leu Val Pro Arg
1               5                   10                  15

Gly Ser Lys Gly Thr
            20
```

METHOD TO INHIBIT NEUTROPHIL RECRUITMENT TO DAMAGED TISSUE USING MYELOID-DERIVED GROWTH FACTOR

CROSS-REFERENCE TO RELATED APPLICATIONS

Priority is hereby claimed to provisional application Ser. No. 63/081,664, filed Sep. 22, 2020, which is incorporated herein by reference.

FEDERAL FUNDING STATEMENT

This invention was made with government support under GM118027 awarded by the National Institutes of Health. The government has certain rights in the invention.

BACKGROUND

Human myeloid-derived growth factor (hMYDGF) is a member of the widely distributed MYDGF family of proteins found in organisms as distant as protozoans. In humans, MYDGF is abundant in nearly 200 different tissues, fluids, and cell lines as compiled by Proteomics DB, a repository of quantitative proteomics data. hMYDGF comprises a 31-residue signal sequence followed by a 142-residue mature protein ending in C-terminal residues RTEL. (See SEQ. ID. NO.1.) The three-dimensional solution structure of human MYDGF has been elucidated via $^{13}$C and $^{15}$N NMR. Removal of the C-terminal Glu-Leu residues from hMYDGF exogenously expressed in HEK293 cells demonstrated that absence or presence of an intact endoplasmic reticulum retention sequence determines, in a nearly all-or-none fashion, whether hMYDGF is retained in the endoplasmic reticulum or secreted. See Bortnov et al. (2019) "Solution structure of human myeloid-derived growth factor suggests a conserved function in the endoplasmic reticulum," *Nature Communications* 10:5612.

MYDGF is known to mediate cardiac repair following myocardial infarction by inhibiting cardiac myocyte apoptosis (which acts to reduce the infarct size). See Korf-Klingebiel et al. (2015) "Myeloid-derived growth factor (C19orf10) mediates cardiac repair following myocardial infarction" *Nature Medicine* 21:140-149. This 2015 study found that Mydgf-deficient mice developed larger infarct scars and more severe contractile dysfunction compared to wild-type mice. Treating the mice with recombinant MYDGF reduced scar size and contractile dysfunction after myocardial infarction.

It has also been shown in a mouse model that MYDGF functions to maintain glucose homeostasis by inducing glucagon-like peptide-1 (GLP-1) production and secretion. Increased levels of MYDGF improved glucose tolerance and lipid metabolism. See Wang et al. (2020) "Myeloid-Derived Growth Factor Promotes Intestinal Glucagon-Like Peptide-1 Production in Male Mice with Type 2 Diabetes," *Endocrinology* 1(2):161.

A mutant mouse in which the gene encoding MYDGF has been disabled (a conditional knock out mutant) is available commercially from Shanghai Model Organisms (1820, 29th Ave, San Francisco, California, 94122 USA);
Strain Name: B6; 129-Mydgf$^{tm1(flox)Smoc}$
Cat. No: NM-CKO-00021
Gene Symbol: Mydgf
Gene Synonyms: D17Wsu104e, I125, Ly6elg
Human Ortholog: MYDGF
Ensembl ID: ENSMUSG00000019579
MGI ID: 2156020
NCBI ID: 28106

SUMMARY

Disclosed herein is a method to inhibit neutrophil recruitment to damaged tissue in a subject, the method comprising administering to a subject, the subject having a wound and/or a burn at a site on the subject, an amount of a myeloid-derived growth factor ("MYDGF"), a biologically active fragment thereof, an analogous sequence thereof, or a pharmaceutically suitable salt of any of the foregoing, wherein the amount is effective to inhibit neutrophil recruitment to the wound and/or burn site.

In some embodiments, the MYDGF has an amino acid sequence having at least 60% sequence identity, at least 70% sequence identity, at least 80% sequence identity, at least 90% sequence identity, at least 95% sequence, or at least 99% identity to the mature proteins shown in any of SEQ. ID. NOS:1, 3, or 7.

Also disclosed herein is a method to inhibit inflammation in a subject, the method comprising administering to the subject an anti-inflammatory-effective amount of a myeloid-derived growth factor ("MYDGF"), a biologically active fragment thereof, an analogous sequence thereof, or a pharmaceutically suitable salt of any of the foregoing.

In some embodiments the MYDGF has an amino acid sequence having at least 60% sequence identity, at least 70% sequence identity, at least 80% sequence identity, at least 90% sequence identity, at least 95% sequence, or at least 99% identity to the mature proteins shown in any of SEQ. ID. NOS:1, 3, or 7.

Also disclosed herein is a method to promote wound healing in a subject, the method comprising administering to the subject an amount of a myeloid-derived growth factor ("MYDGF"), a biologically active fragment thereof, an analogous sequence thereof, or a pharmaceutically suitable salt of any of the foregoing, wherein the amount is effective to promote wound healing in the subject.

In some embodiments, the MYDGF has an amino acid sequence having at least 60% sequence identity, at least 70% sequence identity, at least 80% sequence identity, at least 90% sequence identity, at least 95% sequence, or at least 99% identity to the mature proteins shown in any of SEQ. ID. NOS:1, 3, or 7.

In some embodiments, the MYDGF is administered to a vertebrate subject.

In some embodiments, the MYDGF is administered to a mammalian subject.

In some embodiments, the MYDGF is administered to a human subject.

Also disclosed herein is a pharmaceutical composition comprising myeloid-derived growth factor ("MYDGF"), a biologically active fragment thereof, or an analogous sequence thereof, in an amount effective to inhibit neutrophil recruitment to a wound or burn site in a subject administered the composition, in combination with a pharmaceutically suitable carrier.

Also disclosed herein is a pharmaceutical composition comprising myeloid-derived growth factor ("MYDGF"), a biologically active fragment thereof, or an analogous sequence thereof, in an amount effective to inhibit inflammation in a subject administered the composition, in combination with a pharmaceutically suitable carrier.

Also disclosed herein is a pharmaceutical composition comprising myeloid-derived growth factor ("MYDGF"), a biologically active fragment thereof, or an analogous sequence thereof, in an amount effective to promote wound healing in a subject administered the composition, in combination with a pharmaceutically suitable carrier.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Expression of mydgf, measured by RNA sequencing (fragments per kilobase of transcript per million mapped reads [fpkm]), in three cell types is displayed 3 h following multiple wounding along the tail fin tissue. Each dot represents one independent replicate. Sample preparation and RNA-sequencing dataset was published previously (Houseright et al., 2020). (FIGS. 1B and 1C) RT-qPCR measurement of mydgf expression in WT zebrafish tails 3 h following tail transection (Tt) or tail burn wound (burn; FIG. 1B) and P. aeruginosa (Pa; FIG. 1C) otic infection at 2 h after infection. Data comprise three (burn and infection) to five (Tt) independent experiments performed in technical triplicates and are normalized to mydgf-expression in unwounded (Unwnd) tails and to ef1α. n=50 tails per condition per independent replicate. *, P<0.05. Fold changes in gene expression were compared with the normalized value of 1 using one-sample t tests. Data are displayed as mean with 95% CI.

FIGS. 2A-2I. MYDGF regulates neutrophil response to tissue damage, but not infection. (FIG. 2A) Ribbon and surface representation of the human MYDGF NMR solution structure (PDB accession no. 6O6W). Residues identical in zebrafish MYDGF are shown in red. (FIG. 2B) Schematic of zebrafish mydgf gene, with exon 5 gRNA sequences highlighted for CRISPR-Cas9 mutagenesis. gRNA sequence is shown in gray and protospacer adjacent motif is shown in magenta; scale bar=100 bp. (FIG. 2C) Exon 5 DNA sequence of WT (top) and mydgf$^{-/-}$ (bottom) zebrafish mutants showing a 12-bp deletion. (FIG. 2D) Representative Western blot for zebrafish MYDGF and β-tubulin from pooled 3 dpf zebrafish larvae. Data are representative of three independent replicates. Size marker (mol wt [MW]) in left lane. (FIG. 2E) InstantBlue stain of 12% SDS-PAGE of zebrafish MYDGF in CCM by HEK293 cells at 72 h after transfection by empty or zebrafish MYDGF-expressing pCS2 constructs. (FIGS. 2F and 2G) Representative images (FIG. 2F) and quantification (FIG. 2G) of mCherry-labeled neutrophils at the otic vesicle of WT or mydgf$^{-/-}$ larvae, following microinjection with CCM±zebrafish MYDGF protein at 2 h after injection; three independent replicates with n=29+/+ control, 32+/+ zebrafish MYDGF, 54-/- control and 52-/- zebrafish MYDGF; scale bar=50 μm. (FIGS. 2H and 2I) Otic vesicle of 3 dpf WT or mydgf$^{-/-}$ zebrafish larvae were microinjected with P. aeruginosa (Pa; 5000 CFU), followed by fixation at 2 h after injection. Neutrophils are visualized by Sudan Black staining. In FIGS. 2H and 2I, representative brightfield images (FIG. 2H) and quantification (FIG. 2I) of the number of neutrophils at the otic vesicle are shown; three independent replicates with n=43+/+ and 57-/-; scale bar=100 μm. In FIGS. 2G and 2I, data are expressed as mean with 95% CI; each symbol represents one larva, and different colors represent independent replicates. ****, P<0.0001. P values were calculated by ANOVA with Tukey's multiple comparisons. Ctrl, control; hpi, h postinjection; zMYDGF, zebrafish MYDGF.

(FIG. 3A) Caudal fins of 3 dpf WT or mydgf$^{-/-}$ zebrafish larvae with mCherry-labeled neutrophils were wounded by thermal injury and fixed at 3 and 24 hpb. Neutrophils were counted in the burn area. (FIGS. 3A and 3B) Representative images (FIG. 3A) and quantification (FIG. 3B) of neutrophils in the burn are shown; three independent replicates with n=24+/+ and 24-/- at 3 hpb and 21+/+ and 16-/- at 24 hpb; scale bar=100 μm. (FIGS. 3C-3F) Caudal fins of 2 dpf (for morpholinos) or 3 dpf (for all other experiments) larvae were wounded by thermal injury and fixed at 24, 48, and 72 hpb. Wound healing was determined by quantifying the area of tail fin regrowth, measured from the caudal arteriovenous loop to the wound edge. (FIGS. 3C and 3D) Representative brightfield images (FIG. 3C) and quantification (FIG. 3D) of tail fin regrowth area in WT and mydgf$^{-/-}$ larvae are shown; two independent replicates with n=45+/+ and 51-/- at 24 hpb, 46+/+ and 48-/- at 48 hpb, and 41+/+ and 47-/- at 72 hpb; scale bar=100 μm. (FIGS. 3E and 3F) Representative brightfield images (FIG. 3E) and quantification (FIG. 3F) of tail fin regrowth area in WT (WT Rac2) or neutrophil motility-impaired (Rac2D57N) larvae, with or without mydgf-targeting morpholino #1, at 24 hpb; three independent replicates with n=50 WT/control mo, 32 WT/mydgf mo, 48 D57N/control mo, and 32 D57N/mydgf mo; scale bar=100 μm. In FIGS. 3B, 3D, and 3F, data are expressed as mean with 95% CI; each symbol represents one larva, and different colors represent independent replicates. *, P<0.05; , P<0.01; **, P<0.0001. P values were calculated by ANOVA with Tukey's multiple comparisons.

FIGS. 4A-4H. Morpholino-mediated depletion of MYDGF phenocopies neutrophil accumulation at sterile injury observed in mydgf homozygous mutant. (FIG. 4A) Quantification of the tail length of unwounded WT and mydgf$^{-/-}$ larvae at 6 dpf; two independent replicates with n=13+/+ and 10-/-. (FIG. 4B) Schematic of zebrafish mydgf gene, with sequences targeted by splice-blocking morpholinos #1 and #2 highlighted at the junction of exon 3 and intron 3 and the junction of exon 5 and intron 5, respectively; scale bar=100 bp. (FIG. 4C) Representative Western blot for zebrafish MYDGF and β-actin from pooled, 2 dpf larvae treated with either mismatch control mo or mo targeting mydgf. (FIG. 4D) Quantification of Western blot in FIG. 4C; representative of three independent replicates. (FIGS. 4E-4G) Representative brightfield images of Sudan Black staining (FIG. 4E) and quantification of the number of neutrophils in the wound microenvironment of larvae treated with either mismatch control mo and mydgf-targeting mo #1 (FIG. 4F) or mo #2 (FIG. 4G) at 1 and 6 hpw following tail transection of the caudal fin; three independent replicates with n=52 control and 52 mo #1 at 1 hpw and 53 control and 34 mo #1 at 6 hpw (FIG. 4F), and three independent replicates with n=47 control and 51 mo #2 at 1 hpw and 44 control and 58 mo #2 at 6 hpw (FIG. 4G); scale bar=100 μm. (FIG. 4H) Quantification of the total number of neutrophils in 3 dpf whole larvae treated with mismatch control or mo #1 targeting mydgf; three independent replicates with n=59 control and 57 mo #1. For FIGS. 4F-4H, data are expressed as mean with 95% CI; each symbol represents one larva, and different colors represent the results of three independent replicates. *, P<0.001; **, P<0.0001. P values were calculated by ANOVA with Tukey's multiple comparisons.

FIGS. 5A-5F. MYDGF depletion alters neutrophil motility in the wound microenvironment. (FIG. 5A) Caudal fins of 3 dpf WT or mydgf$^{-/-}$ zebrafish larvae with mCherry-labeled neutrophils were wounded by tail transection, and fixed at 1 and 6 hpw. Neutrophils were counted at the wound, distal to the tip of the notochord. (FIGS. 5A and 5B) Representative images (FIG. 5A) and quantification (FIG. 5B) of neutrophils in the wound are shown; three independent replicates with n=27+/+ and 20−/− at 1 hpw and 42+/+ and 37−/− at 6 hpw; scale bar=100 μm. (FIG. 5C) Quantification of total number of mCherry-labeled neutrophils in 3 dpf WT and mydgf$^{-/-}$ whole larvae; three independent replicates with n=55 WT and 58−/−. In FIGS. 5B and 5C, data are expressed as mean with 95% CI; each symbol represents one larva, and different colors represent independent replicates. *, P<0.05; ***, P<0.001. P values were calculated by ANOVA with Tukey's multiple comparisons. (FIG. 5D) Representative serial images from time-lapse imaging 0-6 h following tail transection of the caudal fin of WT and mydgf$^{-/-}$ larvae. Lines represent neutrophil tracks over time, with warmer colors indicating a longer time since track start; four independent replicates with n=7+/+ and 11−/− larvae; scale bar=100 μm. (FIG. 5E) Quantification of the number of neutrophils at the wound microenvironment over the course of time-lapse imaging. (FIG. 5F) Quantification of the instantaneous speed during the later phase (3-6 hpw) of neutrophil recruitment; 0 min represents the time at which each neutrophil enters the wound microenvironment.

FIGS. 6A-6I. MYDGF depletion impairs neutrophil reverse migration and resolution following injury. (FIGS. 6A and 6B) Representative images (FIG. 6A) and quantification (FIG. 6B) of green (total) and red (photoconverted) dendra2-labeled neutrophils in the wound microenvironment at 6 hpw following tail transection of 3 dpf WT and mydgf$^{-/-}$ larvae; three independent replicates with n=33+/+ and 36−/−; scale bar=100 μm. (FIG. 6C) Quantification of the percentage of photoconverted neutrophils present at the wound at 2 hpw that are no longer present at 6 hpw in the same larva. (FIGS. 6D and 6E) Representative images (FIG. 6D) and quantification (FIG. 6E) of green (total) and red (photoconverted) dendra2-labeled neutrophils in the burn at 24 hpb following thermal injury of the caudal fin of 3 dpf WT and mydgf$^{-/-}$ larvae; three independent replicates with n=20+/+ and 15−/−; scale bar=100 μm. (FIG. 6F) Quantification of the percentage of photoconverted neutrophils present in the burn microenvironment at 3 hpb that are no longer present at 24 hpb in the same larva. (FIG. 6G) Representative images of immunostaining for active caspase-3 (casp3) following tail transection of 3 dpf WT and mydgf$^{-/-}$ larvae with mCherry-labeled neutrophils at 6 hpw; scale bar=100 μm. (FIG. 6H) Quantification of total and active caspase-3-expressing neutrophils in the wound at 6 hpw; three independent replicates with n=42+/+ and 71−/−. (FIG. 6I) Proportion of neutrophils in the wound expressing active caspase-3 at 6 hpw. In FIGS. 6B, 6C, 6E, 6F, 6H, and 6I, data are expressed as mean with 95% CI; each symbol represents one larva, and different colors represent the results of three independent replicates. *, P<0.05; , P<0.01; *, P<0.001. P values were calculated by ANOVA with Tukey's multiple comparisons.

(FIGS. 7A and 7B) Representative brightfield images (FIG. 7A) and quantification (FIG. 7B) of tail fin regrowth area following thermal injury of the caudal fin of larvae microinjected at the posterior caudal vein with PBS or clodronate liposomes (Cld); three independent replicates with n=48 PBS and 49 clodronate liposomes at 1 d postburn (dpb), 47 PBS and 47 clodronate liposomes at 2 dpb, 46 PBS and 47 clodronate liposomes at 3 dpb, and 44 PBS and 45 clodronate liposomes at 4 dpb; scale bar=100 μm. P values were calculated by unpaired two-tailed t test; *, P<0.05. (FIG. 7C) Quantification of the number of macrophages at the wound microenvironment at 4 and 24 hpw following tail transection of the caudal fin of 3 dpf WT and mydgf−/− larvae; three independent replicates with n=21+/+ and 30−/− at 4 hpw, 20+/+ and 38−/− at 24 hpw. P values were calculated by ANOVA with Tukey's multiple comparisons. (FIG. 7D) Quantification of the number of physical contact between neutrophils and macrophages at the wound microenvironment over the course of time-lapse imaging following tail transection of the caudal fin of 3 dpf WT and mydgf$^{-/-}$ larvae; four independent replicates with n=7+/+ and 11−/− larvae. (FIGS. 7E and 7F) Quantification of the number of macrophages (FIG. 7E) and the number of physical contacts between neutrophils and macrophages (FIG. 7F) at the burn microenvironment over the course of time-lapse imaging following thermal injury of the caudal fin of 3 dpf WT and mydgf$^{-/-}$ larvae; three independent replicates with n=10+/+ and 10−/− larvae. The number of contacts displayed in FIGS. 7D and 7F are adjusted values, where the raw number of contacts was multiplied by the number of neutrophils and normalized to number of macrophages at each frame. No statistical differences were detected, as calculated by unpaired two-tailed t test. In FIGS. 7B and 7C, data are expressed as mean with 95% CI; each symbol represents one larva, and different colors represent the results of three independent replicates.

(FIG. 8A) Schematic representation of HIF-1α activation in neutrophils. Pathway activation results in neutrophil persistence and survival and is characterized by increased expression of phd3. HIF-1α pathway activation can be blocked at the level of transcription factor nuclear binding using arnt-1 morpholino. Illustration was created at www.biorender.com. (FIG. 8B) phd3 expression in pooled tail fin tissue collect from WT larvae, either unwounded or 3 h following tail transection (Tt) or thermal injury (burn), measured by RT-qPCR. Data comprise three (burn) to five (Tt) independent replicates performed in technical triplicates and normalized to mydgf expression in unwounded tails and to ef1α. n=50 tails per condition per independent replicate. *, P<0.05. Fold changes in gene expression were compared with the normalized value of 1 using one-sample t tests. (FIGS. 8C and 8D) Representative images (FIG. 8C) and quantification (FIG. 8D) of the number of mCherry-labeled neutrophils at the wound in WT and mydgf$^{-/-}$ larvae, with control or arnt-1 morpholino, at 1 and 6 hpw after Tt; three or four independent replicates with n=46+/+ control mo, 33+/+ arnt-1 mo, 50−/− control mo, and 38−/− arnt-1 mo at 1 hpw and 54+/+ control mo, 38+/+ arnt-1 mo, 68−/− control mo, and 73−/− arnt-1 mo at 6 hpw; scale bar=100 μm. Data are expressed as mean with 95% CI; each symbol represents one larva, and different colors represent independent replicates. *, P<0.05; **, P<0.01. P values were calculated by ANOVA with Tukey's multiple comparisons.

(FIG. 9A) Number of neutrophils around tumor cells present within a 100 m radius at 1 day post-injection of tumor cells. MyDGF+/+ n=27, MyDGF−/− n=30, from two (2) independent experiments. (FIG. 9B) Number of larvae that had disseminated tumor cells were quantified and plotted as percent dissemination. MyDGF+/+n=92, MyDGF−/− n=82; two (2) independent experiments.

DETAILED DESCRIPTION

Abbreviations and Definitions

Figure 1A:
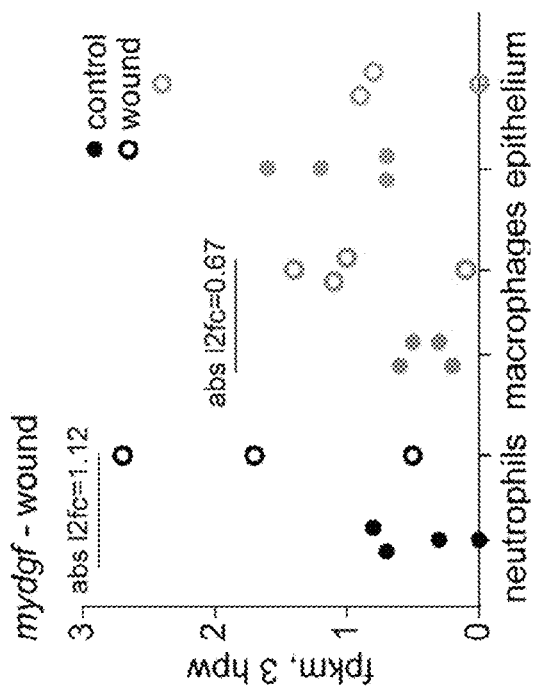
FIGS. 1A-1C. mydgf expression in sterile injuries and infection.

The articles "a" and "an" are used herein to refer to one or more than one (i.e., to at least one) of the grammatical object of the article. By way of example, "an element" means one element or more than one element.

The term "about" is used herein to mean a value±5% of a given numerical value. For example, "about 60%" as used herein refers to a value of 60±(5% of 60) (i.e., between 57 and 63).

As used herein, an "analogous sequence" (or an "analog") is one wherein the biological and pharmacological function of the gene and/or encoded/expressed protein sequence is essentially the same as a reference gene or encoded protein such as, for example, a MYDGF gene and the encoded protein derived from humans vs. mice vs. zebra fish. Additionally, analogous genes/analogous proteins include at least about 20%, for example, at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% sequence identity with the sequence of the reference gene or polynucleotide. Analogous sequences are determined by known methods of sequence alignment.

The term "alignment" refers to a method of comparing two or more polynucleotides or polypeptide sequences for the purpose of determining their relationship to each other. Alignments are typically performed by computer programs that apply various algorithms. It is also possible, but laborious, to perform an alignment by hand. Alignment programs typically iterate through potential alignments of sequences and score the alignments using substitution tables, employing a variety of strategies to reach a potential optimal alignment score. Commonly-used alignment algorithms include, but are not limited to, CLUSTALW, (see, Thompson J. D., Higgins D. G., Gibson T. J., CLUSTAL W (1994): improving the sensitivity of progressive multiple sequence alignment through sequence weighting, position-specific gap penalties and weight matrix choice, *Nucleic Acids Research* 22:4673-4680); CLUSTALV, (see, Larkin M. A., et al., (2007) CLUSTALW2, ClustalW and ClustalX version 2, *Bioinformatics* 23(21):2947-2948; Jotun-Hein, Muscle et al., (2004) MUSCLE: a multiple sequence alignment method with reduced time and space complexity, *BMC Bioinformatics* 5:113); Mafft, Kalign, ProbCons, and T-Coffee (see Notredame et al., (2000) T-Coffee: A novel method for multiple sequence alignments, *Journal of Molecular Biology* 302:205-217). Exemplary programs that implement one or more of the above algorithms include, but are not limited to MegAlign from DNAStar (DNAStar, Inc., Madison, Wisconsin, USA), and MUSCLE, T-Coffee, CLUSTALX, CLUSTALV, JalView, Phylip, and Discovery Studio from Accelrys (Accelrys, Inc., San Diego, California, USA). In a non-limiting example, MegAlign is used to implement the CLUSTALW alignment algorithm with the following parameters: Gap Penalty 10, Gap Length Penalty 0.20, Delay Divergent Seqs (30%) DNA Transition Weight 0.50, Protein Weight matrix Gonnet Series, DNA Weight Matrix IUB.

The term "antibodies" refers to immunoglobulins. Antibodies include but are not limited to immunoglobulins obtained directly from any species from which it is desirable to produce antibodies. In addition, the present invention encompasses modified antibodies. The term also refers to antibody fragments that retain the ability to bind to the same epitope to which the intact antibody also binds, and include polyclonal antibodies, monoclonal antibodies, chimeric antibodies, anti-idiotype (anti-ID) antibodies. Antibody fragments include, but are not limited to the complementarity-determining regions (CDRs), single-chain fragment variable regions (scFv), heavy chain variable region (VH), light chain variable region (VL). Polyclonal and monoclonal antibodies are also encompassed by the present invention. Preferably, the antibodies are monoclonal antibodies.

The term "consensus sequence" or "canonical sequence" refers to an archetypical amino acid sequence against which all variants of a particular protein or sequence of interest are compared. Either term also refers to a sequence that sets forth the nucleotides that are most often present in a polynucleotide sequence of interest. For each position of a protein, the consensus sequence gives the amino acid that is most abundant in that position in the sequence alignment.

As used herein, the term "consensus mutation" refers to a difference in the sequence of a starting gene and a consensus sequence. Consensus mutations are identified by comparing the sequences of the starting gene and the consensus sequence resulting from a sequence alignment. In some embodiments, consensus mutations are introduced into the starting gene such that it becomes more similar to the consensus sequence. Consensus mutations also include amino acid changes that change an amino acid in a starting gene to an amino acid that is more frequently found in a multiple sequence alignment (MSA) at that position relative to the frequency of that amino acid in the starting gene. Thus, the term "consensus mutation" refers to any amino acid change that replaces an amino acid of the starting gene with an amino acid that is more abundant in the MSA than the native amino acid.

The term "conservative substitutions" or "conserved substitutions" refers to, for example, a substitution wherein one or more of the following amino acid substitutions are made: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as histidine, lysine and arginine, with another basic residue; and replacement of an aromatic residue, such as tryptophan, phenylalanine and tyrosine, with another aromatic residue; or replacement of small amino acids, such as glycine, alanine, serine, threonine and methionine, with another small amino acid. Amino acid substitutions which do not generally alter the specific activity are known in the art and are described, for example, by H. Neurath and R. L. Hill, in "The Proteins," Academic Press, New York, 1979. Useful conservative modifications include Alanine to Cysteine, Glycine, or Serine; Arginine to Isoleucine, Lysine, Methionine, or Ornithin; Asparagine to Aspartic acid, Glutamine, Glutamic acid, or Histidine; Aspartic acid to Asparagine, Glutamine, or Glutamic acid; Cysteine to Methionine, Serine, or Threonine; Glutamine to Asparagine, Aspartic acid, or Glutamic acid; Glutamic acid to Asparagine, Aspartic acid, or Glatmine; Glycine to Aspartic acid, Alanine, or Proline; Histidine to Asparagine, or Glutamine; Isoleucine to Leucine, Methionine, or Valine; Leucine to Isoleucine, Methionine, or Valine; Lysine to Arginine, Glutamine, Glutamic acid, Isoleucine, Methionine, or Ornithin; Methionine to Cysteine, Isoleucine, Leucine, or Valine; Phenylalanine to Histidine, L-Dopa, Leucine, Methionine, Threonine, Tryptophan, Tyrosine, 3-phenylproline, 4-phenylproline, or 5-phenylproline; Proline to L-1-thioazolidine-4-carboxylic acid or D- or L-1-oxazolidine-4-carboxylic acid; Serine to Cysteine, Methionine, or Threonine; Threonine to Methionine, Serine, or Valine; Tryptophan to Tyrosine; Tyrosine to L-Dopa, Histidine, or Phenylalanine; and Valine to Isoleucine, Leucine, or Methionine.

The term "corresponds to" refers to an amino acid residue in a first protein sequence being positionally equivalent to an amino acid residue in a second reference protein sequence by virtue of the fact that the residue in the first protein sequence lines up with the residue in the reference sequence using bioinformatic techniques, for example, using the methods described herein for preparing a sequence alignment. The corresponding residue in the first protein sequence is then assigned the residue number in the second reference protein sequence. The first protein sequence can be analogous to the second protein sequence or non-analogous to the second protein sequence, although it is preferred that the two protein sequences are analogous sequences.

The term "deletion," when used in the context of an amino acid sequence, means a deletion in or a removal of a residue from the amino acid sequence of a precursor protein, resulting in a mutant protein having one less amino acid residue as compared to the precursor protein. The term can also be used in the context of a nucleotide sequence, which means a deletion in or removal of a residue from the polynucleotide sequence of a precursor polynucleotide.

The term "DNA construct" and "transforming DNA" are used interchangeably herein to refer to a DNA used to introduce sequences into a host cell or organism. A DNA construct is generated in vitro by PCR or other suitable techniques known to those in the art. In some embodiments, the sequence is operably linked to additional elements such as control elements (e.g., promoters, etc.). A DNA construct can further comprise a selectable marker. It can also comprise an incoming sequence flanked by homology boxes. In a further embodiment, the DNA construct comprises other non-homologous sequences, added to the ends (e.g., stuffer sequences or flanks). In some embodiments, the ends of the incoming sequence are closed such that the DNA construct forms a closed circle. The transforming sequences may be wildtype, mutant or modified. In some embodiments, the DNA construct comprises sequences homologous to the host cell chromosome. In other embodiments, the DNA construct comprises non-homologous sequences. Once the DNA construct is assembled in vitro it may be used to: 1) insert heterologous sequences into a desired target sequence of a host cell; 2) mutagenize a region of the host cell chromosome (i.e., replace an endogenous sequence with a heterologous sequence); 3) delete target genes; and/or (4) introduce a replicating plasmid into the host.

A polynucleotide is said to "encode" a RNA or a polypeptide if, in its native state or when manipulated by methods known to those of skill in the art, it can be transcribed and/or translated to produce the RNA, the polypeptide, or a fragment thereof. The antisense strand of such a polynucleotide is also said to encode the RNA or polypeptide sequences. As is known in the art, a DNA can be transcribed by an RNA polymerase to produce an RNA, and an RNA can be reverse transcribed by reverse transcriptase to produce a DNA. Therefore a DNA can encode an RNA, and vice-versa.

The term "expressed genes" refers to genes that are transcribed into messenger RNA (mRNA) and then translated into protein, as well as genes that are transcribed into various types of RNA, such as transfer RNA (tRNA), ribosomal RNA (rRNA), and regulatory RNA, which are not translated into protein.

The terms "expression cassette" or "expression vector" refers to a polynucleotide construct generated recombinantly or synthetically, with a series of specified elements that permit transcription of a particular polynucleotide in a target cell. A recombinant expression cassette can be incorporated into a plasmid, chromosome, mitochondrial DNA, plasmid DNA, virus, or polynucleotide fragment. Typically, the recombinant expression cassette portion of an expression vector includes, among other sequences, a polynucleotide sequence to be transcribed and a promoter. In particular embodiments, expression vectors have the ability to incorporate and express heterologous polynucleotide fragments in a host cell. Many prokaryotic and eukaryotic expression vectors are commercially available. Selection of appropriate expression vectors is within the knowledge of those of skill in the art. The term "expression cassette" is also used interchangeably herein with "DNA construct," and their grammatical equivalents.

The term "functional assay" refers to an assay that provides an indication of the activity of a protein. In particularly preferred embodiments, the term refers to an assay system in which a protein is analyzed for its ability to function in its natural capacity. For example, in the case of enzymes, a functional assay involves determining the effectiveness of the enzyme in catalyzing a reaction.

"Gene" refers to a polynucleotide (e.g., a DNA segment), which encodes a polypeptide, and which may (in eukaryotes) include regions preceding and following the coding regions as well as intervening sequences (introns) between individual coding segments (exons).

The term "homologous genes" refers to a pair of genes from different species which correspond to each other and which are identical or similar to each other. The term encompasses genes that are separated by the speciation process during the development of new species) (e.g., orthologous genes), as well as genes that have been separated by genetic duplication (e.g., paralogous genes).

The term "endogenous protein" refers to a protein that is native to or naturally occurring in a cell. "Endogeneous polynucleotide" refers to a polynucleotide that is in the cell and was not introduced into the cell using recombinant engineering techniques. For example, a gene that was present in the cell when the cell was originally isolated from nature. A gene is still considered endogenous if the control sequences, such as a promoter or enhancer sequences that activate transcription or translation, have been altered through recombinant techniques. Conversely, the term "heterologous" refers to a protein or a polynucleotide that does not naturally occur in a host cell.

The term "homologous recombination" refers to the exchange of DNA fragments between two DNA molecules or paired chromosomes at sites of identical or nearly identical nucleotide sequences. In certain embodiments, chromosomal integration is homologous recombination.

The term "homologous sequences" as used herein refers to a polynucleotide or polypeptide sequence having, for example, about 100%, about 99% or more, about 98% or more, about 97% or more, about 96% or more, about 95% or more, about 94% or more, about 93% or more, about 92% or more, about 91% or more, about 90% or more, about 88% or more, about 85% or more, about 80% or more, about 75% or more, about 70% or more, about 65% or more, about 60% or more, about 55% or more, about 50% or more, about 45% or more, or about 40% or more sequence identity to another polynucleotide or polypeptide sequence when optimally aligned for comparison. Homologous sequences may retain the same type and/or level of a particular activity of interest. In some versions of the method, homologous sequences have between 85% and 100% sequence identity, whereas in other versions there is between 90% and 100% sequence identity. In particular versions of the method, there is between 95% and 100% sequence identity.

"Homology" refers to sequence similarity or sequence identity. Homology is determined using standard techniques known in the art (see, e.g., Smith and Waterman, *Adv. Appl. Math.*, 2:482, 1981; Needleman and Wunsch, *J. Mol. Biol.*, 48:443, 1970; Pearson and Lipman, *Proc. Natl. Acad. Sci. USA* 85:2444, 1988; programs such as GAP, BESTFIT, FASTA, and TFASTA in the Wisconsin Genetics Software Package (Genetics Computer Group, Madison, Wisconsin, USA); and Devereux et al., *Nucl. Acid Res.*, 12:387-395, 1984). A non-limiting example includes the use of the BLAST program (Altschul et al., Gapped BLAST and PSI-BLAST: a new generation of protein database search programs, *Nucleic Acids Res.* 25:3389-3402, 1997) to identify sequences that can be said to be "homologous." A recent version such as version 2.2.16, 2.2.17, 2.2.18, 2.2.19, or the latest version, including sub-programs such as blastp for protein-protein comparisons, blastn for nucleotide-nucleotide comparisons, tblastn for protein-nucleotide comparisons, or blastx for nucleotide-protein comparisons, and with parameters as follows: Maximum number of sequences returned 10,000 or 100,000; E-value (expectation value) of 1e-2 or 1e-5, word size 3, scoring matrix BLOSUM62, gap cost existence 11, gap cost extension 1, may be suitable. An E-value of $1 \times 10^{-5}$, for example, indicates that the chance of a homologous match occurring at random is about 1 in 10,000, thereby marking a high confidence of true homology.

The term "host strain" or "host cell" refers to a suitable host for expressing a protein of interest from a vector comprising DNA that encodes the protein of interest.

The term "insertion," when used in the context of a polypeptide sequence, refers to an insertion in the amino acid sequence of a precursor polypeptide, resulting in a mutant polypeptide having an amino acid that is inserted between two existing contiguous amino acids, i.e., adjacent amino acids residues, which are present in the precursor polypeptide. The term "insertion," when used in the context of a polynucleotide sequence, refers to an insertion of one or more nucleotides in the precursor polynucleotide between two existing contiguous nucleotides, i.e., adjacent nucleotides, which are present in the precursor polynucleotides.

The term "introduced" refers to, in the context of introducing a polynucleotide sequence into a cell, any method suitable for transferring the polynucleotide sequence into the cell. Such methods for introduction include but are not limited to protoplast fusion, transfection, transformation, conjugation, and transduction (see, e.g., Ferrari et al., Genetics, in Hardwood et al, (eds.), *Bacillus*, Plenum Publishing Corp., pp. 57-72, 1989).

The term "isolated" or "purified" means a material that is removed from its original environment, for example, the natural environment if it is naturally occurring, or a fermentation broth if it is produced in a recombinant host cell fermentation medium. A material is said to be "purified" when it is present in a particular composition in a higher or lower concentration than the concentration that exists prior to the purification step(s). For example, with respect to a composition normally found in a naturally occurring or wild type organism, such a composition is "purified" when the final composition does not include some material from the original matrix. As another example, where a composition is found in combination with other components in a recombinant host cell fermentation medium, that composition is purified when the fermentation medium is treated in a way to remove some component of the fermentation, for example, cell debris or other fermentation products, via, for example, centrifugation or distillation. As another example, a naturally-occurring polynucleotide or polypeptide present in a living animal is not isolated, but the same polynucleotide or polypeptide, separated from some or all of the coexisting materials in the natural system, is isolated, whether such process is through genetic engineering or mechanical separation. Such polynucleotides can be parts of vectors. Alternatively, such polynucleotides or polypeptides can be parts of compositions. Such polynucleotides or polypeptides can be considered "isolated" because the vectors or compositions comprising thereof are not part of their natural environments. In another example, a polynucleotide or protein is said to be purified if it gives rise to essentially one band in an electrophoretic gel or a blot.

"Mutation" or "mutated" means, in the context of a protein, a modification to the amino acid sequence resulting in a change in the sequence of a protein with reference to a precursor protein sequence. A mutation can refer to a substitution of one amino acid with another amino acid, an insertion or a deletion of one or more amino acid residues. Specifically, a mutation can also be the replacement of an amino acid with a non-natural amino acid, or with a chemically modified amino acid or like residues. A mutation can also be a truncation (e.g., a deletion or interruption) in a sequence or a subsequence from the precursor sequence. A mutation may also be an addition of a subsequence (e.g., two or more amino acids in a stretch, which are inserted between two contiguous amino acids in a precursor protein sequence) within a protein, or at either terminal end of a protein, thereby increasing the length of (or elongating) the protein. A mutation can be made by modifying the DNA sequence corresponding to the precursor protein. Mutations can be introduced into a protein sequence by known methods in the art, for example, by creating synthetic DNA sequences that encode the mutation with reference to precursor proteins, or chemically altering the protein itself.

Myeloid-derived growth factor (MYDGF) refers to a conserved protein found in a wide range of vertebrates (e.g., humans, mice, bovines, zebrafish, and many others). The amino acid sequence for human MYDGF is recorded in UniProt at entry Q969H8; for mice (*Mus musculus*) at Q9CPT4, for bovines (*Bos taurus*) at P62248, and for zebrafish (*Danio rerio*) at A7MCH1 and Q6DGL1. The protein is expressed with an N-terminal signal sequence, followed by the mature protein. In the following sequences, the signal sequence is underlined; the remainder of the sequence is the mature protein:

MYDGF Amino Acid Sequence, Human (UniProtKB—Q969H8):

```
                                          (SEQ. ID. NO: 1)
         10         20         30         40
MAAPSGGWNG VGASLWAALL LGAVALRPAE AVSEPTTVAF 50         60         70         80
DVRPGGVVHS FSHNVGPGDK YTCMFTYASQ GGTNEQWQMS 90        100        110        120
LGTSEDHQHF TCTIWRPQGK SYLYFTQFKA EVRGAEIEYA 130        140        150        160
MAYSKAAFER ESDVPLKTEE FEVTKTAVAH RPGAFKAELS

170
KLVIVAKASR TEL
```

The genetic data for the corresponding mRNA in humans can be found at NCBI Reference Sequence: NM_019107.4

```
FEATURES         Location/Qualifiers
source           1..990
                 /organism="Homo sapiens"
                 /mol_type="mRNA"
                 /db_xref="taxon:9606"
                 /chromosome="19"
                 /map="19p13.3"
gene             1..990
                 /gene="MYDGF"
                 /gene_synonym="C19orf10;
                 EUROIMAGE1875335; IL25;
                 IL27; IL27w;
                 R33729_1; SF20"
                 /note="myeloid derived growth factor"
                 /db_xref="GeneID:56005"
                 /db_xref="HGNC:HGNC:16948"
                 /db_xref="MIM:606746"
exon             1..182
                 /gene="MYDGF"
                 /gene_synonym="C19orf15; EUROIMAGE1875335; IL25;
                 IL27; IL27w;
                 R33729_1; SF20"
                 /inference="alignment:Splign:2.1.0"
CDS              9..530
                 /gene="MYDGF"
                 /gene_synonym="C19orf10; EUROIMAGE1875335; IL25;
                 IL27; IL27w;
                 R33729_1; SF20"
                 /note="interleukin 27 working designation;
                 interleukin-25;
                 stromal cell-derived growth factor SF20;
                 UPF0556 protein
                 C19orf10"
                 /codon_start=1
                 /product="myeloid-derived growth factor precursor"
                 /protein_id="NP_061980.1"
                 /db_xref="CCDS:CCDS12133.1"
                 /db_xref="GeneID:56005"
                 /db_xref="HGNC:HGNC:16948"
                 /db_xref="MIM:606746"
/translation="MAAPSGGWNGVGASLWAALLLGAVALRPAEAVSEPTTVAFDVRP

GGVVHSFSHNVGPGDKYTCMFTYASQGGTNEQWQMSLGTSEDHQHFTCTIWRPQGKSY

LYFTQFKAEVRGAEIEYAMAYSKAAFERESDVPLKTEEFEVTKTAVAHRPGAFKAELS

KLVIVAKASRTEL" (SEQ.ID. NO: 1)

sig_peptide      9..101
                 /gene="MYDGF"
                 /gene_synonym="C19orf10; EUROIMAGE1875335; IL25;
                 IL27; IL27w; R33729_1; SF20"
                 /inference="COORDINATES: ab initio
                 prediction:SignalP:4.0"
mat_peptide      102..527
                 /gene="MYDGF"
                 /gene_synonym="C19orf10; EUROIMAGE1875335; IL25;
                 IL27;
                 IL27w; R33729_1; SF20"
                 /product="Myeloid-derived growth factor.
                 /id=PRO_0000021008"
                 /note="propagated from UniProtKB/Swiss-Prot
                 (Q969H8.1)"
exon             183..233
                 /gene="MYDGF"
                 /gene_synonym="C19orf10; EUROIMAGE1875335; IL25;
                 IL27; IL27w; R33729_1; SF20"
                 /inference="alignment:Splign:2.1.0"
exon             234..295
                 /gene="MYDGF"
                 /gene_synonym="C19orf10; EUROIMAGE1875335; IL25;
                 IL27; IL27w; R33729_1; SF20"
                 /inference="alignment:Splign:2.1.0"
```

-continued

| FEATURES | Location/Qualifiers |
|---|---|
| exon | 296..377<br>/gene="MYDGF"<br>/gene_synonym="C19orf10; EUROIMAGE1875335;<br>IL25; IL27;<br>IL27w; R33729_1; SF20"<br>/inference="alignment:Splign:2.1.0" |
| exon | 378..450<br>/gene="MYDGF"<br>/gene_synonym="C19orf10; EUROIMAGE1875335; IL25;<br>IL27; IL27w; R33729_1; SF20"<br>/inference=11 alignment: Splign: 2.1.0" |
| exon | 451..990<br>/gene="MYDGF"<br>/gene_synonym="C19orf10; EUROIMAGE1875335; IL25;<br>IIL27; L27w; R33729_1; SF20"<br>/inference="alignment:Splign:2.1.0" |
| regulatory | 979..984<br>/regulatory_class="polyA_signal_sequence"<br>/gene="MYDGF"<br>/gene_synonym="C19orf10; EUROIMAGE1875335; IL25;<br>IL27; IL27w; R33729_1; SF20"<br>/note="hexamer: ATTAAA" |
| polyA_site | 990<br>/gene="MYDGF"<br>/gene_synonym="C19orf10; EUROIMAGE1875335; IL25;<br>IIL27; L27w; R33729_1; SF20"<br>/note="major polyA site" |

```
ORIGIN
  1 agtccaacat ggcggcgccc agcggagggt ggaacggcgt cggcgcgagc ttgtgggccg
 61 cgctgctcct aggggccgtg gcgctgaggc cggcggaggc ggtgtccgag cccacgacgg
121 tggcgtttga cgtgcggccc ggcggcgtcg tgcattcctt ctcccataac gtgggccggg
181 gggacaaata tacgtgtatg ttcacttacg cctctcaagg agggaccaat gagcaatggc
241 agatgagtct ggggaccagc gaagaccacc agcacttcac ctgcaccatc tggaggcccc
301 aggggaagtc ctatctgtac ttcacacagt tcaaggcaga ggtgcgggc gctgagattg
361 agtacgccat ggcctactct aaagccgcat tgaaaggga aagtgatgtc cctctgaaaa
421 ctgaggaatt tgaagtgacc aaaacagcag tggctcacag gcccggggca ttcaaagctg
481 agctgtccaa gctggtgatt gtggccaagg catcgcgcac tgagctgtga ccagcagccc
541 tgttgcgggt ggcaccttct catctccggt gaagctgaag gggcctgtgt ccctgaaagg
601 gccagcacat cactggtttt ctaggaggga ctcttaagtt ttctacctgg gctgacgttg
661 ccttgtccgg aggggcttgc agggtggctg aagccctggg gcagagaaca gagggtccag
721 ggccctcctg gctcccaaca gcttctcagt tcccacttcc tgctgagctc ttctggactc
781 aggatcgcag atccggggca caagagggt ggggaacatg ggggctatgc tggggaaagc
841 agccatgctc cccccgacct ccagccgagc atccttcatg agcctgcaga actgctttcc
901 tatgtttacc caggggacct cctttcagat gaactgggaa gagatgaaat gtttttttcat
961 atttaaataa ataagaacat taaaaagcaa (SEQ. ID. NO: 2)
```

MYDGF Amino Acid Sequence, Mouse (UniProtKB—Q9CPT4):

(SEQ. ID. NO: 3)

```
         10         20         30         40
MAAPSGGFWT AVVLAAAALK LAAAVSEPTT VPFDVRPGGV 50         60         70         80
VHSFSQDVGP GNKFTCTFTY ASQGGTNEQW QMSLGTSEDS 90        100        110        120
QHFTCTIWRP QGKSYLYFTQ FKAELRGAEI EYAMAYSKAA 130        140        150        160
FERESDVPLK SEEFEVTKTA VSHRPGAFKA ELSKLVIVAK

AARSEL
```

The genetic data for the corresponding mRNA in mice can be found at NCBI Reference Sequence: NM_080837.2

| FEATURES | Location/Qualifiers |
|---|---|
| source | 1..913<br>/organism="*Mus musculus*"<br>/mol_type="mRNA"<br>/strain="C57BL/6"<br>/db_xref="taxon:10090"<br>/chromosome="17"<br>/map="17 29.2 cM" |
| gene | 1..913<br>/gene="Mydgf"<br>/gene_synonym="D17Wsu104; D17Wsu104e; Il25; Ly6elg"<br>/note="myeloid derived growth factor"<br>/db_xref="GeneID:28106"<br>/db_xref="MGI:MGI:2156020" |
| exon | 1..182<br>/gene="Mydgf"<br>/gene_synonym="D17Wsu104; D17Wsu104e; Il25; Ly6elg"<br>/inference="alignment:Splign:2.1.0" |
| CDS | 30..530<br>/gene="Mydgf"<br>/gene_synonym="D17Wsu104; D17Wsu104e; Il25; Ly6elg"<br>/note="UPF0556 protein C19orf10 homolog"<br>/codon_start=1<br>/product="myeloid-derived growth factor precursor"<br>/protein_id="NP_543027.1"<br>/db_xref="CCDS:CCDS28898.1"<br>/db_xref="GeneID:28106"<br>/db_xref="MGI:MGI:2156020" |

/translation=MAAPSGGFWTAVVLAAAALKLAAAVSEPTTVPFDVRPGGVVHSF

SQDVGPGNKFTCTFTYASQGGTNEQWQMSLGTSEDSQHFTCTIWRPQGKSYLYFTQFK

AELRGAEIEYAMAYSKAAFERESDVPLKSEEFEVTKTAVSHRPGAFKAELSKLVIVAK
SEQ. ID. NO: 4)

AARSEL (SEQ. ID. NO: 5)

| | |
|---|---|
| sig_peptide | 30..101<br>/gene="Mydgf"<br>/gene_synonym="D17Wsu104; D17Wsu104e; Il25; Ly6elg"<br>/inference="COORDINATES: ab initio prediction:SignalP:4.0" |
| exon | 183..233<br>/gene="Mydgf"<br>/gene_synonym="D17Wsu104; D17Wsu104e; Il25; Ly6elg"<br>/inference="alignment:Splign:2.1.0" |
| exon | 234..295<br>/gene="Mydgf"<br>/gene_synonym="D17Wsu104; D17Wsu104e; Il25; Ly6elg"<br>/inference="alignment:Splign:2.1.0" |
| exon | 296..377<br>/gene="Mydgf"<br>/gene_synonym="D17Wsu104; D17Wsu104e; Il25; Ly6elg"<br>/inference="alignment:Splign:2.1.0" |
| exon | 378..450<br>/gene="Mydgf"<br>/gene_synonym="D17Wsu104; D17Wsu104e; Il25; Ly6elg"<br>/inference="alignment:Splign:2.1.0" |
| exon | 451..913<br>/gene="Mydgf"<br>/gene_synonym="D17Wsu104; D17Wsu104e; Il25; Ly6elg"<br>/inference="alignment:Splign:2.1.0" |
| regulatory | 860..865<br>/regulatory_class="polyA_signal_sequence"<br>/gene="Mydgf"<br>/gene_synonym="D17Wsu104; D17Wsu104e; Il25; Ly6elg" |
| regulatory | 864..869<br>/regulatory_class="polyA_signal_sequence"<br>/gene="Mydgf"<br>/gene_synonym="D17Wsu104; D17Wsu104e; Il25; Ly6elg" |
| polyA_site | 913<br>/gene="Mydgf"<br>/gene_synonym="D17Wsu104; D17Wsu104e; Il25; Ly6elg" |

ORIGIN
   1 gagcgcctgc gcattgcccc ggaagcaaga tggcagcccc cagcggaggc ttctggactg
  61 cggtggtcct ggcggccgca gcgctgaaat ggccgccgc tgtgtccgag cccaccaccg

| FEATURES | Location/Qualifiers |
|---|---|

```
121 tgccatttga cgtgaggccc ggaggggtcg tgcattcgtt ctcccaggac gtaggacccg 181 ggaacaagtt tacatgtaca ttcacctacg cttcccaagg agggaccaac gagcaatggc 241 agatgagcct ggggacaagt gaagacagcc agcactttac ctgtaccatc tggaggcccc 301 aggggaaatc ctacctctac ttcacacagt tcaaggctga gttgcgaggt gctgagatcg 361 agtatgccat ggcctactcc aaagccgcat tgagagaga gagtgatgtc ccctgaaaa 421 gtgaggagtt tgaagtgacc aagacagcag tgtctcacag gcctggggcc ttcaaagctg 481 agctctccaa gctggtgatc gtagccaagg cggcacgctc ggagctgtga ccctcgcctg 541 tcaagggcct tcatgtccac gttcctcagg cacactgacc gggactactt gtctagggca 601 ctggttccca taggagctgc cctgccctgc acaggtcaca ctgtgtcact ccgcagaact 661 ctctgagccc ggtcacctgt tttgccaggg aagatgcagg gcatgtgcgg gggtgggatg 721 gaaggacttc ctggctttcc tgaagtcaag atgtggtgtg gtttcccctc tgagccacag 781 atgagtgtcc ccatcccagg accactttct aaccccatcc agggcagctc cactcagaag 841 gatgggaaag gatagaaaaa ataaataaat aagtagccac cttagtggtg gctctgtggg 901 gtcaggactc aga (SEQ. ID. NO: 6)
```

MYDGF Amino Acid Sequence, Zebrafish (UniProtKB—A7MCH1):

```
                                    (SEQ. ID. NO: 7)
            10         20         30         40
    MAFIVHMKWF VNLLLLFVVL CELCSAERTK TLDFDVKPGG 50         60         70         80
    VVQTFSAKLK KYKCTFTYAC QGGTNEQWQM SVGLSDDEQM 90        100        110        120
    FSCSVWRPQG KSYLFFTQFK AEIKGAKIEY ATAYSQTAVG 130        140        150        160
    GQRDVALKEE EYIVSESAVT QRDGKFHSEL SKLTVIGRIR

HDEL
```

The genetic data for the corresponding mRNA in zebrafish can be found at GenBank Reference Sequence: BC076331.1

| FEATURES | Location/Qualifiers |
|---|---|
| source | 1..1473<br>/organism="*Danio rerio*"<br>/mol_type="mRNA"<br>/db_xref="taxon:7955"<br>/clone="MGC:92871 IMAGE:7117831"<br>/tissue_type="Brain"<br>/clone_lib="NIH_ZGC_4"<br>/lab_host="DH10B"<br>/note="Vector: pME18S-FL3" |
| gene | 1..1473<br>/gene="zgc:92871"<br>/db_xref="GeneID:436753"<br>/db_xref="ZFIN:ZDB-GENE-040718-183" |
| CDS | 83..577<br>/gene="zgc:92871"<br>/codon_start=1<br>/product="zgc:92871"<br>/protein_id="AAH76331.1"<br>/db_xref="GeneID:436753"<br>/db_xref="ZFIN:ZDB-GENE-040718-183"<br>/translation=MAFIVHMKWFVNLLLLFVVLCELCSAERTKTLDFDVKPGGVVQT<br><br>FSAKLKKYKCTFTYACQGGTNEQWQMSVGLSDDEQMFSCSVWRPQGKSYLFFTQFKAE<br><br>IKGAKIEYATAYSQTAVGGQRDVALKEEEYIVSESAVTQRDQKFHSELSKLTVIGRIR<br><br>HDEL (SEQ. ID. NO: 7) |

-continued

```
FEATURES    Location/Qualifiers

ORIGIN
   1 atcctatgaa gaacatacag gaacagtaca ggcaccttttt tcattcacaa cataaacgca
  61 gatctcctgt ctgtaaagca tcatggcatt tattgtgcac atgaaatggt ttgtgaatct
 121 tctgctgctg tttgttgtgc tttgtgaact gtgttctgct gaaaggacca aaacactgga
 181 cttcgatgtc aaacctggag gagttgtgca gactttctct gcaaaactta agaagtataa
 241 atgcaccttc acatatgcat gccaaggagg aaccaatgag caatggcaaa tgagtgtcgg
 301 actaagtgac gatgagcaaa tgttttcctg ttcagtatgg aggccccaag ggaagtccta
 361 cttgtttttt acgcagttca aagccgagat aaaaggagcc aagatcgagt acgccaccgc
 421 atattcccag acggccgtgg gtggacagag ggatgttgct ttgaaagaag aagagtacat
 481 agtgtcagag tctgcagtga cacaaagaga tggaaaattc cattcggagc tttctaagct
 541 cactgtcatt ggtcgaatac ggcatgatga actctgattg gccgattcga aggacgttgg
 601 ttatttaaca gctttggaca caattttctg ctcacggtca taagtcaagc gaaggaaatc
 661 acagcactgg acattctgaa aaatgaattt accgtgatag aaaagatttc ctatagatgc
 721 cagtggccaa aggttggagt gatcatcaga ggtagacgaa aagtctatta ttggatatta
 781 taagggtaa aacaaattgt acatgcgcat ttttttcata tttgtaaggt gttataaagt
 841 cttctttata ttcagtgcag aacagcagat tgatttctgt tcttgtcaga atttatgggt
 901 tttctagggt tacagtctga ctttgattca tacctgcaaa gctgattatc aagagtgctc
 961 atacttactt tcctaggctg gtgtaaaggc acgcttgtag acaattccca ctaaatcttt
1021 ggggtgtgtt agaatccttt gagtatttct gtggtggagg aaaaaacatc aagttggtta
1081 ctacagttcc ttttgtctcc cagtcatgct ttattctgat aaccgatgta tcggaatttg
1141 aataaatctg ttatcagaac aatttgactt ctggccttac tatttgctga ctttgtatac
1201 ctaatatttt tgcgtaaagt aagtgaattg tgtctgttta aaagcaacaa cctctgaggg
1261 ctgttttttt tgcactctta agggtgaaaa atgtgtgtaa ttctgctgca taaaattaaa
1321 ataagctaca aatttgctga ttctgttcaa gatttgtcca gtcagctctt taaaaggctt
1381 gtcggtaccc caactgtgaa taaaagagcc tgcaatgcaa ttcacaagct attaaagaaa
1441 ttaatgtctt gagaaccaaa aaaaaaaaaa aaa (SEQ. ID. NO: 8)
```

The terms "operably linked" and "operatively linked" are synonymous and refer to the placement of one polynucleotide sequence into a functional relationship with another polynucleotide sequence. For example, a DNA encoding a secretory leader (e.g., a signal peptide) is operably linked to a DNA encoding a polypeptide if it is expressed as a preprotein that participates in the secretion of the polypeptide. A promoter or an enhancer is operably linked to a coding sequence if it affects the transcription of the sequence. A ribosome binding site is operably linked to a coding sequence if it is positioned to facilitate translation. Generally, "operably linked" means that the DNA sequences so linked are in the same reading frame, but not necessarily physically linked directly to each other.

The terms "percent sequence identity," "percent amino acid sequence identity," "percent gene sequence identity," and/or "percent polynucleotide sequence identity," with respect to two polypeptides, polynucleotides and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

"Pharmaceutically suitable salt" means any acid or base addition salt whose counter-ions are non-toxic to the subject or patient in pharmaceutical doses of the salts, so that the beneficial inhibitory effects inherent in the free base or free acid are not vitiated by side-effects ascribable to the counter-ions. A host of pharmaceutically suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically suitable salt by ion exchange procedures. Pharmaceutically suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bis b hydroxynaphthoates, gentisates, isethionates, di-p-toluoyltartrates, methane sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N-methylmorpholine, and the like. See, for example, "Handbook of Pharmaceutical Salts, Properties, Selection, and Use," P. H. Stahl and C. G. Wermuch, Eds., © 2008, Wiley-VCH (Zurich, Switzerland), ISBN: 978-3-90639-058-1.

The terms "protein" and "polypeptide" are used interchangeably herein. The 3-letter code as well as the 1-letter code for amino acid residues as defined in conformity with the IUPAC-IUB Joint Commission on Biochemical Nomenclature (JCBN) is used throughout this disclosure. It is also understood that a polypeptide may be coded for by more than one polynucleotide sequence due to the degeneracy of the genetic code. An enzyme is a protein.

The term "recombinant," when used to modify the term "cell" or "vector" herein, refers to a cell or a vector that has been modified by the introduction of a heterologous polynucleotide sequence, or that the cell is derived from a cell so modified. Thus, for example, recombinant cells express genes that are not found in identical form within the native (non-recombinant) form of the cells or express, as a result of deliberate human intervention, native genes that are otherwise abnormally expressed, under-expressed, or not expressed. The terms "recombination," "recombining," and generating a "recombined" polynucleotide refer generally to the assembly of two or more polynucleotide fragments wherein the assembly gives rise to a chimeric polynucleotide made from the assembled parts.

The term "regulatory segment," "regulatory sequence," or "expression control sequence" refers to a polynucleotide sequence that is operably linked with another polynucleotide sequence that encodes the amino acid sequence of a polypeptide chain to effect the expression of that encoded amino acid sequence. The regulatory sequence can inhibit, repress, promote, or even drive the expression of the operably linked polynucleotide sequence encoding the amino acid sequence.

The term "selectable marker" or "selective marker" refers to a polynucleotide (e.g., a gene) capable of expression in a host cell, which allows for ease of selection of those hosts containing the vector. Examples of selectable markers include but are not limited to fluorescent markers and antimicrobial markers. Thus, the term "selectable marker" refers to a gene that provides an indication when a host cell has taken up an incoming sequence of interest or when some other reaction has taken place. Typically, selectable markers are genes that confer antimicrobial resistance or a metabolic advantage on the host cells to allow the cells containing the exogenous sequences to be distinguished from the cells that have not received the exogenous sequences. Selective markers are known to those of skill in the art. As indicated above, suitably the marker is an antimicrobial resistant marker, including, for example, ampR; phleoR; specR; kanR; eryR; tetR; cmpR; and neoR. See, e.g., Guerot-Fleury, *Gene*, 167:335-337, 1995; Palmeros et al., *Gene*, 247:255-264, 2000; and Trieu-Cuot et al., *Gene*, 23:331-341, 1983. Other markers useful in accordance with the invention include, but are not limited to, auxotrophic markers, such as tryptophan; and detection markers, such as 6-galactosidase, green fluorescent protein, and the like.

The term "substantially identical," in the context of two polynucleotides or two polypeptides refers to a polynucleotide or polypeptide that comprises at least 70% sequence identity, for example, at least 75%, at least 80%, at least 85%, at least 90%, at least 91%, at least 92%, at least 93%, at least 94%, at least 95%, at least 96%, at least 97%, at least 98%, or at least 99% sequence identity as compared to a reference sequence using the programs or algorithms (e.g., BLAST, ALIGN, CLUSTAL) using standard parameters. One indication that two polypeptides are substantially identical can be that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, when the two peptides differ only by a conservative substitution. Another indication that two polynucleotide sequences are substantially identical is that the two molecules hybridize to each other under stringent conditions (e.g., within a range of medium to maximum stringency).

"Substitution" means replacing an amino acid in the sequence of a precursor protein with another amino acid at a particular position, resulting in a mutant of the precursor protein. The amino acid used as a substitute can be a naturally occurring amino acid or can be a synthetic or non-naturally occurring amino acid.

Introduction:

Disclosed herein are:

1. A method to inhibit neutrophil recruitment to damaged tissue in a subject, the method comprising administering to a subject, the subject having a wound and/or a burn at a site on the subject, an amount of a myeloid-derived growth factor ("MYDGF"), a biologically active fragment thereof, an analogous sequence thereof, or a pharmaceutically suitable salt of any of the foregoing, wherein the amount is effective to inhibit neutrophil recruitment to the wound and/or burn site.

2. The method of claim 1, wherein the MYDGF has an amino acid sequence having at least 60% sequence identity, at least 70% sequence identity, at least 80% sequence identity, at least 90% sequence identity, at least 95% sequence, or at least 99% identity to the mature proteins shown in any of SEQ. ID. NOS:1, 3, or 7.

3. A method to inhibit inflammation in a subject, the method comprising administering to the subject an anti-inflammatory-effective amount of a myeloid-derived growth factor ("MYDGF"), a biologically active fragment thereof, an analogous sequence thereof, or a pharmaceutically suitable salt of any of the foregoing.

4. The method of claim 3, wherein the MYDGF has an amino acid sequence having at least 60% sequence identity, at least 70% sequence identity, at least 80% sequence identity, at least 90% sequence identity, at least 95% sequence, or at least 99% identity to the mature proteins shown in any of SEQ. ID. NOS:1, 3, or 7.

5. A method to promote wound healing in a subject, the method comprising administering to the subject an amount of a myeloid-derived growth factor ("MYDGF"), a biologically active fragment thereof, an analogous sequence thereof, or a pharmaceutically suitable salt of any of the foregoing, wherein the amount is effective to promote wound healing in the subject.

6. The method of claim 5, wherein the MYDGF has an amino acid sequence having at least 60% sequence identity, at least 70% sequence identity, at least 80% sequence identity, at least 90% sequence identity, at least 95% sequence, or at least 99% identity to the mature proteins shown in any of SEQ. ID. NOS:1, 3, or 7.

7. The method of any one of Claims 1-6, wherein the MYDGF is administered to a vertebrate subject.

8. The method of any one of Claims 1-6, wherein the MYDGF is administered to a mammalian subject.

9. The method of any one of Claims 1-6, wherein the MYDGF is administered to a human subject.

10. A pharmaceutical composition comprising myeloid-derived growth factor ("MYDGF"), a biologically active fragment thereof, or an analogous sequence thereof, in an amount effective to inhibit neutrophil recruitment to a wound or burn site in a subject administered the composition, or in an amount effective to inhibit inflammation in a subject administered the composition, or in an amount effective to promote wound healing in a subject administered the composition;

in combination with a pharmaceutically suitable carrier.

11. The pharmaceutical composition of Claim 10, wherein the MYDGF has an amino acid sequence having at least 60% sequence identity, at least 70% sequence identity, at least 80% sequence identity, at least 90% sequence identity, at least 95% sequence, or at least 99% identity to the mature proteins shown in any of SEQ. ID. NOS:1, 3, or 7.

Zebrafish MYDGF Knockout Mutant:

Zebrafish maintenance and handling. Animal care and use was approved by the Institutional Animal Care and Use Committee of University of Wisconsin and strictly followed guidelines set by the federal Health Research Extension Act and the Public Health Service Policy on the Humane Care and Use of Laboratory Animal, administered by the National Institutes of Health Office of Laboratory Animal Welfare. All protocols using zebrafish in this study were approved by the University of Wisconsin-Madison Research Animals Resource Center (protocol M005405-A02). AB and NHGRI-1 WT lines (LaFave et al., 2014) were used, as well as the previously published transgenic lines mpx:mCherry (Yoo et al., 2010), mpeg1:GFP (Ellett et al., 2011), mpx:dendra2 (Yoo and Huttenlocher, 2011), mpx:mCherry-2A-rac2 (Rosowski et al., 2016), and mpx:mCherry-2A-rac2D57N (Rosowski et al., 2016). Adult fish were maintained on a 14-h/10-h light/dark schedule. Following breeding, fertilized embryos were transferred to E3 medium (5 mM NaCl, 0.17 mM KCl, 0.44 mM $CaCl_2$), 0.33 mM $MgSO_4$, 0.025 mM NaOH, and 0.0003% Methylene Blue) and maintained at 28.5° C. Larval zebrafish were anesthetized using 0.2 mg/ml tricaine (ethyl 3-aminobenzoate; Sigma-Aldrich) before any experimentation or live imaging.

RT-qPCR. Tail tissue distal to the caudal yolk extension was dissected from 3 days post-fertilization (dpf) larvae following a 15-min incubation over ice. Approximately 50 tails per condition were pooled, and RNA was extracted using TRIZOL reagent (Invitrogen), according to the manufacturer's instructions. cDNA was synthesized from the RNA using the SuperScript III FirstStrand Synthesis System with Oligo(dT) (Thermo Fisher Scientific). qPCR was performed using FastStart Essential Green Master (Roche) and a Light-Cycler 96 (Roche). Data were normalized to ef1α using the ΔΔCq method (Livak and Schmittgen, 2001) and expressed as fold change ($2^{-\Delta\Delta Cq}$) over pooled WT or unwounded larvae. The following primers were used:

```
mydgf:
forward:
                                    (SEQ. ID. NO: 9)
5'-CCCAAGGGAAGTCCTACTTG-3' reverse:
                                    (SEQ. ID. NO: 10)
5'-AGCAACATCCCTCTGTCCAC-3' phd3:
                                    (SEQ. ID. NO: 11)
forward: 5'-CGCTGCGTCACCTGTATT-3' reverse,
                                    (SEQ. ID. NO: 12)
5'-TAGCATACGACGGCTGAACT-3' ef1a:
                                    (SEQ. ID. NO: 13)
forward: 5'-TGCCTTCGTCCCAATTTCAG-3' reverse,
                                    (SEQ. ID. NO: 14)
5'-TACCCTCCTTGCGCTCAATC-3'
```

All PCR reactions were performed in triplicate.

Multiple sequence alignment between human and zebrafish MYDGF. A MUSCLE alignment was generated in Jalview using the protein sequences of mature human MYDGF (UniProtKB accession no. Q969H8; residues V32-L173), mature zebrafish MYDGF (UniProtKB accession no. Q6DGL1; E27-L164; The UniProt Consortium, 2017), and the 22 seed sequences of MYDGF homologues provided in Pfam (Pfam accession no. PF10572). The 80 residues of human MYDGF that were identical to zebrafish MYDGF in the sequence alignment (58% sequence identity) were mapped onto the NMR solution structure of human MYDGF. The structure presented herein was solved using NMR data (Bortnov et al., 2019) to obtain a refined solution structure of human MYDGF that has been subsequently reconciled with the crystal structure (Ebenhoch et al., 2019) as described in (Bortnov, 2020) and deposited under PDB accession no. 6O6W.

Morpholino injections. Splice-blocking morpholinos were designed to the exon 3/intron 3 border and exon 5/intron 5 border of mydgf. Morpholinos were obtained from GeneTools and resuspended in water to a stock concentration of 1 mM. Morpholinos were further diluted to a final concentration of 350 µM, and 3 nl of this injection mix was injected into the yolk sac of zebrafish embryos at the one-cell stage. Morpholino sequences are as follows:

```
mydgf E313 (#1):
                                    (SEQ. ID. NO: 15)
5'-GAGTGTATAAGTTACCTCCATACTG-3' mydgfE5l5 (#2):
                                    (SEQ. ID. NO: 16)
5'-GGAATAGCATATACGCATGCTCACC-3' mismatch control:
                                    (SEQ. ID. NO: 17)
5'-CCTCTTACCTCAGTTACAATTTATA-3'
```

A previously published morpholino targeting arnt-1, 5'-GGATTAGCTGATGTCATGTCCGACA-3' (SEQ. ID. NO: 18) (Prasch et al., 2006), was obtained from GeneTools and resuspended in water to a stock concentration of 1 mM. Morpholinos were further diluted to a final concentration of 500 µM and injected as above.

Generation of a zebrafish mydgf mutant and genotyping. Short guide RNA targeting zebrafish mydgf (ENSDARG00000071679) was designed using CHOPCHOP (Montague et al., 2014). The exon 5 target sequence was 5'-GGCCGTGGGTGGACAGG-3' (SEQ. ID. NO:19). CRISPR-Cas9 gRNA synthesis and injections were performed as previously described (Gagnon et al., 2014). NHGRI-1 embryos were injected in the yolk sac at the one-cell stage with 150 pg short guide RNA and 300 pg Cas9 protein (#CP01-50; PNA Bio). To confirm genome editing, genomic DNA was extracted from 2 dpf larvae and amplified using the following primers:

forward,
(SEQ. ID. NO: 20)
5'-GTAAAACGACGGCCAGTGTGACATTG
ACATTTGCCGCA-3' reverse,
(SEQ. ID. NO: 21)
5'-AGACTCTGACACTATGTACTCT-3'.

The PCR fragments were separated on a 3% agarose gel.

Sequences of F0 mosaic cuts were confirmed by topoisomerase-based cloning (Zero Blunt TOPO PCR Cloning Kit; Thermo Fisher Scientific) and sequencing. Clutches of larvae with confirmed CRISPR cuts were grown to adulthood. Adult F0 CRISPR-injected fish were screened for germline mutations by DNA extraction and topoisomerase-based cloning and sequencing of sperm or eggs from individual fish.

Heterozygous mydgf mutants were obtained by outcrossing the CRISPR mutants to AB WT zebrafish. Offspring were genotyped using genomic DNA obtained from fin clips and amplified using the primers listed above. The PCR product was separated on a 3% agarose gel to determine individual fish genotypes. F2 and/or F3 heterozygotes were in-crossed to generate homozygous mydgf$^{+/+}$ (WT) and mydgf$^{-/-}$ siblings. For experimental purposes, these fish were grown to adulthood and in-crossed to produce clutches of WT and mydgf$^{-/-}$ cousins. These cousins were used only for experiments and not for line maintenance or the production of future generations.

Expression and purification of zebrafish MYDGF. The insert encoding mature zebrafish MYDGF (UniProtKB accession no. Q6DGL1; E27-L164) was amplified by PCR from cloned *Danio rerio* using primers (SEQ. ID. NO: 22)
5'-CTGTGTGGTACCGAAAGGACCAAAACACTGGACTTCG (SEQ. ID. NO: 23)
3'-TAGAGGGCTAGCTCAGAGTTCATCATGCCGTATTCGAC which introduced restriction sites for cloning (5' Kpn1 and 3' Nhe1) into pET.ELMER (Maurer et al., 2010). Sequences were verified before expression in bacteria.

BL21 (DE3) competent cells (#69450; MilliporeSigma) were transformed with the pET.ELMER-zebrafish MYDGF plasmid and protein expression was induced using 1 mM isopropyl β-D-1-thiogalactopyranoside (IPTG) as previously described (Bortnov et al., 2019). The recombinant protein was expressed with an N-terminal polyhistidine tag and thrombin cleavage site (residues MGGSHHHHHHGSLVPRGSKGT; SEQ. ID. NO:24) preceding the mature zebrafish MYDGF sequence. The recombinant protein was extracted in an 8 M urea cell lysis solution and purified by immobilized metal affinity chromatography using nickel-nitrilotriacetic acid resin (#30230; Qiagen) as detailed previously (Bortnov et al., 2019). The protein was then refolded through dialysis against dilute acetic acid (100 mM, then 1 mM; pH 3.7), which removed components of the cell lysis solution and maximized protein solubility. After screening a variety of buffers and pH conditions, we determined that this protein construct was especially insoluble in buffers containing NaCl concentrations above 100 mM and in pH environments above pH 6. The protein was ultimately dialyzed against a pH 6.0 buffer solution containing 10 mM sodium phosphate, 100 mM NaCl, and 0.5 mM dithiothreitol and purified by size-exclusion chromatography on a HiLoad 16/600 Superdex 75 prep grade column (#28-9893-33; Sigma-Aldrich) equilibrated in and eluted with the same buffer. After verification by SDS-PAGE, fractions containing only monomeric zebrafish MYDGF were combined, and the final sample was concentrated using an Amicon Ultra-4 centrifugal filter (#UFC801024; MilliporeSigma).

Antibody production and Western blotting. The zebrafish MYDGF immunogen described above was submitted to Covance Research Products Immunology Services for generation of rabbit anti-zebrafish MYDGF antiserum. Antiserum was exposed to Protein A Sepharose beads overnight at 4° C. to absorb total IgG and then washed in 50 times the bead volume PBS plus 0.1% tween and 0.5% NP-40, and in two times the bead volume PBS only. IgG was eluted with 2×500 µl 100 mM glycine, pH 3.0, and neutralized with 1/10th volume 1 M Tris, pH 8.0. OD at 280 nm was taken for IgG concentration.

For Western blotting, 50-100 2 dpf larvae were pooled and deyolked in calcium-free Ringer's solution with gentle disruption from a p200 pipette tip. Larvae were washed twice with PBS and stored at −80° C. until samples were lysed by sonication in 20 mM Tris, pH 7.6, 0.1% Triton X-100, 0.2 mM PMSF, 1 µg/ml Pepstatin, 2 µg/ml Aprotinin, and 1 µg/ml Leupeptin at 3 µl per larvae while on ice and clarified by centrifugation. Protein concentrations were determined using a bicinchoninic acid protein assay kit (Thermo Fisher Scientific), according to the manufacturer's instructions. Equal amounts of total protein were loaded on 12% SDS-polyacrylamide gels and transferred to nitrocellulose membrane. Affinity-purified total rabbit antizebrafish MYDGF was used at 1:500 dilution. Actin (monoclonal actin AC15; #A5441; Sigma-Aldrich) or β-tubulin (mouse β-tubulin [D3U1W]; #86298; Cell Signaling Technology) was detected for loading control. Western blots were imaged and quantified by normalizing to loading controls with an Odyssey Infrared Imaging System (LI-COR Biosciences). The antibody did not work for immunofluorescence.

MYDGF protein production and injection. HEK293 cells were transfected with zebrafish mydgf-pCS2 or empty pCS2 constructs using Lipofectamine 3000 reagent (#L3000008; Invitrogen) following the manufacturer's protocol. 16-20 h after transfection, cell media was changed to SFM4HEK293 media (HyClone; Thermo Fisher Scientific). 72 h later, media was collected, clarified by centrifugation, and aliquoted and frozen at −80° C. Samples of media were run on 12% SDS-polyacrylamide gels and checked by Western blot and InstantBlue staining (Abcam).

CCM with and without zebrafish MYDGF were mixed at two parts media to one part phenol red. Tricaine-anesthetized 3 dpf WT or mydgf$^{-/-}$ mpx:mCherry zebrafish larvae were injected with 1 nl of the injection mix in the left otic vesicle. At 2 h after injection, larvae were fixed in 4% PFA at 4° C., and the area of the otic vesicle was imaged as described below.

Tail transection of the caudal tail fin. Dechorionated, tricaine-anesthetized 3 dpf larvae were transferred to milk-coated 35-mm plates, washed twice in E3 medium, and wounded in 0.2 mg/ml tricaine/E3 solution. Tail transection was performed using a #10 scalpel blade just distal to the tip of the notochord. Larvae were transferred to zebrafish Wounding and Entrapment Device for Growth and Imaging (ZWEDGI) devices (Huemer et al., 2017), or washed 3 times in E3 medium and allowed to recover at 28.5° C. until live imaging or fixation at indicated times.

Thermal injury of the caudal tail fin. Thermal injury to the caudal fin was performed as previously described (Miskolci et al., 2019). Briefly, a fine tip (type E) of a line-powered thermal cautery instrument (Stoelting) was applied to the distal tip of the tail fin of tricaine-anesthetized larvae in the E3 medium for 1-2 s until the tail fin tissue curled but before injury to the notochord was observed. Following injury, the larvae were transferred to ZWEDGI devices or washed with E3 medium and allowed to recover at 28.5° C. until live imaging or fixation at indicated times.

Otic vesicle injection. 5,000 colony-forming units (CFUs) of $P.$ $aeruginosa$ were microinjected in 1 nl volume as previously described (Harvie and Huttenlocher, 2015). Bacterial suspension (10,000 CFU/nl) was further diluted 1:1 with PBS containing 10% glycerol, 2% PVP-40 (polyvinylpyrrolidine; Sigma-Aldrich), and 0.33% phenol red, to a final concentration of 5,000 CFU/nl. PVP-40 was used to prevent bacterial clumping and phenol red was used to visualize injection success. Tricaine-anesthetized larvae positioned laterally on an angled injection ramp made of 2% agarose in E3 medium (in 10-cm Petri dish) and pretreated with 1 ml filter-sterilized 2% BSA to prevent larval abrasions. 1 nl volume was microinjected into otic vesicle using a thin-walled glass capillary injection needle, with time range set to "millisecond" and pressure set to ~20 PSI on the microinjector. 2 h after injection, larvae were fixed in 4% PFA at 4° C. Larvae were stained by Sudan Black to visualize neutrophils.

Preparation of bacteria. GFP-expressing $P.$ $aeruginosa$ (pMF230) was prepared for microinjection as previously described (Rosowski et al., 2016). A single colony was grown overnight in Miller LB medium (#DSL24400; Dot Scientific) without antibiotics at 37° C. with shaking. In the morning, the culture was diluted 1:5 and grown for an additional 1 h 15 min at 37° C. with shaking. OD at 600 nm was measured to calculate CFUs/nl (OD 1=~2.6×10$^5$ CFUs/ml). Bacterial suspension was pelleted by centrifugation for 30 s at ~21,000×g, washed three times, and resuspended in sterile PBS at 10,000 CFUs/nl.

Sudan Black staining. Larvae were fixed in 4% PFA at 4° C. until staining. Larvae were washed three times in PBS and then incubated for 30 min in Sudan Black B working solution (0.18% stock diluted 1:5 in 70% ethanol; 0.1% phenol). Larvae were washed twice in 70% ethanol. Depigmentation was performed by incubating the larvae in a solution of 1% potassium hydroxide and 1% $H_2O_2$ for 10 min. The larvae were washed and then stored at 4° C. in a solution of 0.1% Tween-20 in PBS.

Neutrophil recruitment assays. 2 dpf morpholino-injected WT AB and mpx:mCherry or 3 dpf WT and mydgf$^{-/-}$ mpx:mCherry zebrafish larvae were wounded by tail transection or thermal injury, or injected with zebrafish MYDGF protein in the otic vesicle, as described above. Larvae were fixed in 4% PFA at 4° C. at 1 and 6 hpw (following tail transection), 3 and 24 hpb (following burn wound) or 2 h after otic vesicle injection. Caudal fins were imaged in PBS at room temperature on a Zeiss Zoomscope (EMS3/SyCoP3; 1× Plan-NeoFluar Z objective; Zeiss) with an Axiocam Mrm charge-coupled device camera using ZenPro 2012 software (Zeiss). For protein injection assays, images of the otic vesicle region were acquired in PBS at room temperature on a spinning-disk confocal (CSU-X; Yokogawa) on a Zeiss Observer Z.1 inverted microscope and an electron-multiplying charge-coupled device Evolve 512 camera (Photometrics), with a Plan-Apochromat 20×/NA 0.8 air objective (5-µm optical sections, 2,355×512 resolution) using ZenPro 2012 software (Zeiss). Neutrophil numbers were counted manually in z-projected images using Zen 2.3 Lite software (Zeiss). Neutrophil numbers were counted in the area distal to the tip of the notochord (tail transections), the area distal to the caudal vessel loop (burn wounds), or within the confines of the otic vesicle (protein injections).

Total neutrophil counts. 2 dpf morpholino-injected WT AB or 3 dpf WT and mydgf$^{-/-}$ mpx:mCherry unwounded zebrafish larvae were fixed in 1.5% formaldehyde (FA; Polysciences) in 0.1 M Pipes (Sigma-Aldrich), 1.0 mM $MgSO_4$ (Sigma-Aldrich), and 2 mM EGTA (1.5% FA solution; Sigma-Aldrich) overnight at 4° C. Images were acquired at room temperature using a spinning-disk confocal microscope as described above (20×/NA 0.8 air objective, 10-µm optical sections, 2×6 tiles, 2,355×512 resolution) using ZenPro 2012 software (Zeiss). Tiles were stitched together, and neutrophils were counted manually in z-projected images using Zen 2.3 Lite software (Zeiss).

Wound-healing assays. Tricaine-anesthetized 3 dpf WT and mydgf$^{-/-}$ larvae were wounded by tail transection or thermal injury, as described above. Larvae were washed three times with E3 medium and allowed to regenerate for 3 d after injury at 28.5° C. During regeneration, larvae were fixed in 4% PFA at 4° C. at 24, 48, and 72 h after injury. Fins were imaged in PBS at room temperature using a Zeiss Zoomscope, as described above. Unwounded, age-matched larval fins were collected and imaged as a developmental control. Regenerate or developmental area of the tail fins was measured from the distal tip of the notochord (tail transection) or the caudal vessel loop (burns) using FIJI image analysis software (Rueden et al., 2017).

To quantify neutrophil contributions to burn regeneration with or without MYDGF, mpx:mCherry-2A-rac2 or mpx:mCherry-2A-rac2D57N larvae (Rosowski et al., 2016) were injected with mydgf-targeting or mismatch control morpholinos as described above and incubated to 2 dpf at 28.5° C. The larvae were then wounded by thermal injury at the caudal fin, washed three times with E3 medium, allowed to regenerate for 24 hpb, and fixed in 4% PFA. Fins were imaged and measured as described above.

Live imaging and image analysis/processing. 3 dpf WT and mydgf$^{-/-}$ mpx:mCherry/mpeg1: GFP larvae were wounded by tail transection or thermal injury, as described above. Larvae were mounted in ZWEDGI devices (in 0.2 mg/ml tricaine/E3 solution and held in place using 1% low-melting point agarose, applied at the head) or embedded in 1% low gelling agarose (Sigma-Aldrich) containing 0.2 mg/ml tricaine in an Ibidi µ-slide two-well glass bottom chamber (Ibidi). Images of the caudal fin region were acquired at room temperature using a spinning-disk confocal microscope (10×/NA 0.3 or 20×/NA 0.8 air objective, 5-µm optical sections, one z-stack every 2.5 min for 3 or 6 h at indicated times following injury). 3D cell tracking was performed using Imaris image analysis software (Bitplane). Leukocytes were tracked using the "Spots" function, where spot size was defined as a range of 12-15 µm. Individual tracks were curated after software detection. Tracks were then filtered according to the following criteria to eliminate false tracks and tracks showing only vibrational or nonprogressive movement; short tracks comprising fewer than five spots for neutrophils, tracks with a total displacement length of less than 14 µm (neutrophils), and tracks with a mean track speed of 0 µm/s were eliminated. For experiments comparing neutrophil instantaneous speed with position relative to the notochord, the x-position of each spot over the course of the track is normalized to the x-position of the tip of the notochord for the individual larva being measured. For experiments quantifying neutrophil-macrophage contact, the absolute number of neutrophils and macrophages for each frame was normalized using the formula # of contacts×number of neutrophils/number of macrophages.

Dendra2 photoconversion. 3 dpf WT or mydgf$^{-/-}$ mpx:dendra larvae were wounded by tail transection or thermal injury, as described above. Tricaine-anesthetized larvae were mounted in ZWEDGI devices and held in place using 1% low melting point agarose, applied to the head. An imaging sequence was performed on each larva comprising an initial z-stack of the caudal fin area, followed by photoconversion of the neutrophils caudal to the tip of the notochord (tail transection) or vessel loop (burn wounds) and second z-stack of the caudal fin area after photoconversion. The photoconversion and associated imaging sequences were performed at room temperature using a laser-scanning confocal microscope (FluoView FV-1000, 20×/NA 0.75 air objective; Olympus). The following stimulation settings were used for photoconversion: 40% 405 nm laser transmissivity, 10 μs/pixel dwell time, and 45 s total stimulation time. Photoconversion was performed at 2 hpw for tail transections and 4 hpb for burn wounds. Larvae were maintained in E3 medium in individual wells of a 96-well plate at 28.5° C. until final imaging.

At 6 hpw (tail transections) or 24 hpb (burn wounds), larvae were fixed in 1.5% FA solution overnight at 4° C. Larvae were then mounted in 1% low-melting-point agarose, and images of the tail region were acquired using a spinning-disk confocal microscope, as described above for neutrophil recruitment assays. Photoconverted (red) and nonphotoconverted (green) neutrophils in the area distal to the tip of the notochord (tail transections) or distal to the vessel loop (burn wounds) were counted manually using FIJI image analysis software (Rueden et al., 2017).

Quantification of apoptosis. Immunostaining to identify apoptotic (active caspase-3 positive) neutrophils was performed using 3 dpf WT or mydgf$^{-/-}$ mpx:mCherry larvae. Larvae wounded by tail transection were fixed at 6 hpw in 4% PFA at 4° C. overnight and then stored in methanol at −20° C. until immunostaining. Larvae were incubated with monoclonal rabbit anti-active caspase-3 antibody (#559565; BD Biosciences) at 1:200 in block (PBS, 1% DMSO, 1% BSA, 0.05% Triton X-100, and 1.5% goat serum), followed by incubation with Alexa Fluor 488 donkey anti-rabbit secondary antibody (Thermo Fisher Scientific). The caudal fin area was then imaged at room temperature in PBS using a spinning-disk confocal microscope, as described above (20×/NA 0.8 air objective, 5-μm optical sections). Apoptotic neutrophils were defined as discrete spots in the area distal to the tip of the notochord expressing both red (neutrophil) and green (active caspase-3) fluorescence. Apoptotic neutrophils were counted manually using Zen 2.3 Lite software (Zeiss).

Macrophage depletion. Macrophage depletion was performed by injection of clodronate liposomes. At 2 dpf, anesthetized (Tg(mpeg1:GFP)) larvae were injected intravenously via the posterior caudal vein with 1 nl liposome-encapsulated clodronate (www.clodronateliposomes.org) or PBS. The clodronate liposome-injected fish were sorted for GFP-negative (macrophage depleted) larvae. Thermal injury of the caudal fin was performed on GFP-negative larvae, along with PBS liposome-injected controls at 3 dpf. The wound healing of larvae was monitored over time by live imaging at room temperature in 0.2 mg/ml tricaine/E3 medium at 1, 2, 3, and 4 d after burn on a Zeiss Zoomscope (EMS3/SyCoP3; 1× Plan-NeoFluar Z objective; Zeiss) with an Axiocam Mrm charge-coupled device camera using ZenPro 2012 software (Zeiss). Tail fin regrowth area was then measured for each larva as described above.

Statistical analyses. Independent biological replicate is defined as a separate clutch of larvae spawned on different days. RT-qPCR gene expression analyses comprised three to five independent biological replicates, and reactions were performed in three technical replicates. Statistical significance was determined by comparing the calculated $\Delta$Cq of the experimental conditions using the nonparametric Wilcoxon two-group test. Fold change in $\Delta$Cq was calculated and plotted in terms of mean with 95% confidence interval (CI). Neutrophil quantification and migration analyses and regeneration assays comprised three or four biological replicates. Replicate numbers are noted in the figure legends. Experimental conditions were compared using analysis of variance. Comparisons between two groups were performed using an unpaired, two-tailed t test. Data distribution was assumed to be normal, but this was not formally tested. For quantification of neutrophil instantaneous speed over position, a linear mixed effect regression model was used. Genotype and position were treated as fixed effects, with experimental replicate, fish, and neutrophil (within fish) treated as random effects. Statistical analyses were performed in R version 3.5.1 (www.r-project.org) using the associated lme4 package. Reported P values are two sided, and the level of statistical significance was preset to 0.05, with no adjustment for multiplicity.

Overview:

The method disclosed herein was elucidated by asking the question "How does inflammation resolve?" The inventors identified a new mechanism of inflammation resolution immediately by neutrophil reverse migration. This has broad implications to inflammatory disease including high fat diet-induced inflammation.

While not being bound to a specific underlying biological mechanism or phenomenon, the reduction in inflammation resulting from increasing the concentration of MYDGF at a wound site (cut, laceration, etc.) or burn site is caused by a neutrophil reverse migration, including chemokine regulation and a macrophage-mediated neutrophil reverse migration.

The structure of human and zebrafish MYDGF is very similar. As reported herein, a MYDGF-negative zebrafish mutant was made by CRISPER mutagenesis. It is shown herein that neutrophil inflammation was increased at wounds and burns in the MYDGF-negative mutant. Moreover, injecting cell lysates comprising MYDGF into the MYDGF-negative zebrafish significantly reduced neutrophil inflammation rescued the original phenotype of the mutant. It has further been established herein that wound sites depleted of neutrophils heal faster and more completely than in subject where neutrophil migration is left unimpeded. In short, as shown herein, regeneration of healthy tissue is impaired in MYDGF-negative mutants. Adding exogenous MYDGF functions to deplete neutrophils and the wound site—thus showing that the impaired regeneration seen in the MYDGF-negative mutant is mediated by neutrophils.

Thus, disclosed herein is a method to inhibit neutrophil recruitment to damaged tissue in a vertebrate subject. The method comprising administering to a vertebrate subject, the subject having a wound and/or a burn at a site on the subject, an amount of exogenous myeloid-derived growth factor ("MYDGF"), a biologically active fragment thereof, or an analogous sequence thereof, wherein the amount is effective to inhibit neutrophil recruitment to the wound and/or burn site.

Figure 1B:
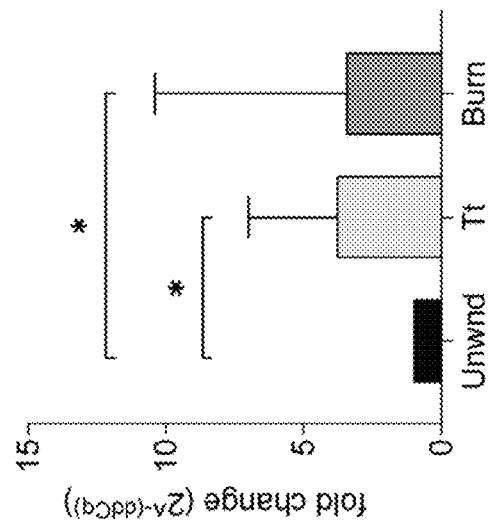
Figure 1C:
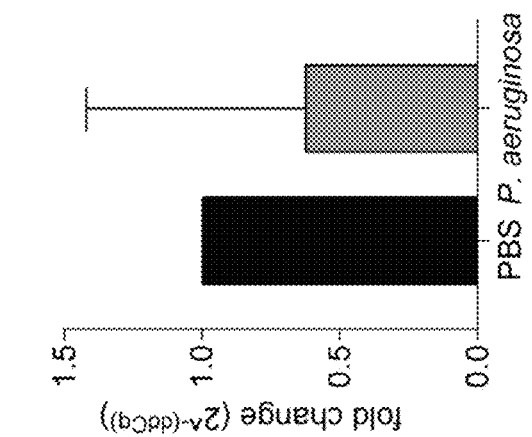

Neutrophil Migration and Reverse Migration:

Neutrophils are the first responders to tissue damage and are critical for mediating host defense to infection. However, excess neutrophil inflammation can also impair tissue repair. As shown by Mathias et al. 2006, neutrophils migrate to a sterile injury in live zebrafish. Neutrophil inflammation resolves via a reverse migration of neutrophils into the vasculature (Yoo et al., 2011). It is known that macrophages help resolve inflammation by inducing neutrophils to leave wounded tissue (Tauzin et al., 2014). Here, using real-time imaging, we show that MYDGF is a damage signal that influences neutrophil behavior in response to tissue damage signaling, but not microbial cues. The findings suggest that MYDGF functions as a newly identified inhibitor of neutrophils that promotes wound healing in larval zebrafish by providing a brake on neutrophil inflammation.

mydgf expression is increased at wounds. We sought to identify factors that are increased by tissue damage, but not infection. Using translating ribosomal affinity purification gene expression analysis (Houseright et al., 2020), we found that mydgf is up-regulated in both neutrophils and macrophages in response to tail fin wounding (FIG. 1A). In addition, mydgf expression was increased approximately fourfold in tail fins following two different types of tail fin injury, tail transection and thermal injury (FIG. 1B). However, we detected no difference in mydgfexpression in otic injection of Pseudomonas aeruginosa (FIG. 1C), suggesting that mydgf expression is regulated by sterile injury, but not infection. These results suggest that up-regulation of mydgf is a common response to sterile tissue injury.

Figure 2A:
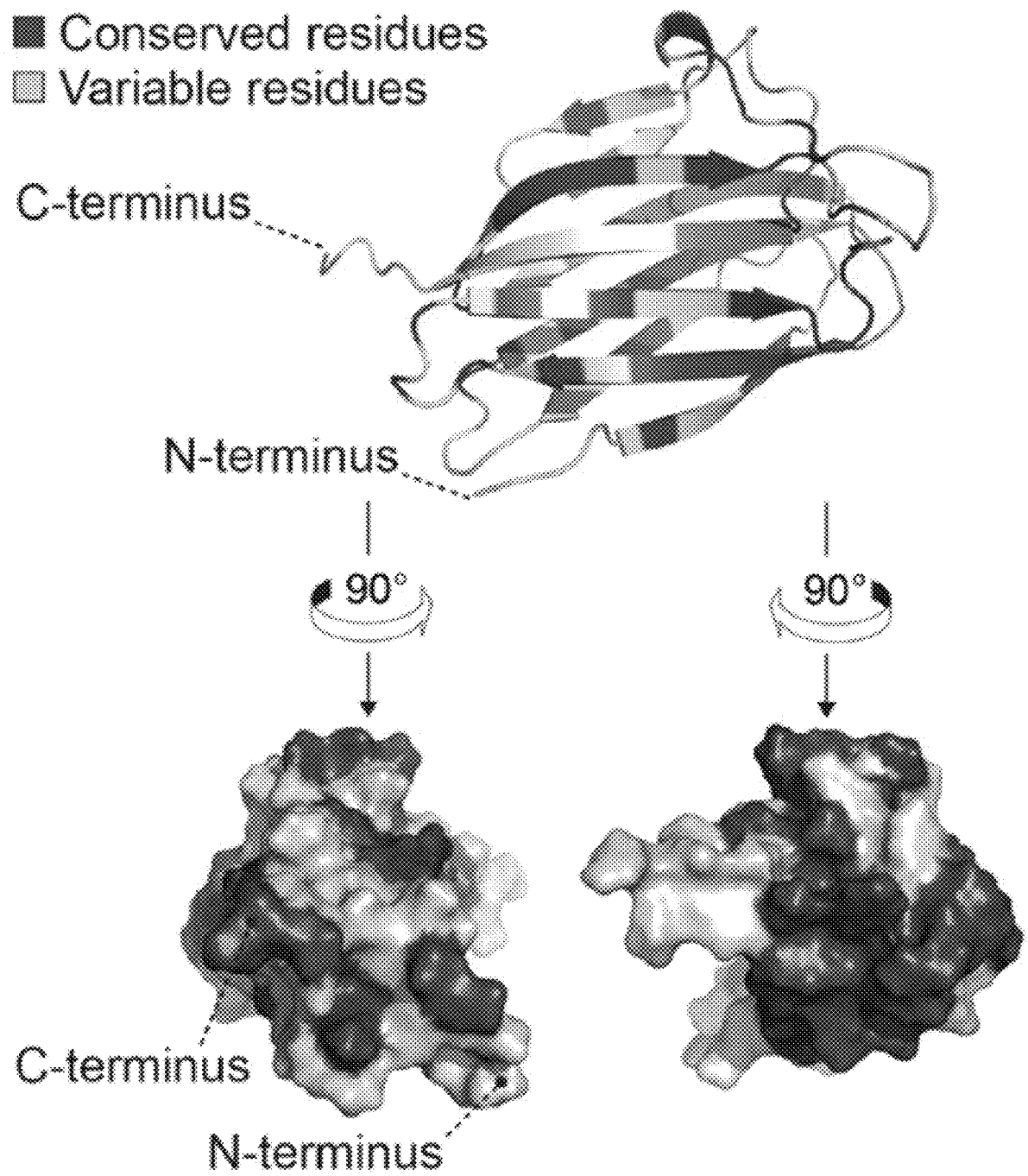
Figure 2D:
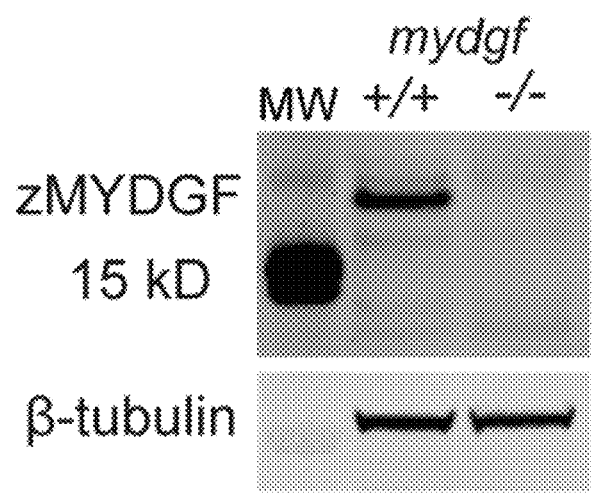

MYDGF regulates neutrophil responses to tissue damage, but not infection. MYDGF is highly conserved (53% amino acid identity and 79% similarity) between zebrafish and humans. Mapping the conserved residues onto the nuclear magnetic resonance (NMR) structure of human MYDGF (PDB accession no. 6O6W) reveals a near-complete conservation of the protein face opposite the N and C termini (FIG. 2A). To characterize the role of MYDGF during wounding, we generated a zebrafish mydgf mutant using CRISPR-Cas9 gene editing, targeting exon 5 of mydgf and resulting in a 12-bp deletion (FIGS. 2B and 2C). mydgf homozygous mutants (mydgf$^{-/-}$) displayed loss of MYDGF protein by immunoblotting at 3 d postfertilization (dpf; FIG. 2D). We found that MYDGF-deficient zebrafish had no gross morphological defects and homozygous incrosses yielded normal larval growth (data not shown), suggesting that MYDGF is dispensable for normal development.

Figure 2E:
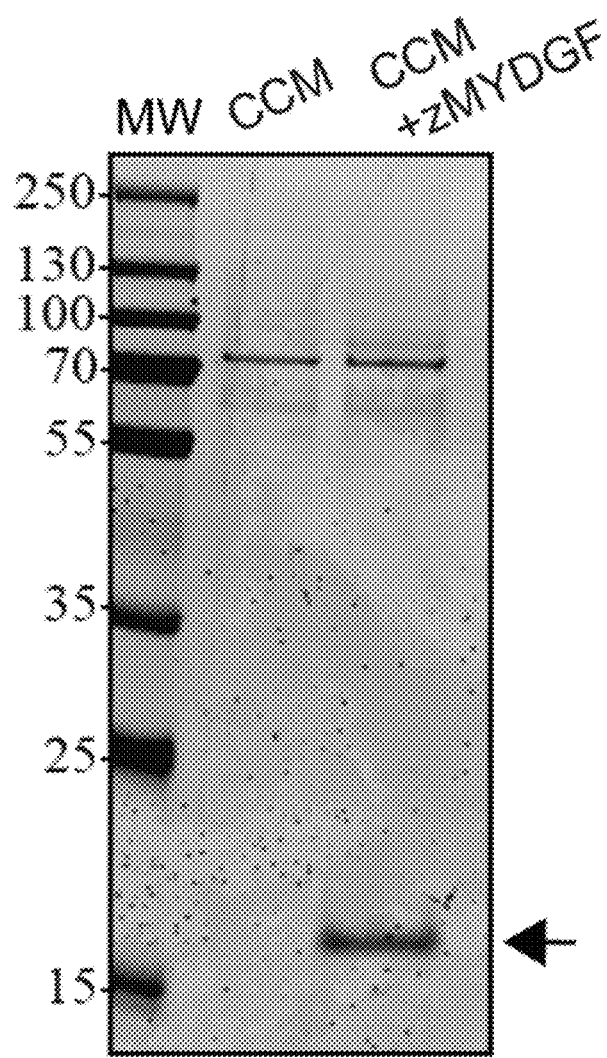
Figure 2G:
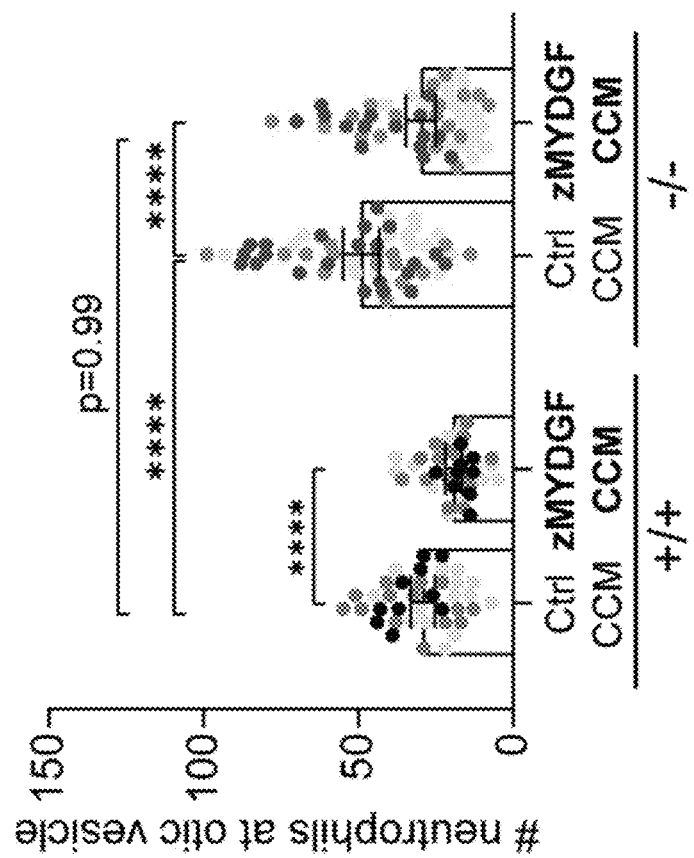
Figure 2F:
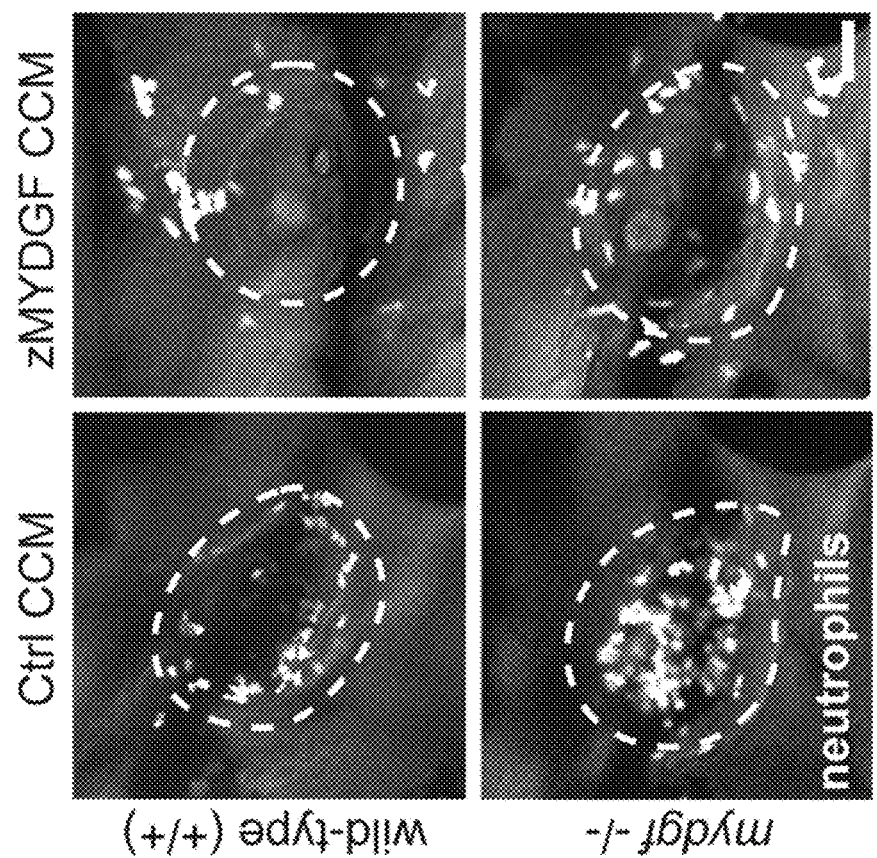

Next, we tested whether otic injury or administration of exogenous MYDGF altered neutrophil recruitment in WT and MYDGF-deficient larvae. Media from HEK293 cells transfected with zebrafish mydgf(mydgf-pCS2) showed secretion of MYDGF into the cell-conditioned media (CCM), as confirmed by immunoblotting (FIG. 2E). Injection of control CCM showed increased neutrophil recruitment to the wound in the otic space in mydgf$^{-/-}$ larvae compared with control (FIGS. 2F and 2G), suggesting that endogenous MYDGF inhibits neutrophil infiltration. Injection of zebrafish MYDGF into the otic vesicle of WT larvae decreased neutrophil recruitment to the injury compared with larvae injected with control CCM, indicating that exogenous MYDGF is sufficient to inhibit neutrophil recruitment. Moreover, injection of MYDGF into the otic space of mutant larvae rescued the increased neutrophil accumulation (FIGS. 2F and 2G). Together, these findings show that depletion of MYDGF increases neutrophil recruitment to damaged tissues and that addition of exogenous MYDGF is sufficient to rescue the phenotype.

Figure 2I:
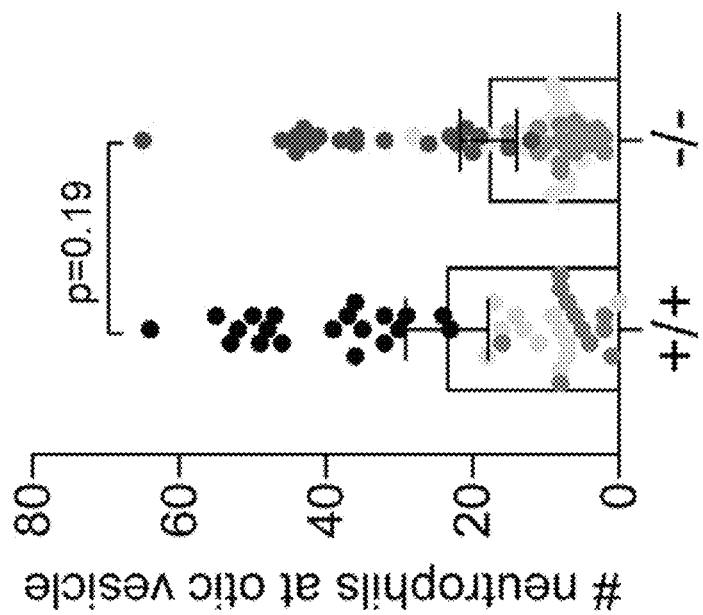
Figure 2H:
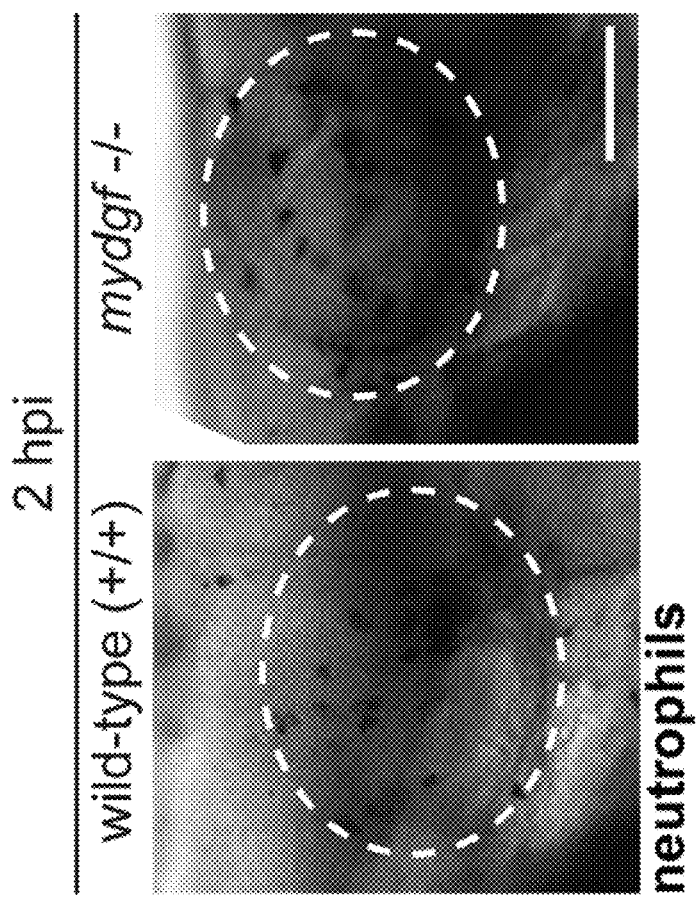

To determine if MYDGF regulates neutrophil recruitment to infection, we injected P. aeruginosa into the otic space, an established model of localized infection, and quantified neutrophil recruitment using Sudan Black staining (Deng et al., 2011). We found that depletion of MYDGF had no effect on neutrophil recruitment to P. aeruginosa (FIGS. 2H and 2I). Taken together, our findings suggest that MYDGF limits neutrophil recruitment to tissue damage, but not infection.

Figures 3A, 3B:
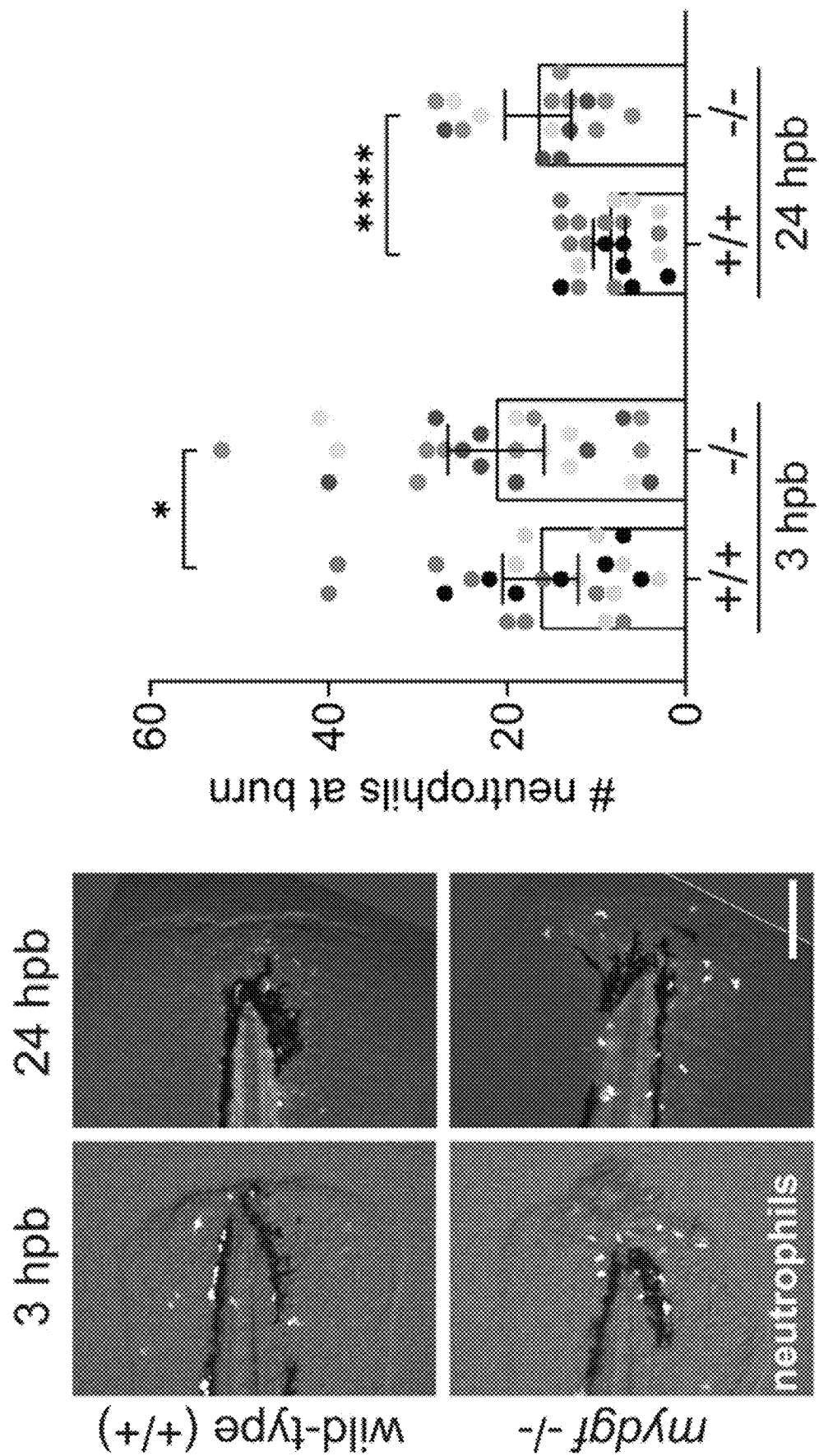
FIGS. 3A-3F. MYDGF depletion leads to a neutrophil-dependent defect in wound healing.
Figures 3C, 3D:
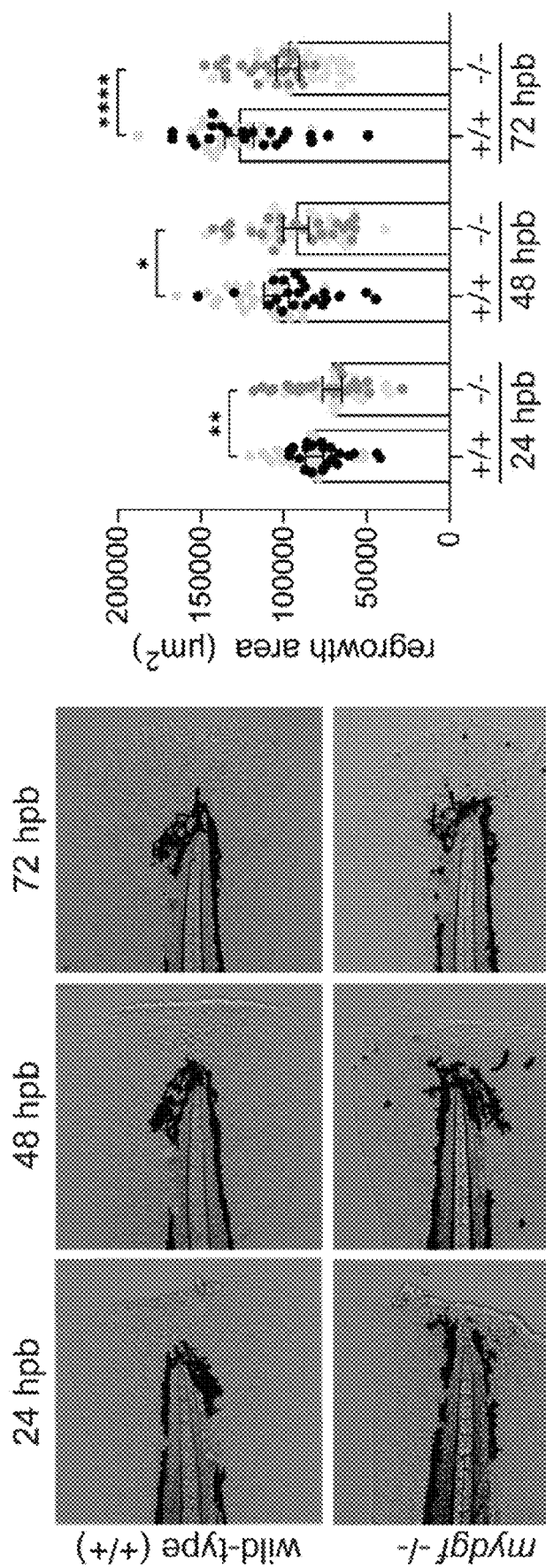
Figures 3E, 3F:
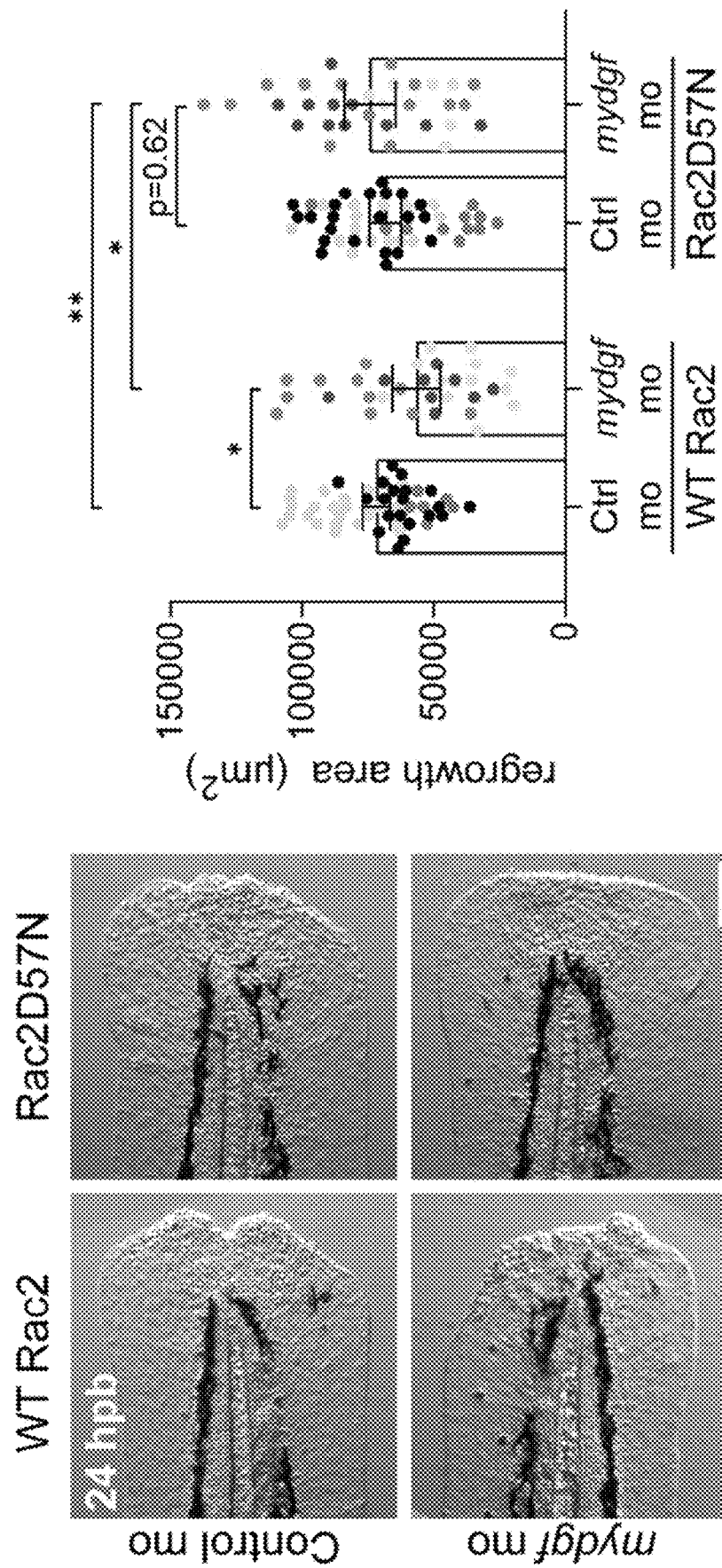
Figure 4A:
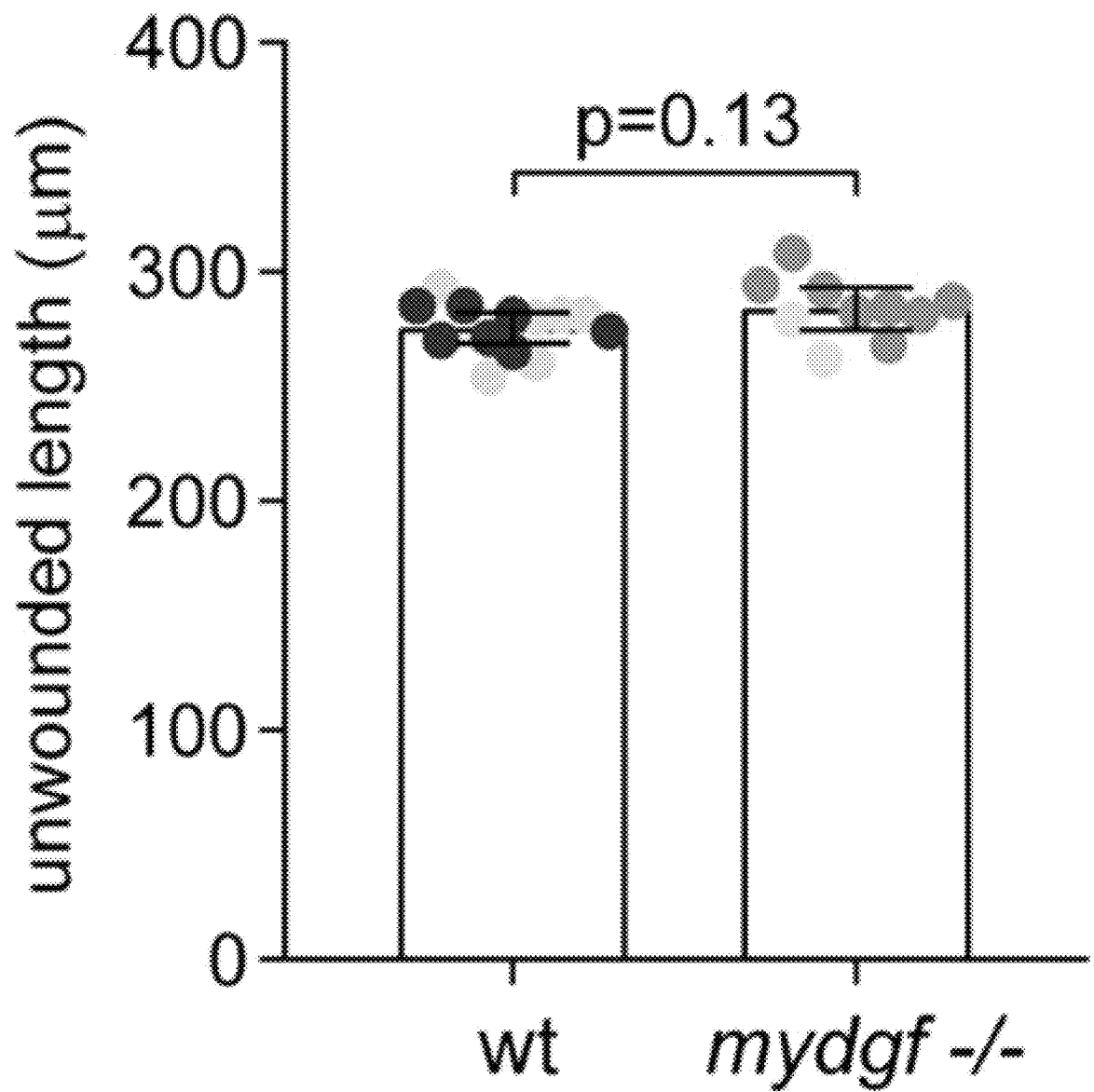
Figure 4B:
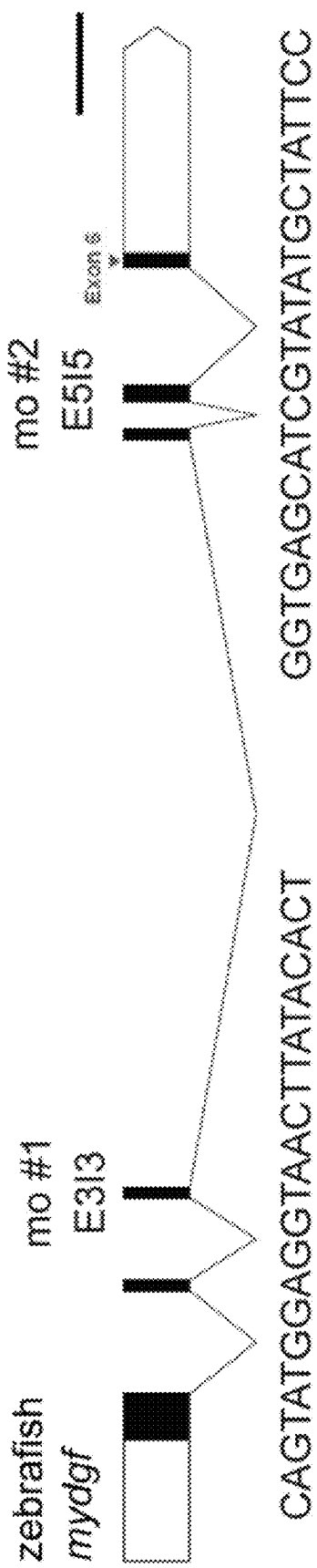
Figure 4D:
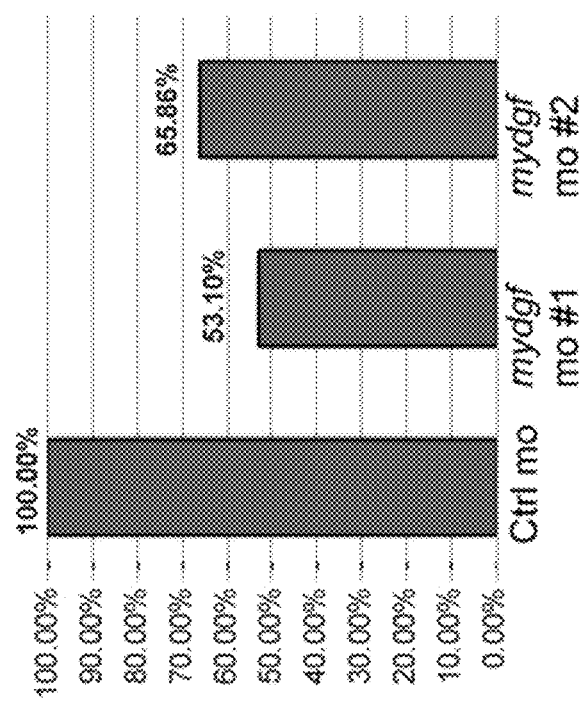
Figure 4C:
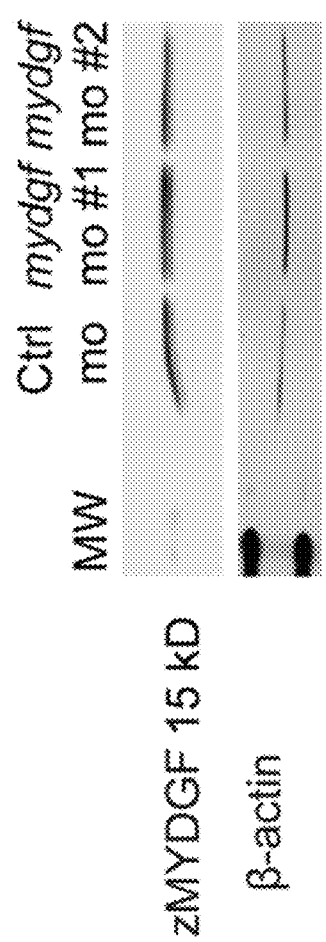
Figure 4H:
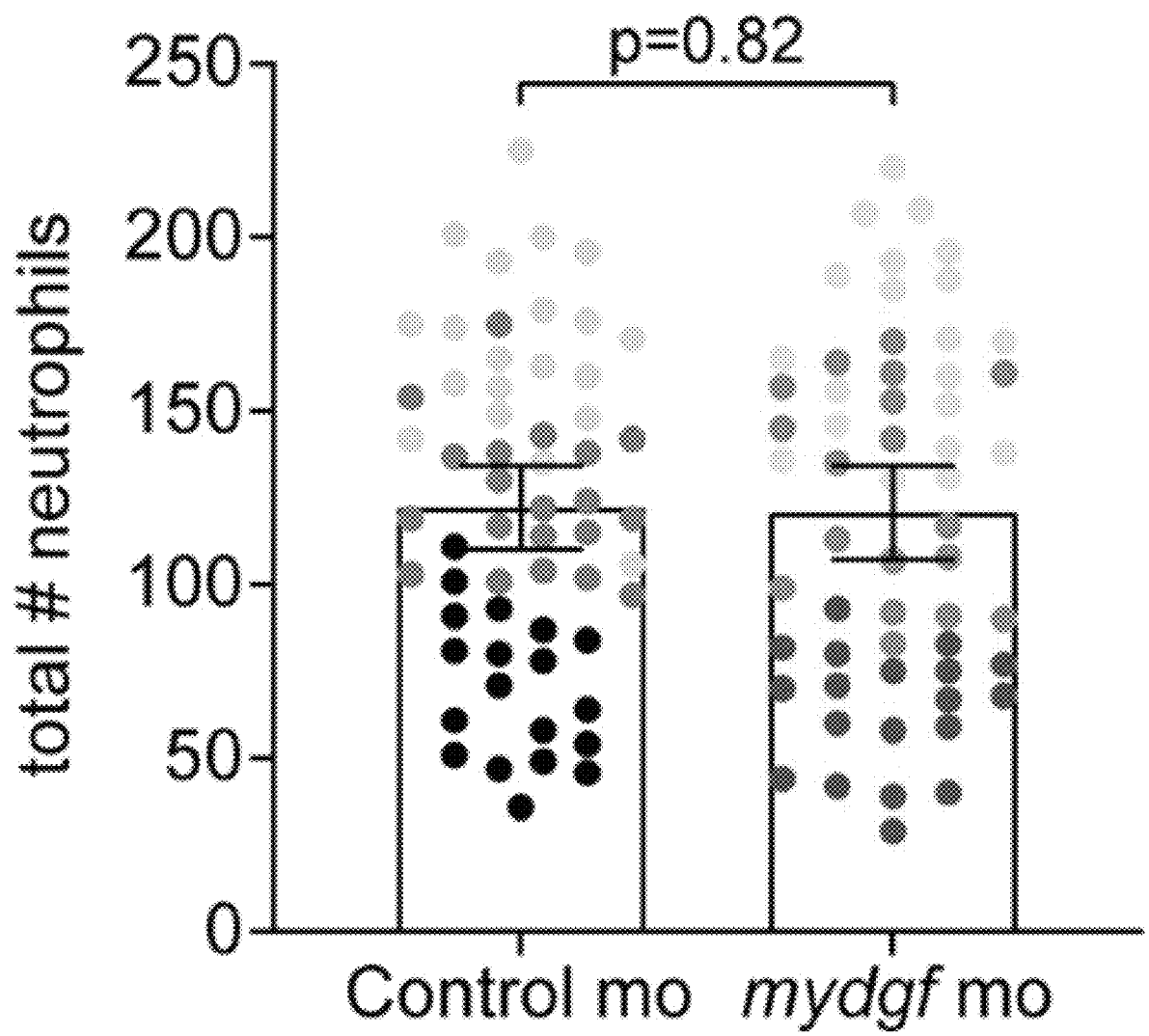

MYDGF-deficient larvae have a neutrophil-dependent defect in tail fin regeneration. Neutrophils impair wound healing in some contexts (BarrosBecker et al., 2020; Brubaker et al., 2013; Ebaid, 2014). Therefore, next we asked whether mydgf$^{-/-}$ larvae have altered tail fin regeneration in response to thermal injury, a model where the presence of neutrophils impairs wound healing (Barros-Becker et al., 2020). We found that MYDGF-deficient larvae had increased neutrophil recruitment to thermal injury at both 3 and 24 h postburn (hpb; FIGS. 3A and 3B), consistent with our findings with otic injury (FIG. 2G). We also observed impaired wound healing of the tail fin following thermal injury at 24, 48, and 72 hpb (FIGS. 3C and 3D). This change is a specific defect in wound healing, as mydgf$^{-/-}$ larvae are developmentally similar to WT larvae and do not show a decrease in tail length in the absence of injury (FIG. 4A). To determine if neutrophils mediate the impaired regeneration in MYDGF-deficient larvae, we depleted neutrophils from the wound using an established transgenic zebrafish expressing a dominant inhibitory Rac2 mutation (Rac2D57N) in neutrophils that renders neutrophils migration impaired (Deng et al., 2011). Control and Rac2D57N larvae were injected with either control morpholino oligonucleotides (mo) or mo targeting mydgf. Transient depletion of mydgf (FIG. 4B) resulted in a 35-45% decrease in mydgf expression (FIGS. 4C and 4D) and increased neutrophil infiltration at wounds compared with control (FIGS. 4E-4G), with no effect on total neutrophil numbers (FIG. 4H). Mo-mediated depletion of mydgf impaired regeneration in control larvae but had no effect on tail fin regeneration in the Rac2D57N larvae (FIGS. 3E and 3F). Together, these data show that depletion of MYDGF impairs regeneration and that this defect is due, at least in part, to the presence of neutrophils at the wound.

Figure 5D:
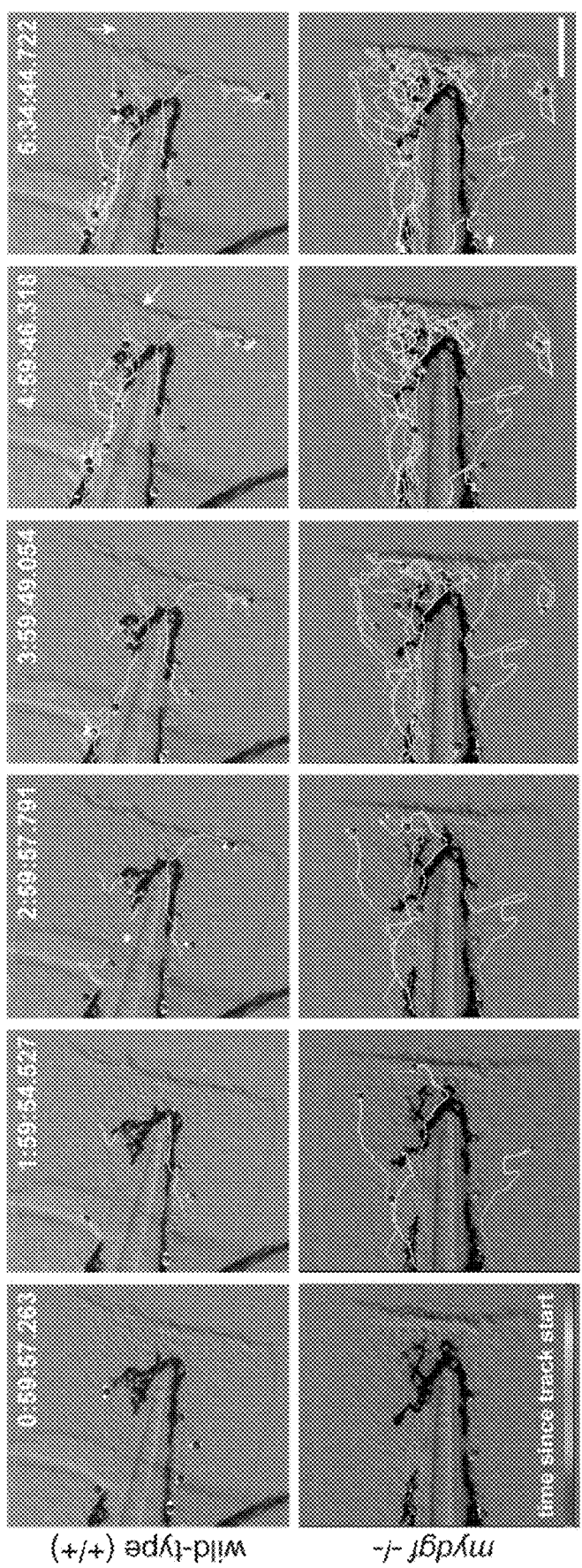
Figure 5F:
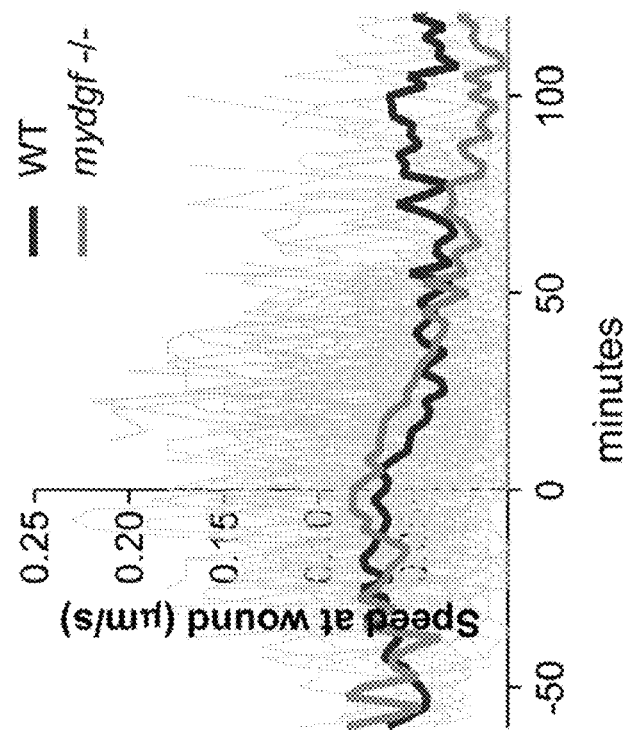
Figure 5E:
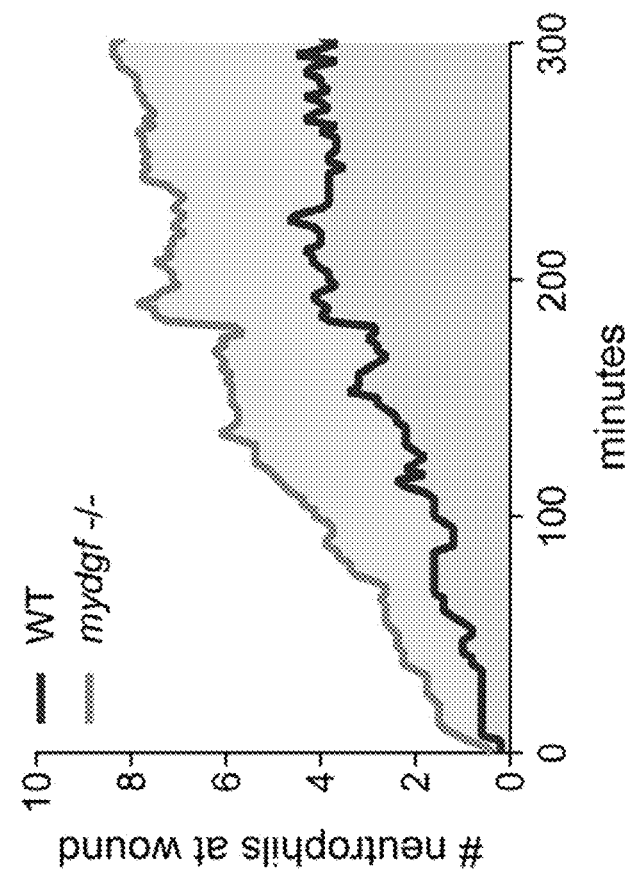

MYDGF-deficient larvae have altered neutrophil motility in the wound microenvironment. We imaged neutrophil recruitment in response to tissue damage to determine the effects of MYDGF on neutrophil behavior in the wound microenvironment. Neutrophil infiltration was also increased at tail transection wounds at 1 and 6 h post-wound (hpw) in MYDGF-deficient Tg(mpx:mCherry) larvae, with no change in total neutrophils (FIGS. 5A-5C). To characterize the mechanism of persistent neutrophil inflammation, we imaged neutrophil behavior in the wound microenvironment and found that mydgf$^{-/-}$ larvae recruited more neutrophils to tissue damage, and these neutrophils remained in the wound microenvironment for a longer duration (FIGS. 5D and 5E). We analyzed the instantaneous speed of each neutrophil as they entered and left the wound microenvironment and found that after entering the wound, neutrophils slowed down in both WT and mutants; however, neutrophils in WT, but not mutants, increased their speed at later time points. Within an hour of reaching the wound, neutrophils in WT larvae moved faster, with speeds approaching those at their entry into the wound, while neutrophils in mydgf$^{-/-}$ larvae maintained slow speeds (FIG. 5F). These findings suggest that neutrophil behavior is different in MYDGF-deficient larvae, resulting in the retention of neutrophils in the wound microenvironment.

Figures 6A, 6B, 6C:
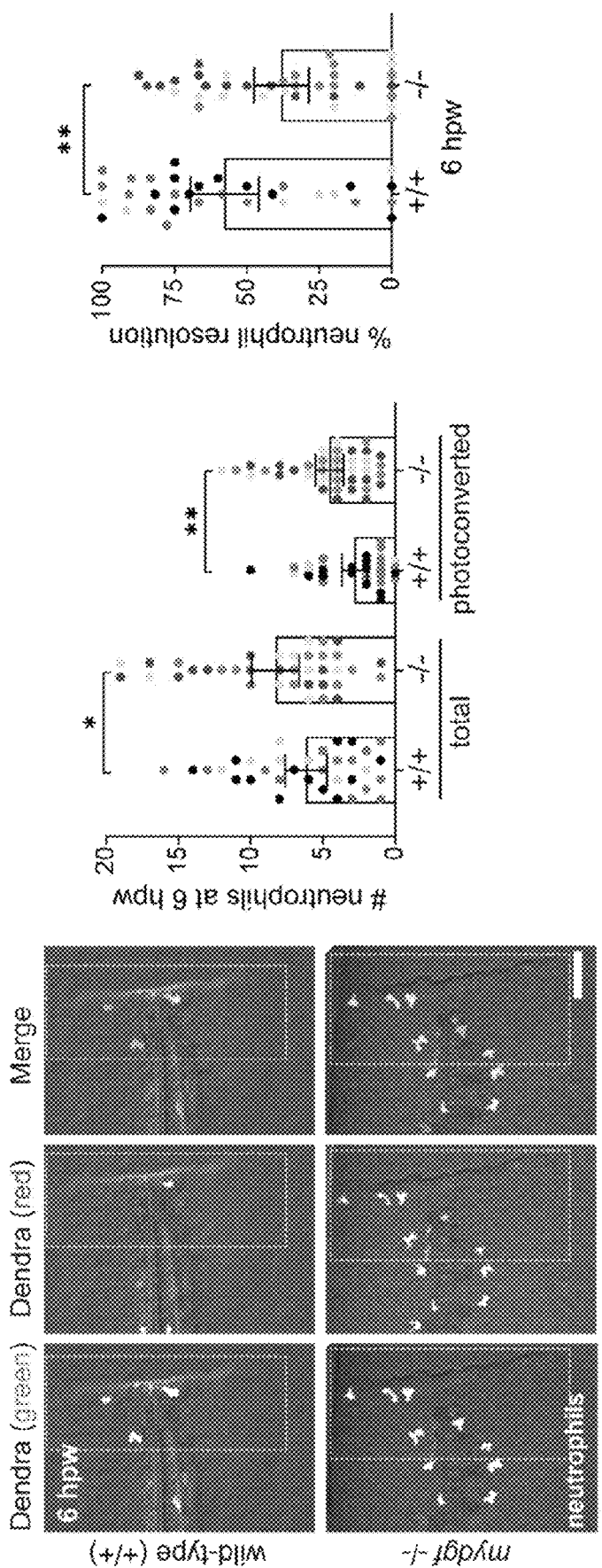
Figures 7A, 7B:
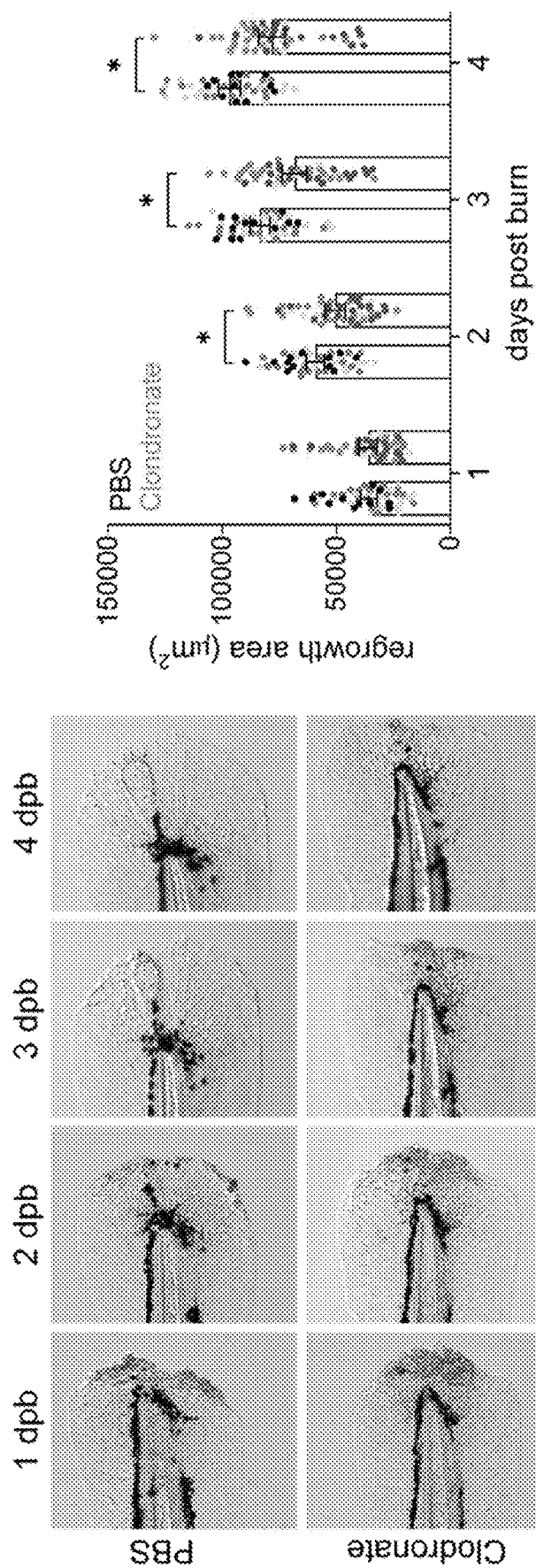
FIGS. 7A-7F. Macrophage responses at sterile injuries in response to MYDGF depletion.
Figure 7D:
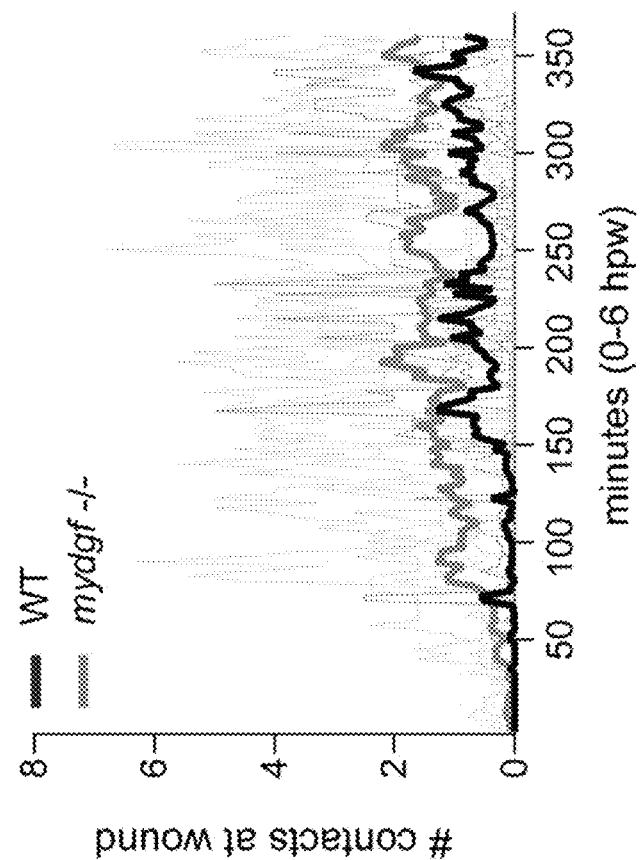
Figure 7C:
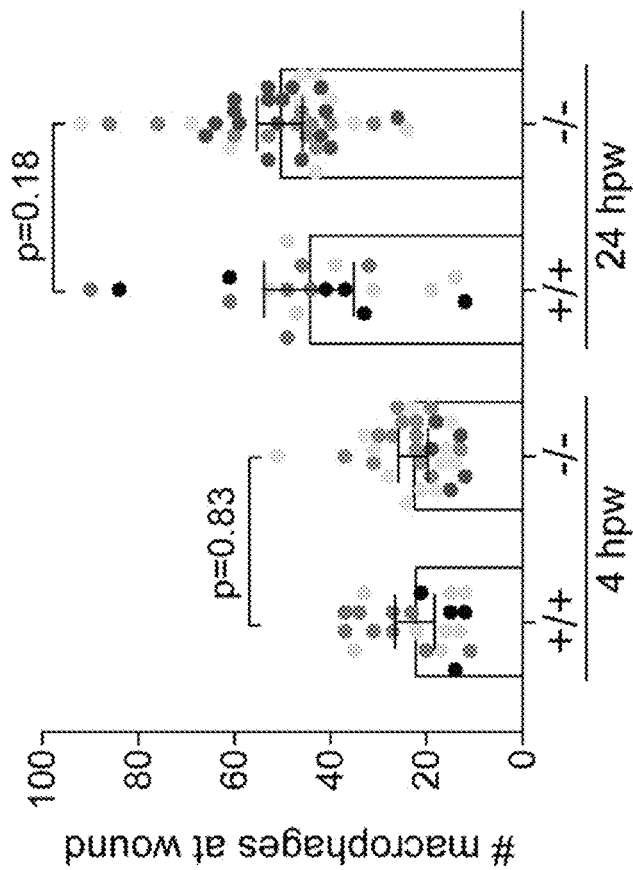
Figure 7F:
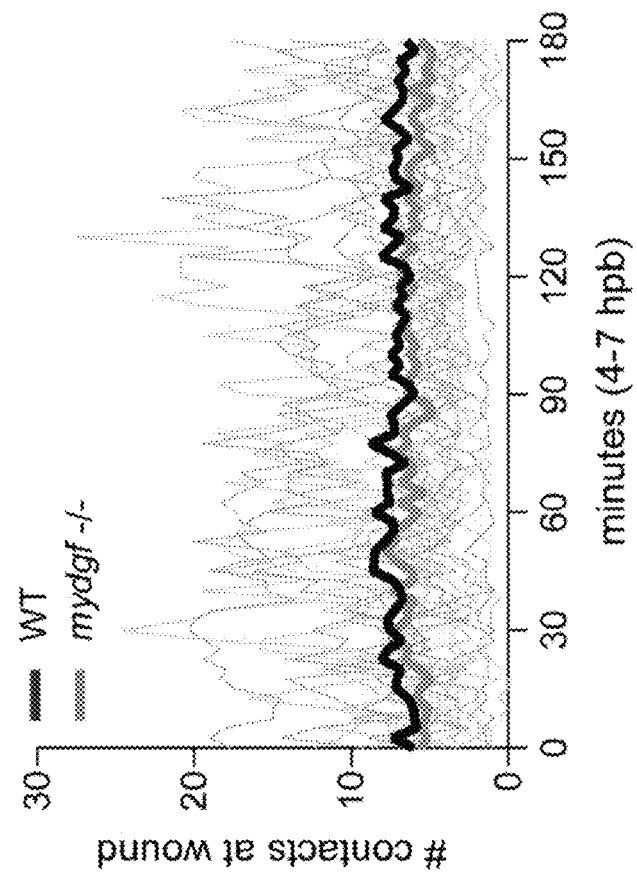
Figure 7E:
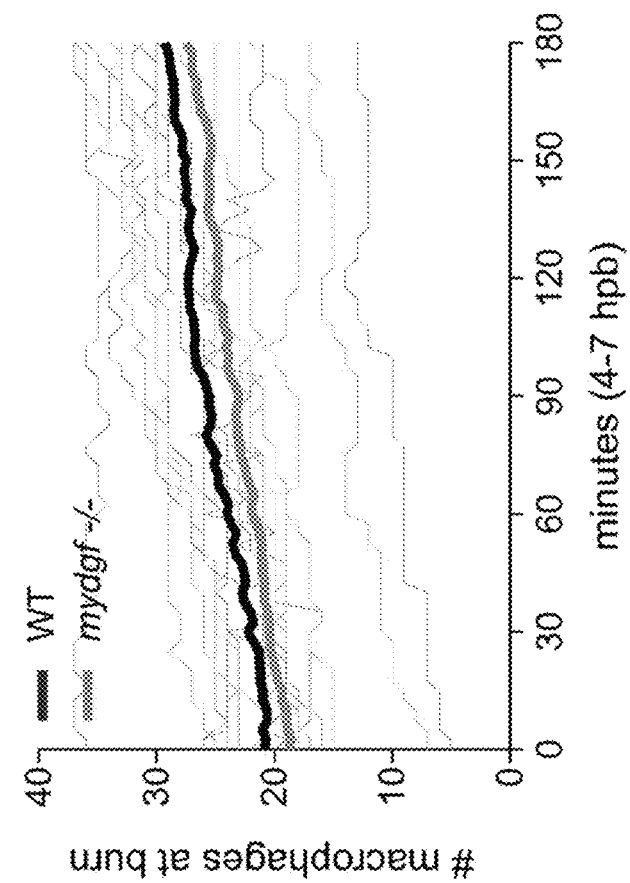

MYDGF-deficient larvae have impaired neutrophil reverse migration and resolution, without changes in macrophages. Neutrophil reverse migration is an important mechanism of inflammation resolution at sterile injury (Mathias et al., 2006; Wang et al., 2017). To determine whether the defect in inflammatory resolution in mydgf$^{-/-}$ larvae was due to impaired neutrophil reverse migration, we used the dendra2 photoconversion system to track neutrophil fate (Yoo and Huttenlocher, 2011). Neutrophils at the wound were photoconverted at 2 hpw, and the photoconverted neutrophils at the wound were quantified at 6 hpw (FIGS. 6A and 6B). We found that mydgf$^{-/-}$ larvae had increased numbers of both newly arrived neutrophils and lingering photoconverted neutrophils at the wound compared with WT larvae (FIGS. 6A and 6B). Furthermore, mydgf$^{-/-}$ larvae had significantly decreased resolution of neutrophils from the wound compared with WT larvae (FIG. 6C). This defect in inflammatory resolution is also evident following the more robust thermal injury, with decreased resolution of neutrophils from the burn wound at 24 hpb (FIGS. 6D-6F). Importantly, we did not observe a change in neutrophil apoptosis at the wound using caspase-3 staining (FIGS. 6G-6I). Although macrophages mediate regeneration (FIGS. 7A and 7B), we did not observe altered macrophage recruitment or neutrophil-macrophage interactions (Tauzin et al., 2014) at wounds in mydgf mutants (FIGS. 7C-7F). Together, these data suggest that the accumulation of neutrophils in the wound in the MYDGF-deficient larvae is due to both increased recruitment of neutrophils and impaired neutrophil reverse migration.

Figure 8A:
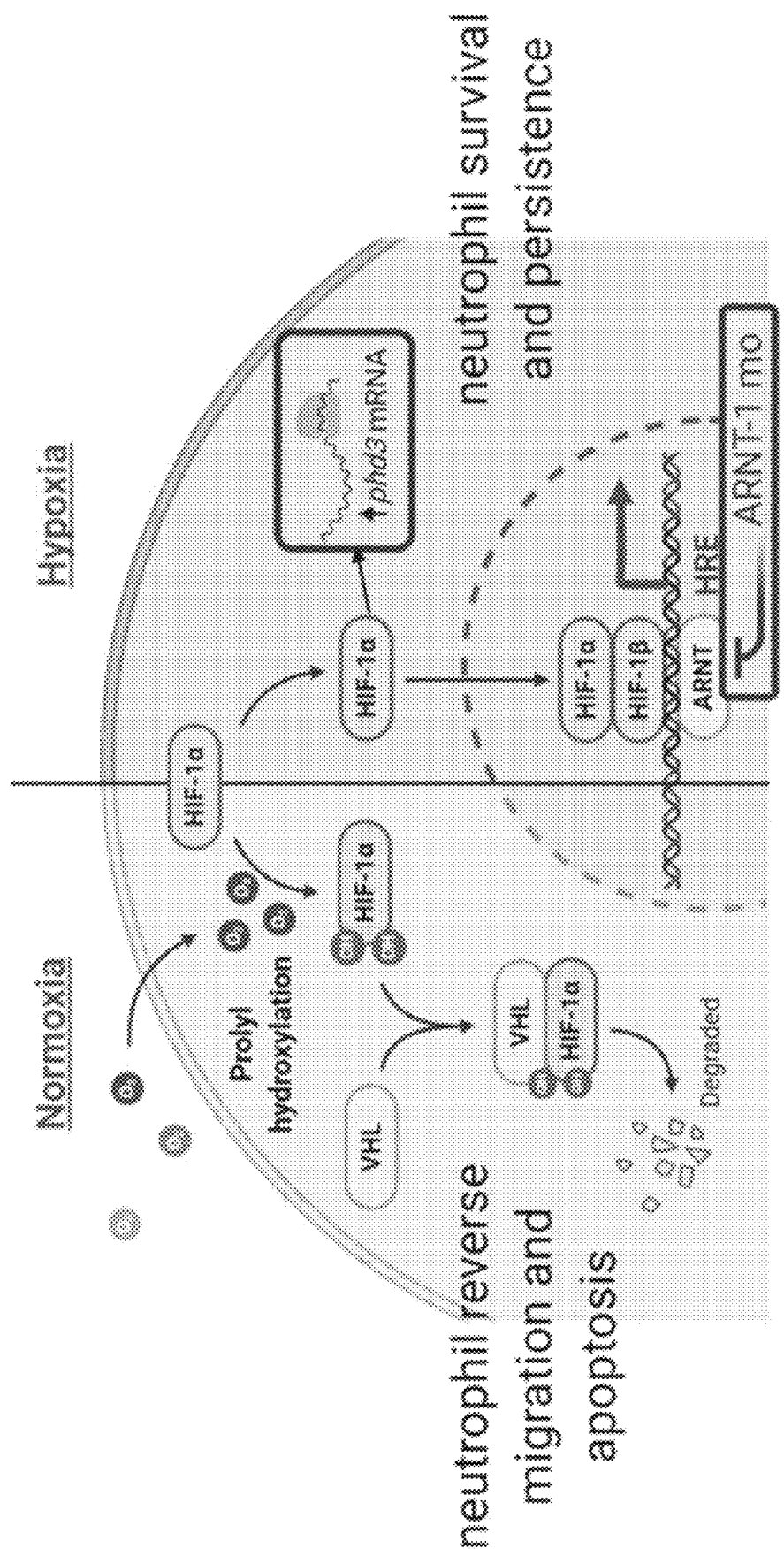
FIGS. 8A-8D. Neutrophil accumulation in the mydgf mutant is dependent on the HIF-1α pathway.
Figure 8B:
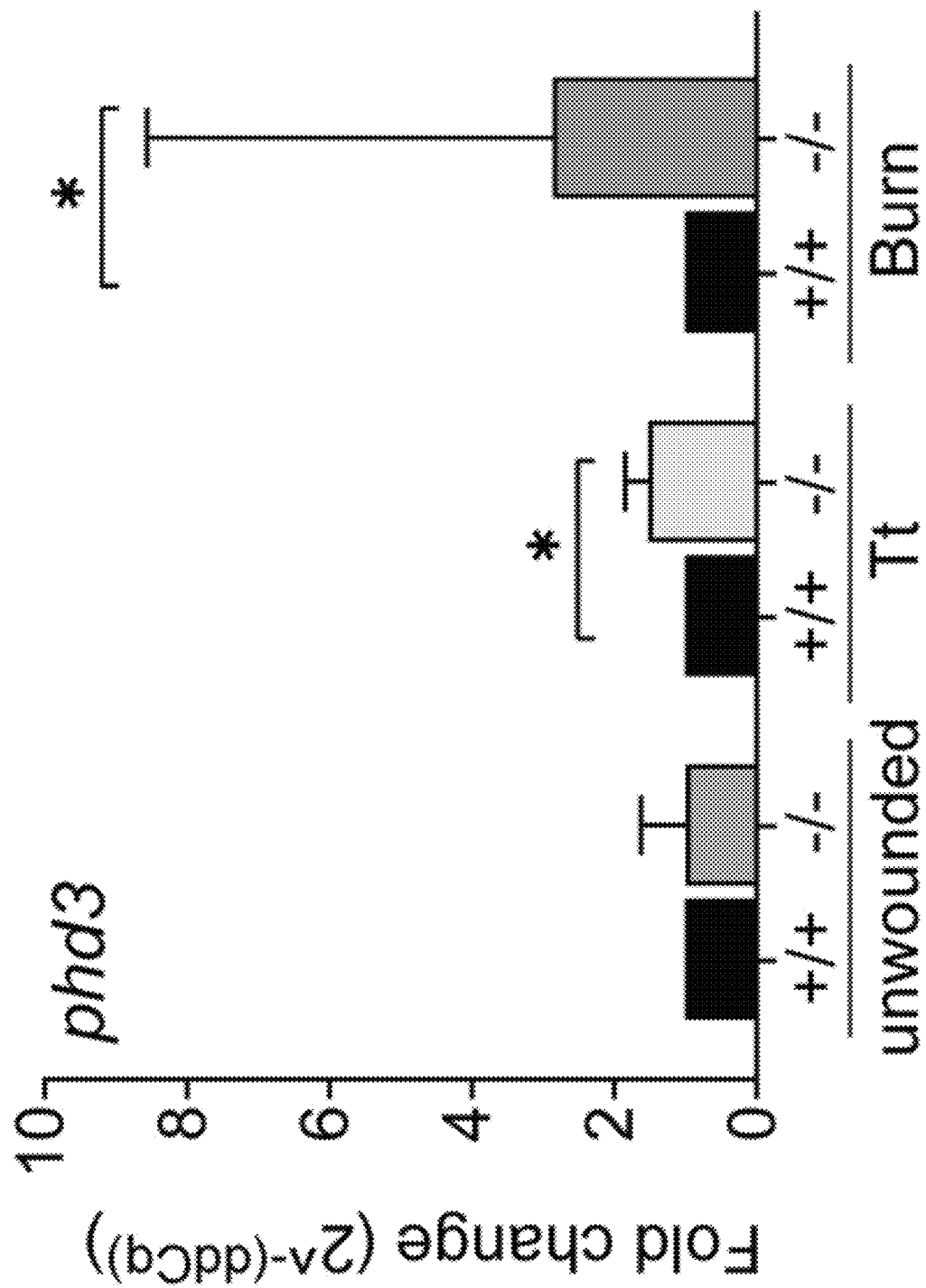

Neutrophils accumulate in MYDGF-deficient larvae via HIF-1α pathway-dependent mechanisms. The HIF-1α pathway is an established regulator of neutrophil accumulation and resolution by reverse migration (Elks et al., 2011). Previous studies have shown that HIF-1α regulates resolution of inflammation by neutrophil reverse migration and apoptosis (FIG. 8A). Given that this well-defined pathway produces a neutrophil recruitment phenotype similar to the one we observed in mydgf$^{-/-}$ larvae (Elks et al., 2011), we asked whether MYDGF exerts its function by modulating the HIF-1α pathway. We measured prolyl hydroxylase 3 (phd3) transcription using reverse transcription quantitative PCR (RT-qPCR) as a surrogate measure of HIF-1α activity (Walmsley et al., 2011). While expression did not differ between unwounded WT and mydgf$^{-/-}$ larvae, we detected a significant increase in phd3 mRNA expression in mydgf$^{-/-}$ larvae following wounding (FIG. 8B).

Figure 8C:
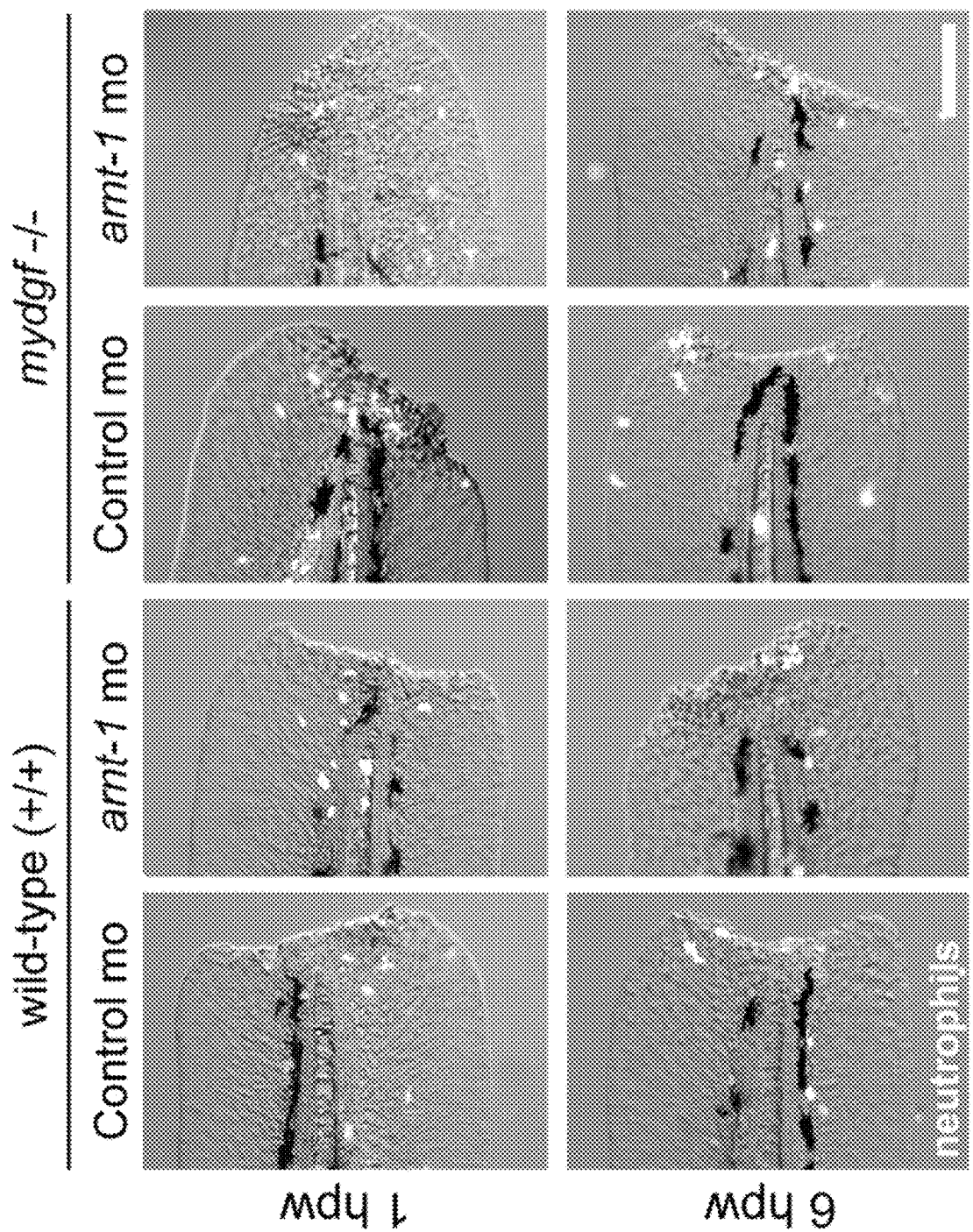
Figure 8D:
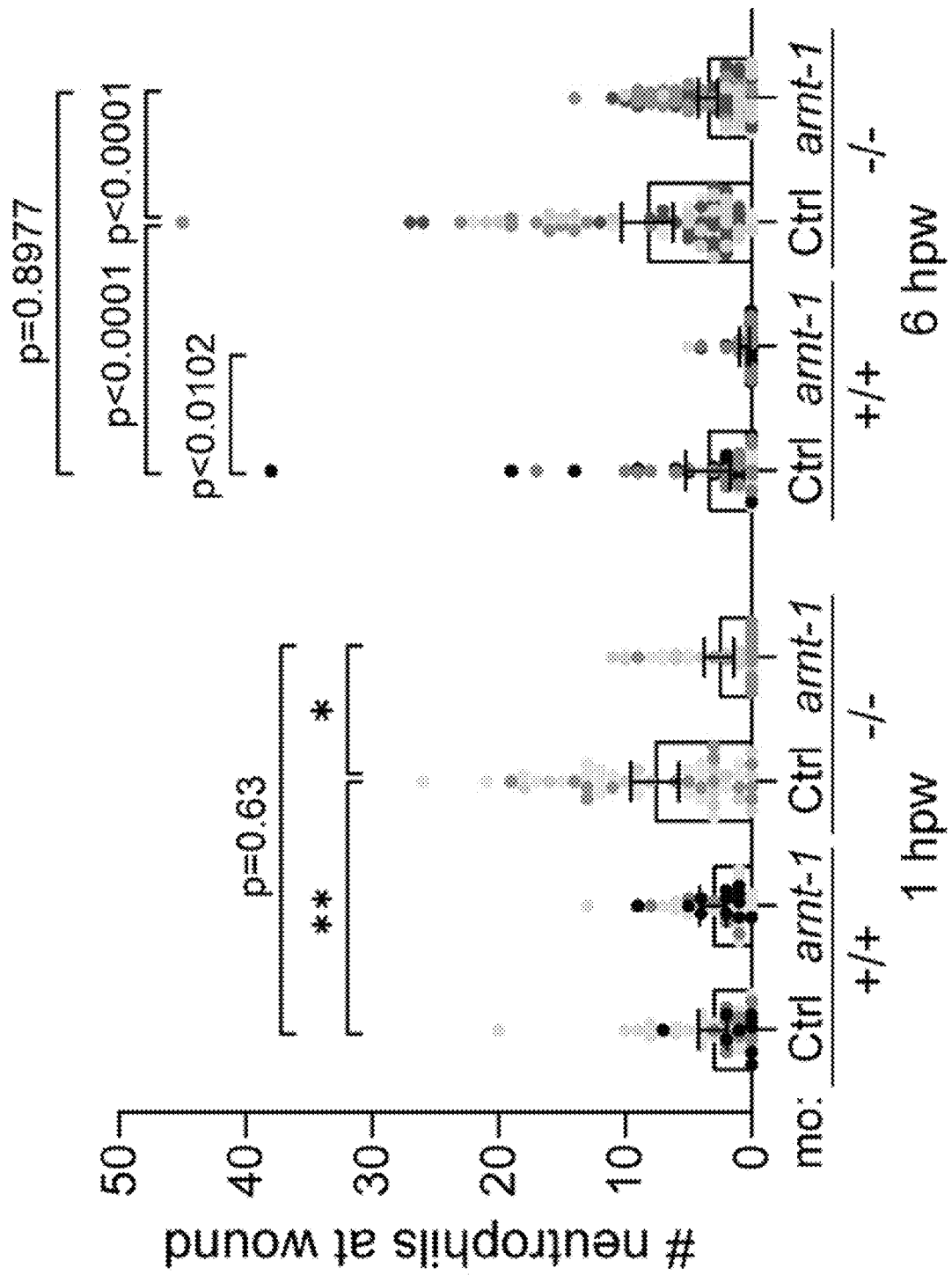

Next, we tested whether disrupting the HIF-1α pathway would reduce neutrophil accumulation in wounded mydgf$^{-/-}$ larvae using an established mo targeting arnt-1, a critical binding partner of HIF-1α (FIG. 8A; Elks et al., 2011). We found that depletion of arnt-1 in mydgf$^{-/-}$ larvae significantly decreased neutrophil numbers at the wound at both 1 and 6 hpw, similar to those observed in WT larvae (FIGS. 8C and 8D). These findings suggest that in the absence of MYDGF, HIF-1α activity is increased in response to tissue damage and leads to neutrophil accumulation at sites of tissue injury in a HIF-1α-dependent manner.

Our findings suggest that MYDGF functions as an endogenous inhibitor of neutrophil inflammation. Given its widespread expression (Bortnov et al., 2018), MYDGF may have a similar role in the regulation of inflammation in other tissues. Indeed, MYDGF expression is increased in a number of disease contexts in which the innate immune system is a major player, including diabetic nephropathy (He et al., 2020), rheumatoid arthritis (Weiler et al., 2007), and hepatocellular carcinoma (Sunagozaka et al., 2011).

MYDGF is a resident protein in the ER, and in silico modeling suggests docking of MYDGF with KDEL receptors (Bortnov et al., 2019). One of the consequences of ER stress is the release of resident ER proteins, including MYDGF (Trychta et al., 2018). Thus, MYDGF may be broadly released by stressed cells after tissue damage, and provide a beneficial effect by limiting neutrophil inflammation. Persistent neutrophil inflammation in tissues in mydgf mutants was dependent on the HIF-1α pathway, suggesting that MYDGF works with HIF-1α signaling to affect neutrophil accumulation in response to tissue damage.

In summary, we found that MYDGF limits neutrophil inflammation in response to tissue damage, but not microbial cues. MyDGF can be used to inhibit inflammation in a subject by modulating neutrophil recruitment to wound sites.

Myeloid-derived growth factor effects on the invasion of melanoma in a zebrafish model of cancer metastasis. A transplantable zebrafish melanoma model system was used to study the role of tumor microenvironment-specific MyDGF on neutrophil recruitment to tumor cells and tumor progression. For the specifics on the melanoma model system, see Heilmann S, et al. "A quantitative system for studying metastasis using transparent zebrafish," *Cancer Res.* 2015 Oct. 15; 75(20):4272-4282. doi: 10.1158/0008-5472.CAN-14-3319. Epub 2015 Aug. 17 and Roh-Johnson M, et al. "Macrophage-dependent cytoplasmic transfer during melanoma invasion in vivo," *Dev Cell.* 2017 Dec. 4; 43(5):549-562.e6.

Figure 9B:
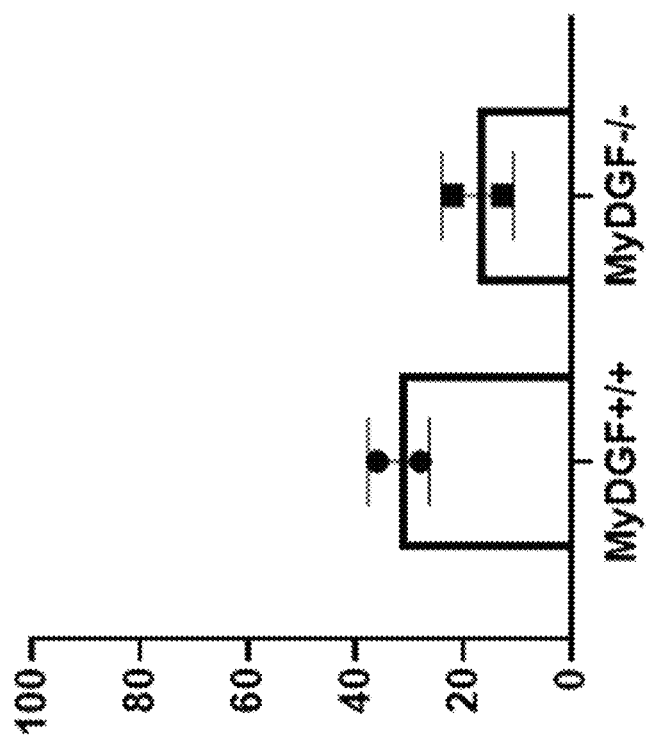
FIGS. 9A-9B. Neutrophil accumulation around tumor cells and number of larvae with disseminated tumor cells in WT and MyDGF-negative mutants with induced melanoma.
Figure 9A:
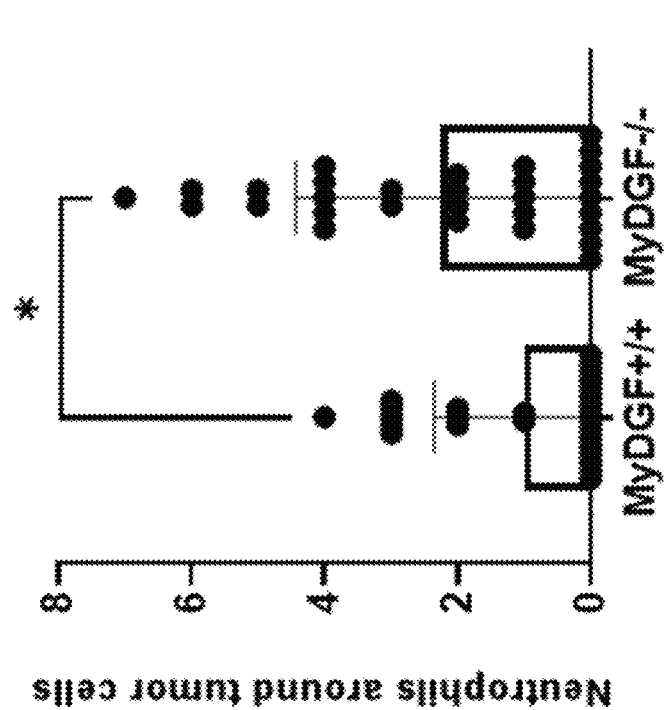

The melanoma was initially induced in zebrafish by expressing BRAFV600E under a melanocyte promoter MITFA in a p53−/− background. The adult fish gave rise to melanoma tumors which were then excised and processed to get the Zebrafish Melanoma cell line (ZMel). To study the role of MyDGF in the tumor micro-environment, we transplanted these cells into the hindbrain of a 2 dpf (days post fertilization) WT or MyDGF-mutant larvae and measured the dissemination of tumor cells to distant sites of the larvae. We also measured the number of neutrophils around the tumor cells at the site of injection. Our preliminary studies, the results of which are depicted in FIGS. 9A and 9B, show that there is a decrease in dissemination of tumor cells in the MyDGF-deficient mutants. We also observed an increase in the number of neutrophils around the tumor cells in the MyDGF mutants, a result that is similar to what we have seen at wounds. See FIGS. 9A and 9B. Because MyDGF plays a pro-wound healing role by mediating resolution of neutrophil inflammation, we hypothesize that in the tumor microenvironment it supports tumor growth and dissemination by modulating immune cell behavior.

Pharmaceutical Compositions:

Also disclosed herein are pharmaceutical compositions comprising a MYDGF or one or more of the MYDGF analogs, orthologs, paralogs, etc., or a pharmaceutically suitable salt thereof as described herein. More specifically, the pharmaceutical composition may comprise one or more of the MYDGF proteins as well as a standard, well-known, non-toxic pharmaceutically suitable carrier, adjuvant or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectable, suppository, or topical ointment or cream. Proper fluidity can be maintained, for example, by maintaining appropriate particle size in the case of dispersions and by use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active MYDGF protein(s), may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, a MYDGF and/or salt thereof produced as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant MYDGF protein.

For intravenous administration, the MYDGF may be incorporated into commercial formulations such as Intralipid©-brand fat emulsions for intravenous injection. ("Intralipid" is a registered trademark of Fresenius Kabi AB, Uppsalla, Sweden.) Where desired, the individual components of the formulations may be provided individually, in kit form, for single or multiple use. A typical intravenous dosage of a representative MYDGF as described herein is from about 0.1 mg to 100 mg daily and is preferably from 0.5 mg to 3.0 mg daily. Dosages above and below these stated ranges are specifically within the scope of the claims.

Possible routes of administration of the pharmaceutical compositions include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers, or propellants in order to form a spray or inhalant. The route of administration will, of course, depend upon the desired effect and the medical stated of the subject being treated. The dosage of the composition to be administered to the patient may be determined by one of ordinary skill in the art and depends upon various factors such as weight of the patient, age of the patient, immune status of the patient, etc., and is ultimately at the discretion of the medical professional administering the treatment.

With respect to form, the composition may be, for example, a solution, a dispersion, a suspension, an emulsion, or a sterile powder which is then reconstituted. The composition may be administered in a single daily dose or multiple doses.

The present disclosure also includes treating inflammation in vertebrates in general, and in mammals in particular, including humans, by administering an anti-inflammatory-effective amount of one or more the MYDGF proteins described herein.

It should be noted that the above-described pharmaceutical compositions may be utilized in connection with non-human animals, both domestic and non-domestic, as well as humans.

REFERENCES

Barros-Becker, F., J. M. Squirrell, R. Burke, J. Chini, J. Rindy, A. Karim, K. W. Eliceiri, A. Gibson, and A. Huttenlocher. 2020. Distinct Tissue Damage and Microbial Cues Drive Neutrophil and Macrophage Recruitment to Thermal Injury. *iScience*. 23:101699.

Bortnov, V. 2020. Myeloid-Derived Growth Factor (MYDGF): Investigations of Structure and Function. The University of Wisconsin—Madison, Ann Arbor. 1-173.

Bortnov, V., D. S. Annis, F. J. Fogerty, K. T. Barretto, K. B. Turton, and D. F. Mosher. 2018. Myeloid-derived growth factor is a resident endoplasmic reticulum protein. *J. Biol. Chem.* 293:13166-13175.

Bortnov, V., M. Tonelli, W. Lee, Z. Lin, D. S. Annis, O. N. Demerdash, A. Bateman, J. C. Mitchell, Y. Ge, J. L. Markley, and D. F. Mosher. 2019. Solution structure of human myeloid-derived growth factor suggests a conserved function in the endoplasmic reticulum. *Nat. Commun.* 10: 5612.

Brubaker, A. L., J. L. Rendon, L. Ramirez, M. A. Choudhry, and E. J. Kovacs. 2013. Reduced neutrophil chemotaxis and infiltration contributes to delayed resolution of cutaneous wound infection with advanced age. *J. Immunol.* 190:1746-1757.

de Oliveira, S., E. E. Rosowski, and A. Huttenlocher. 2016. Neutrophil migration in infection and wound repair: going forward in reverse. *Nat. Rev. Immunol.* 16:378-391.

Deng, Q., S. K. Yoo, P. J. Cavnar, J. M. Green, and A. Huttenlocher. 2011. Dual roles for Rac2 in neutrophil motility and active retention in zebrafish hematopoietic tissue. *Dev. Cell.* 21:735-745.

Ebaid, H. 2014. Neutrophil depletion in the early inflammatory phase delayed cutaneous wound healing in older rats: improvements due to the use of un-denatured camel whey protein. *Diagn. Pathol.* 9:46.

Ebenhoch, R., A. Akhdar, M. R. Reboll, M. Korf-Klingebiel, P. Gupta, J. Armstrong, Y. Huang, L. Frego, I. Rybina, J. Miglietta, et al. 2019. Crystal structure and receptor-interacting residues of MYDGF—a protein mediating ischemic tissue repair. *Nat. Commun.* 10:5379.

Elks, P. M., F. J. van Eeden, G. Dixon, X. Wang, C. C. Reyes-Aldasoro, P. W. Ingham, M. K. B. Whyte, S. R. Walmsley, and S. A. Renshaw. 2011. Activation of hypoxia-inducible factor-1α (Hif-1α) delays inflammation resolution by reducing neutrophil apoptosis and reverse migration in a zebrafish inflammation model. *Blood.* 118:712-722.

Ellett, F., L. Pase, J. W. Hayman, A. Andrianopoulos, and G. J. Lieschke. 2011. mpeg1 promoter transgenes direct macrophage-lineage expression in zebrafish. *Blood.* 117: e49-e56.

Gagnon, J. A., E. Valen, S. B. Thyme, P. Huang, L. Akhmetova, A. Pauli, T. G. Montague, S. Zimmerman, C. Richter, and A. F. Schier. 2014. Efficient mutagenesis by Cas9 protein-mediated oligonucleotide insertion and large-scale assessment of single-guide RNAs. *PLoS One.* 9:e98186.

Harvie, E. A., and A. Huttenlocher. 2015. Non-invasive Imaging of the Innate Immune Response in a Zebrafish Larval Model of *Streptococcus iniae* Infection. *J. Vis. Exp.* 98:52788.

He, M., Y. Li, L. Wang, B. Guo, W. Mei, B. Zhu, J. Zhang, Y. Ding, B. Meng, L. Zhang, et al. 2020. MYDGF attenuates podocyte injury and proteinuria by activating Akt/BAD signal pathway in mice with diabetic kidney disease. *Diabetologia.* 63:1916-1931.

Houseright, R. A., E. E. Rosowski, P. Y. Lam, S. J. M. Tauzin, O. Mulvaney, C. N. Dewey, and A. Huttenlocher. 2020. Cell type specific gene expression profiling reveals a role for complement component C3 in neutrophil responses to tissue damage. *Sci. Rep.* 10:15716.

Huang, C., and P. Niethammer. 2018. Tissue Damage Signaling Is a Prerequisite for Protective Neutrophil Recruitment to Microbial Infection in Zebrafish. *Immunity.* 48:1006-1013.e6.

Huemer, K., J. M. Squirrell, R. Swader, D. C. LeBert, A. Huttenlocher, and K. W. Eliceiri. 2017. zWEDGI: Wounding and Entrapment Device for Imaging Live Zebrafish Larvae. *Zebrafish.* 14:42-50.

Korf-Klingebiel, M., M. R. Reboll, S. Klede, T. Brod, A. Pich, F. Polten, L. C. Napp, J. Bauersachs, A. Ganser, E. Brinkmann, et al. 2015. Myeloidderived growth factor (C19orf10) mediates cardiac repair following myocardial infarction. *Nat. Med.* 21:140-149.

LaFave, M. C., G. K. Varshney, M. Vemulapalli, J. C. Mullikin, and S. M. Burgess. 2014. A defined zebrafish line for high-throughput genetics and genomics: NHGRI-1. *Genetics.* 198:167-170.

Livak, K. J., and T. D. Schmittgen. 2001. Analysis of relative gene expression data using real-time quantitative PCR and the 2(-Delta Delta C(T)) Method. *Methods.* 25:402-408.

Mathias, J. R., B. J. Perrin, T. X. Liu, J. Kanki, A. T. Look, and A. Huttenlocher. 2006. Resolution of inflammation by retrograde chemotaxis of neutrophils in transgenic zebrafish. *J. Leukoc. Biol.* 80:1281-1288.

Maurer, L. M., B. R. Tomasini-Johansson, W. Ma, D. S. Annis, N. L. Eickstaedt, M. G. Ensenberger, K. A. Satyshur, and D. F. Mosher. 2010. Extended binding site on fibronectin for the functional upstream domain of protein F1 of *Streptococcus pyogenes*. *J. Biol. Chem.* 285:41087-41099.

Miskolci, V., J. Squirrell, J. Rindy, W. Vincent, J. D. Sauer, A. Gibson, K. W. Eliceiri, and A. Huttenlocher. 2019. Distinct inflammatory and wound healing responses to complex caudal fin injuries of larval zebrafish. *eLife.* 8:e45976.

Montague, T. G., J. M. Cruz, J. A. Gagnon, G. M. Church, and E. Valen. 2014. CHOPCHOP: a CRISPR/Cas9 and TALEN web tool for genome editing. *Nucleic Acids Res.* 42(W1):W401-7.

Prasch, A. L., R. L. Tanguay, V. Mehta, W. Heideman, and R. E. Peterson. 2006. Identification of zebrafish ARNT1 homologs: 2,3,7,8-tetrachlorodibenzo-p-dioxin toxicity in the developing zebrafish requires ARNT1. *Mol. Pharmacol.* 69:776-787.

Rosowski, E. E., Q. Deng, N. P. Keller, and A. Huttenlocher. 2016. Rac2 Functions in Both Neutrophils and Macrophages To Mediate Motility and Host Defense in Larval Zebrafish. *J. Immunol.* 197:4780-4790.

Rueden, C. T., J. Schindelin, M. C. Hiner, B. E. DeZonia, A. E. Walter, E. T. Arena, and K. W. Eliceiri. 2017. ImageJ2: ImageJ for the next generation of scientific image data. *BMC Bioinformatics.* 18:529.

Sunagozaka, H., M. Honda, T. Yamashita, R. Nishino, H. Takatori, K. Arai, T. Yamashita, Y. Sakai, and S. Kaneko. 2011. Identification of a secretory protein c19orf10 activated in hepatocellular carcinoma. *Int. J. Cancer.* 129: 1576-1585.

Tauzin, S., T. W. Starnes, F. B. Becker, P. Y. Lam, and A. Huttenlocher. 2014. Redox and Src family kinase signaling control leukocyte wound attraction and neutrophil reverse migration. *J. Cell Biol.* 207:589-598.

The UniProt Consortium. 2017. UniProt: the universal protein knowledgebase. *Nucleic Acids Res.* 45(D1):D158-D169.

Trychta, K. A., E. J. Heathward, A. Sulima, S. Bäck, M. Farokhnia, C. T. Richie, L. Leggio, K. C. Rice, and B. K. Harvey. 2018. Extracellular esterase activity as an indicator of endoplasmic reticulum calcium depletion. *Biomarkers.* 23:756-765.

Walmsley, S. R., E. R. Chilvers, A. A. Thompson, K. Vaughan, H. M. Marriott, L. C. Parker, G. Shaw, S. Parmar, M. Schneider, I. Sabroe, et al. 2011. Prolyl hydroxylase 3 (PHD3) is essential for hypoxic regulation of neutrophilic inflammation in humans and mice. *J. Clin. Invest.* 121: 1053-1063.

Wang, J., M. Hossain, A. Thanabalasuriar, M. Gunzer, C. Meininger, and P. Kubes. 2017. Visualizing the function and fate of neutrophils in sterile injury and repair. *Science.* 358:111-116.

Wang, Y., Y. Li, J. Feng, W. Liu, Y. Li, J. Liu, Q. Yin, H. Lian, L. Liu, and Y. Nie. 2020. Mydgf promotes Cardiomyocyte proliferation and Neonatal Heart regeneration. *Theranostics.* 10:9100-9112.

Weiler, T., Q. Du, O. Krokhin, W. Ens, K. Standing, H. El-Gabalawy, and J. A. Wilkins. 2007. The identification and characterization of a novel protein, c19orf10, in the synovium. *Arthritis Res. Ther.* 9:R30.

Yoo, S. K., and A. Huttenlocher. 2011. Spatiotemporal photolabeling of neutrophil trafficking during inflammation in live zebrafish. *J. Leukoc. Biol.* 89:661-667.

Yoo, S. K., Q. Deng, P. J. Cavnar, Y. I. Wu, K. M. Hahn, and A. Huttenlocher. 2010. Differential regulation of protrusion and polarity by PI3K during neutrophil motility in live zebrafish. *Dev. Cell.* 18:226-236.

---

What is claimed is:

1. A method to inhibit neutrophil recruitment to damaged tissue in a subject in need thereof, the method comprising administering to a subject having neutrophil recruitment to a wound and/or a burn at a site on the subject, an effective amount of a myeloid-derived growth factor ("MYDGF") peptide selected from the group consisting of the amino acid sequence of SEQ ID NOS: 1, 3, or 7, or a pharmaceutically suitable salt of any of the foregoing, wherein the amount is effective to inhibit neutrophil recruitment to the wound and/or burn site.

2. The method of any one of claim 1, wherein the peptide is administered to a vertebrate subject.

3. The method of any one of claim 1, wherein the peptide is administered to a mammalian subject.

4. The method of any one of claim 1, wherein the peptide is administered to a human subject.

5. A method to inhibit inflammation in a subject having a cutaneous wound and/or burn, the method comprising administering to the subject an anti-inflammatory-effective amount of a myeloid-derived growth factor ("MYDGF") peptide selected from the group consisting of the amino acid sequence of SEQ ID NOS: 1, 3, or 7, or a pharmaceutically suitable salt of any of the foregoing, wherein the amount is effective to inhibit inflammation of the cutaneous wound and/or burn in the subject.

6. The method of claim 5, wherein the peptide is administered to a vertebrate subject.

7. The method of claim 5, wherein the peptide is administered to a mammalian subject.

8. The method of claim 5, wherein the peptide is administered to a human subject.

9. A method to promote wound healing in a subject in need thereof having a cutaneous wound and/or burn, the method comprising administering to the subject an effective amount of a myeloid-derived growth factor ("MYDGF") peptide selected from the group consisting of the amino acid sequence of SEQ ID NOS: 1, 3, or 7, or a pharmaceutically suitable salt of any of the foregoing, wherein the amount is effective to promote wound healing of the cutaneous wound and/or burn in the subject.

10. The method of any one of claim 9, wherein the peptide is administered to a vertebrate subject.

11. The method of any one of claim 9, wherein the peptide is administered to a mammalian subject.

12. The method of any one of claim 9, wherein the peptide is administered to a human subject.

* * * * *